US008084207B2

(12) United States Patent
Sampath et al.

(10) Patent No.: US 8,084,207 B2
(45) Date of Patent: Dec. 27, 2011

(54) COMPOSITIONS FOR USE IN IDENTIFICATION OF PAPILLOMAVIRUS

(75) Inventors: Rangarajan Sampath, San Diego, CA (US); Lawrence B. Blyn, Mission Viejo, CA (US); Rachael Kreft, Pittsburgh, PA (US); Thomas A. Hall, Oceanside, CA (US); Feng Li, San Diego, CA (US)

(73) Assignee: Ibis Bioscience, Inc., Carlsbad, CA (US)

( * ) Notice: Subject to any disclaimer, the term of this patent is extended or adjusted under 35 U.S.C. 154(b) by 0 days.

(21) Appl. No.: 12/571,925

(22) Filed: Oct. 1, 2009

(65) Prior Publication Data

US 2010/0136515 A1    Jun. 3, 2010

Related U.S. Application Data

(63) Continuation-in-part of application No. 11/368,233, filed on Mar. 3, 2006, now abandoned.

(60) Provisional application No. 60/658,248, filed on Mar. 3, 2005, provisional application No. 60/705,631, filed on Aug. 3, 2005, provisional application No. 60/732,539, filed on Nov. 1, 2005, provisional application No. 60/740,617, filed on Nov. 28, 2005, provisional application No. 61/102,324, filed on Oct. 2, 2008.

(51) Int. Cl.
   *C12Q 1/68* (2006.01)
   *C07H 21/04* (2006.01)

(52) U.S. Cl. .................. 435/6.1; 435/975; 536/24.33

(58) Field of Classification Search .................. None
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,683,202 A | 7/1987 | Mullis |
| 4,849,331 A * | 7/1989 | Lorincz .................. 435/5 |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,527,898 A * | 6/1996 | Bauer et al. .................. 536/24.3 |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |

(Continued)

FOREIGN PATENT DOCUMENTS

DE    19732086 A1    1/1999

(Continued)

OTHER PUBLICATIONS

Gregoire et al. (J Clin Microbiol. Dec. 1989;27(12):2660-5).*
Stratagene ("Gene Characterization Kits" 1988).*
NCBI (Genbank Accession No. U31788; Oct. 17, 1995).*
Sasagawa et al. (Virus Res. Apr. 2000;67(2):127-39).*
NBCI (GENBANK Accession No. HPU31791; Oct. 17, 1995).*
Buck et al ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Aaserud D.J., et al., "Accurate Base Composition of Double-Strand DNA by Mass Spectrometry," American Society for Mass Spectrometry, 1996, vol. 7 (12), pp. 1266-1269.
Aaserud D.J., et al., "DNA sequencing with Blackbody Infrared Radioactive Dissociation of Electrosprayed Ions," International Journal of Mass Spectrometry and Icon Processes, 1997, vol. 167/168, pp. 705-712.
Adam E., et al., "Characterization of Intertype Specific Epitopes on Adenovirus Hexons," Archives of Virology, 1998, vol. 143 (9), pp. 1669-1682.

(Continued)

*Primary Examiner* — Christopher M. Babic
(74) *Attorney, Agent, or Firm* — Lisa Mueller; Michael Best Friedrich LLP; Christopher C. Sappenfield

(57) ABSTRACT

The present invention relates generally to identification of HPV, and provides methods, compositions and kits useful for this purpose when combined, for example, with molecular mass or base composition analysis.

33 Claims, 4 Drawing Sheets

U.S. PATENT DOCUMENTS

| | | | |
|---|---|---|---|
| 5,814,442 A | 9/1998 | Natarajan et al. | |
| 5,822,824 A | 10/1998 | Dion | |
| 5,828,062 A | 10/1998 | Jarrell et al. | |
| 5,830,653 A | 11/1998 | Froehler et al. | |
| 5,830,655 A | 11/1998 | Monforte et al. | |
| 5,830,853 A | 11/1998 | Backstrom et al. | |
| 5,832,489 A | 11/1998 | Kucala | |
| 5,834,255 A | 11/1998 | Van Gemen et al. | |
| 5,845,174 A | 12/1998 | Yasui et al. | |
| 5,849,492 A | 12/1998 | Rogan | |
| 5,849,497 A | 12/1998 | Steinman | |
| 5,849,901 A | 12/1998 | Mabilat et al. | |
| 5,851,765 A | 12/1998 | Koster | |
| 5,856,174 A | 1/1999 | Lipshutz et al. | |
| 5,864,137 A | 1/1999 | Becker et al. | |
| 5,866,429 A | 2/1999 | Bloch | |
| 5,869,242 A | 2/1999 | Kamb | |
| 5,871,697 A | 2/1999 | Rothberg et al. | |
| 5,872,003 A | 2/1999 | Koster | |
| 5,876,936 A | 3/1999 | Ju | |
| 5,876,938 A | 3/1999 | Stolowitz et al. | |
| 5,885,775 A | 3/1999 | Haff et al. | |
| 5,900,481 A | 5/1999 | Lough et al. | |
| 5,928,905 A | 7/1999 | Stemmer et al. | |
| 5,928,906 A | 7/1999 | Koster et al. | |
| 5,965,363 A | 10/1999 | Monforte et al. | |
| 5,965,383 A | 10/1999 | Vogel et al. | |
| 5,972,693 A | 10/1999 | Rothberg et al. | |
| 5,976,798 A | 11/1999 | Parker et al. | |
| 5,981,176 A | 11/1999 | Wallace | |
| 5,981,190 A | 11/1999 | Israel | |
| 5,994,066 A | 11/1999 | Bergeron et al. | |
| 6,001,564 A | 12/1999 | Bergeron et al. | |
| 6,005,096 A | 12/1999 | Matteucci et al. | |
| 6,007,690 A | 12/1999 | Nelson et al. | |
| 6,007,992 A | 12/1999 | Lin et al. | |
| 6,015,666 A | 1/2000 | Springer et al. | |
| 6,018,713 A | 1/2000 | Coli et al. | |
| 6,024,925 A | 2/2000 | Little et al. | |
| 6,028,183 A | 2/2000 | Lin et al. | |
| 6,043,031 A | 3/2000 | Koster et al. | |
| 6,046,005 A | 4/2000 | Ju et al. | |
| 6,051,378 A | 4/2000 | Monforte et al. | |
| 6,054,278 A | 4/2000 | Dodge et al. | |
| 6,055,487 A | 4/2000 | Margery et al. | |
| 6,060,246 A | 5/2000 | Summerton et al. | |
| 6,061,686 A | 5/2000 | Gauvin et al. | |
| 6,063,031 A | 5/2000 | Cundari et al. | |
| 6,074,823 A | 6/2000 | Koster | |
| 6,074,831 A | 6/2000 | Yakhini et al. | |
| 6,090,558 A | 7/2000 | Butler et al. | |
| 6,104,028 A | 8/2000 | Hunter et al. | |
| 6,110,710 A | 8/2000 | Smith et al. | |
| 6,111,251 A | 8/2000 | Hillenkamp | |
| 6,133,436 A | 10/2000 | Koster et al. | |
| 6,140,053 A | 10/2000 | Koster | |
| 6,146,144 A | 11/2000 | Fowler et al. | |
| 6,146,854 A | 11/2000 | Koster et al. | |
| 6,153,389 A | 11/2000 | Haarer et al. | |
| 6,159,681 A | 12/2000 | Zebala | |
| 6,180,339 B1 | 1/2001 | Sandhu et al. | |
| 6,180,372 B1 | 1/2001 | Franzen | |
| 6,187,842 B1 | 2/2001 | Kobayashi et al. | |
| 6,194,144 B1 | 2/2001 | Koster | |
| 6,197,498 B1 | 3/2001 | Koster | |
| 6,214,555 B1 | 4/2001 | Leushner et al. | |
| 6,218,118 B1 | 4/2001 | Sampson et al. | |
| 6,221,587 B1 | 4/2001 | Ecker et al. | |
| 6,221,598 B1 | 4/2001 | Schumm et al. | |
| 6,221,601 B1 | 4/2001 | Koster et al. | |
| 6,221,605 B1 | 4/2001 | Koster | |
| 6,225,450 B1 | 5/2001 | Koster | |
| 6,235,476 B1 | 5/2001 | Bergmann et al. | |
| 6,235,478 B1 | 5/2001 | Koster | |
| 6,235,480 B1 | 5/2001 | Shultz et al. | |
| 6,238,871 B1 | 5/2001 | Koster | |
| 6,238,927 B1 | 5/2001 | Abrams et al. | |
| 6,239,159 B1 | 5/2001 | Brown et al. | |
| 6,258,538 B1 | 7/2001 | Koster et al. | |
| 6,261,769 B1 | 7/2001 | Everett et al. | |
| 6,265,716 B1 | 7/2001 | Hunter et al. | |
| 6,265,718 B1 | 7/2001 | Park et al. | |
| 6,266,131 B1 | 7/2001 | Hamada et al. | |
| 6,266,144 B1 | 7/2001 | Li | |
| 6,268,129 B1 | 7/2001 | Gut et al. | |
| 6,268,131 B1 | 7/2001 | Kang et al. | |
| 6,268,144 B1 | 7/2001 | Koster | |
| 6,268,146 B1 | 7/2001 | Shultz et al. | |
| 6,270,973 B1 | 8/2001 | Lewis et al. | |
| 6,270,974 B1 | 8/2001 | Shultz et al. | |
| 6,274,726 B1 | 8/2001 | Laugharn, Jr. et al. | |
| 6,277,573 B1 | 8/2001 | Koster | |
| 6,277,578 B1 | 8/2001 | Shultz et al. | |
| 6,277,634 B1 | 8/2001 | McCall et al. | |
| 6,290,965 B1 * | 9/2001 | Jansen et al. | 424/199.1 |
| 6,300,076 B1 | 10/2001 | Koster | |
| 6,303,297 B1 | 10/2001 | Lincoln et al. | |
| 6,312,893 B1 | 11/2001 | Van Ness et al. | |
| 6,312,902 B1 | 11/2001 | Shultz et al. | |
| 6,322,970 B1 | 11/2001 | Little et al. | |
| 6,361,940 B1 | 3/2002 | Van Ness et al. | |
| 6,372,424 B1 | 4/2002 | Brow et al. | |
| 6,389,428 B1 | 5/2002 | Rigault et al. | |
| 6,391,551 B1 | 5/2002 | Shultz et al. | |
| 6,393,367 B1 | 5/2002 | Tang et al. | |
| 6,419,932 B1 | 7/2002 | Dale | |
| 6,423,966 B2 | 7/2002 | Hillenkamp et al. | |
| 6,428,955 B1 | 8/2002 | Koster et al. | |
| 6,428,956 B1 | 8/2002 | Crooke et al. | |
| 6,432,651 B1 | 8/2002 | Hughes et al. | |
| 6,436,635 B1 | 8/2002 | Fu et al. | |
| 6,436,640 B1 | 8/2002 | Simmons et al. | |
| 6,453,244 B1 | 9/2002 | Oefner | |
| 6,458,533 B1 | 10/2002 | Felder et al. | |
| 6,468,743 B1 | 10/2002 | Romick et al. | |
| 6,468,748 B1 | 10/2002 | Monforte et al. | |
| 6,475,143 B2 | 11/2002 | Iliff | |
| 6,475,736 B1 | 11/2002 | Stanton, Jr. | |
| 6,475,738 B2 | 11/2002 | Shuber et al. | |
| 6,479,239 B1 | 11/2002 | Anderson et al. | |
| 6,500,621 B2 | 12/2002 | Koster | |
| 6,553,317 B1 | 4/2003 | Lincoln et al. | |
| 6,558,902 B1 | 5/2003 | Hillenkamp | |
| 6,563,025 B1 | 5/2003 | Song et al. | |
| 6,566,055 B1 | 5/2003 | Monforte et al. | |
| 6,568,055 B1 | 5/2003 | Tang et al. | |
| 6,582,916 B1 | 6/2003 | Schmidt et al. | |
| 6,586,584 B2 | 7/2003 | McMillian et al. | |
| 6,589,485 B2 | 7/2003 | Koster | |
| 6,602,662 B1 | 8/2003 | Koster et al. | |
| 6,605,433 B1 | 8/2003 | Fliss et al. | |
| 6,610,492 B1 | 8/2003 | Stanton, Jr. et al. | |
| 6,613,509 B1 | 9/2003 | Chen | |
| 6,613,520 B2 | 9/2003 | Ashby | |
| 6,617,137 B2 * | 9/2003 | Dean et al. | 435/91.1 |
| 6,623,928 B2 | 9/2003 | Van Ness et al. | |
| 6,638,714 B1 | 10/2003 | Linnen et al. | |
| 6,680,476 B1 | 1/2004 | Hidalgo et al. | |
| 6,682,889 B1 | 1/2004 | Wang et al. | |
| 6,705,530 B2 | 3/2004 | Kiekhaefer | |
| 6,706,530 B2 | 3/2004 | Hillenkamp | |
| 6,783,939 B2 | 8/2004 | Olmsted et al. | |
| 6,800,289 B2 | 10/2004 | Nagata et al. | |
| 6,813,615 B1 | 11/2004 | Colasanti et al. | |
| 6,836,742 B2 | 12/2004 | Brekenfeld | |
| 6,852,487 B1 | 2/2005 | Barany et al. | |
| 6,856,914 B1 | 2/2005 | Pelech | |
| 6,875,593 B2 | 4/2005 | Froehler et al. | |
| 6,906,316 B2 | 6/2005 | Sugiyama et al. | |
| 6,906,319 B2 | 6/2005 | Hoyes | |
| 6,914,137 B2 | 7/2005 | Baker | |
| 6,977,148 B2 | 12/2005 | Dean et al. | |
| 6,994,962 B1 | 2/2006 | Thilly | |
| 7,022,835 B1 | 4/2006 | Rauth et al. | |
| 7,024,370 B2 | 4/2006 | Epler et al. | |
| 7,108,974 B2 | 9/2006 | Ecker et al. | |
| 7,198,893 B1 | 4/2007 | Köster et al. | |

| | | |
|---|---|---|
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2001/0053519 A1* | 12/2001 | Fodor et al. ............... 435/6 |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0148988 A1* | 8/2003 | Kool ...................... 514/44 |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| DE | 19802905 A1 | 7/1999 |
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |

| | | |
|---|---|---|
| JP | 24201679 A2 | 7/2004 |
| JP | 2004201641 A | 7/2004 |
| WO | WO8803957 A1 | 6/1988 |
| WO | WO9015157 A1 | 12/1990 |
| WO | WO9205182 A1 | 4/1992 |
| WO | WO9208117 A1 | 5/1992 |
| WO | WO9209703 A1 | 6/1992 |
| WO | WO9219774 A1 | 11/1992 |
| WO | WO9303186 A1 | 2/1993 |
| WO | WO9305182 A1 | 3/1993 |
| WO | WO9308297 A1 | 4/1993 |
| WO | WO9416101 A2 | 7/1994 |
| WO | WO9419490 A1 | 9/1994 |
| WO | WO9421822 A1 | 9/1994 |
| WO | WO9504161 A1 | 2/1995 |
| WO | WO9511996 A1 | 5/1995 |
| WO | WO9513395 A1 | 5/1995 |
| WO | WO9513396 A2 | 5/1995 |
| WO | WO9531997 A1 | 11/1995 |
| WO | WO9606187 A1 | 2/1996 |
| WO | WO9616186 A1 | 5/1996 |
| WO | WO9629431 A2 | 6/1996 |
| WO | WO9632504 A2 | 10/1996 |
| WO | WO9635450 A1 | 11/1996 |
| WO | WO9637630 A1 | 11/1996 |
| WO | WO9733000 A1 | 9/1997 |
| WO | WO9734909 A1 | 9/1997 |
| WO | WO9737041 A2 | 10/1997 |
| WO | WO9747766 A1 | 12/1997 |
| WO | WO9803684 A1 | 1/1998 |
| WO | WO9812355 A1 | 3/1998 |
| WO | WO9814616 A1 | 4/1998 |
| WO | WO9815652 A1 | 4/1998 |
| WO | WO9820020 A2 | 5/1998 |
| WO | WO9820157 A2 | 5/1998 |
| WO | WO9820166 A2 | 5/1998 |
| WO | WO9826095 A1 | 6/1998 |
| WO | WO9831830 A1 | 7/1998 |
| WO | WO9835057 A1 | 8/1998 |
| WO | WO9840520 A1 | 9/1998 |
| WO | WO9854571 A1 | 12/1998 |
| WO | WO9854751 A1 | 12/1998 |
| WO | WO9905319 A2 | 2/1999 |
| WO | WO9912040 A2 | 3/1999 |
| WO | WO9913104 A1 | 3/1999 |
| WO | WO9914375 A2 | 3/1999 |
| WO | WO9929898 A2 | 6/1999 |
| WO | WO9931278 A1 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A2 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0112853 A1 | 2/2001 |
| WO | WO0120018 A2 | 3/2001 |
| WO | WO0123604 A2 | 4/2001 |
| WO | WO0123608 A2 | 4/2001 |
| WO | WO0132930 A1 | 5/2001 |
| WO | WO0140497 A2 | 6/2001 |
| WO | WO0146404 A1 | 6/2001 |
| WO | WO0151661 A2 | 7/2001 |
| WO | WO0151662 A1 | 7/2001 |
| WO | WO0157263 A1 | 8/2001 |
| WO | WO0157518 A2 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |
| WO | WO02070664 A2 | 9/2002 |
| WO | WO02070728 A2 | 9/2002 |
| WO | WO02070737 A2 | 9/2002 |
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03020890 A2 | 4/2003 |
| WO | WO03033732 A2 | 4/2003 |
| WO | WO03018636 A2 | 6/2003 |
| WO | WO03054162 A2 | 7/2003 |
| WO | WO03054755 A2 | 7/2003 |
| WO | WO03060163 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | WO04003511 A2 | 1/2004 |
| WO | WO04009849 A1 | 1/2004 |
| WO | WO04011651 A1 | 2/2004 |
| WO | WO04013357 A2 | 2/2004 |
| WO | WO04040013 A1 | 5/2004 |
| WO | WO04044123 A2 | 5/2004 |
| WO | WO04044247 A2 | 5/2004 |
| WO | WO04052175 A2 | 6/2004 |
| WO | WO04053076 A2 | 6/2004 |
| WO | WO04053141 A2 | 6/2004 |
| WO | WO04053164 A1 | 6/2004 |
| WO | WO04060278 A2 | 7/2004 |
| WO | WO04070001 A2 | 8/2004 |
| WO | WO04072230 A2 | 8/2004 |
| WO | WO04072231 A2 | 8/2004 |
| WO | WO04101809 A2 | 11/2004 |
| WO | WO05003384 A1 | 1/2005 |
| WO | WO05009202 A2 | 2/2005 |
| WO | WO05012572 A1 | 2/2005 |
| WO | WO05024046 A2 | 3/2005 |
| WO | WO05036369 A2 | 4/2005 |
| WO | WO05054454 A1 | 6/2005 |
| WO | WO05075686 A1 | 8/2005 |
| WO | WO05086634 A2 | 9/2005 |
| WO | WO05091971 A2 | 10/2005 |
| WO | WO05098047 A2 | 10/2005 |
| WO | WO05116263 A2 | 12/2005 |
| WO | WO06089762 A1 | 8/2006 |
| WO | WO06094238 A2 | 9/2006 |
| WO | WO06135400 A2 | 12/2006 |
| WO | WO2007014045 A2 | 2/2007 |
| WO | WO2007086904 A2 | 8/2007 |
| WO | WO2008104002 A2 | 8/2008 |
| WO | WO2008118809 A1 | 10/2008 |

OTHER PUBLICATIONS

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbioiogica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucieotides for the Detection of Infectious Bronchitis Virus by Thepolymerase Chain Reaction," Avian Pathology, 1996, vol. 25 (4), pp. 817- 836.

Agostini H.T, et al., "Complete Genome of a JC Virus Genotype Type 6 from the Brain of an African American with Progressive Multifocal Leukoencephalopathy," Human Virology, 1998, vol. 1 (4), pp. 267-272.

Aires De Sousa M., et al., "Bridges from Hospitals to the Laboratory: Genetic Portraits of Methicillin-Resistant Staphylococcus Aureus Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "VIDA: A Virus Database System for the Organization of Animal Virus Genome Open Reading Frames," Nucleic Acids Research, 2001, vol. 29 (1), pp. 133-136.

Allaouchiche B., et al., "Clinical Impact of Rapid Oxacillin Susceptibility Testing Using a PCR Assay in Staphylococcus Aureus Bactaeremia," The Journal of Infection, 1999, vol. 39 (3), pp. 198-204.

Allawi H.T., et al. "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Hames B.D., ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R. M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MSRA ID System for Rapid Identification of Methicillin-Resistant Staphylococcus Aureus," Diagnostic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.

Aronsson F. et al., "Persistance of the Influenza A/WSN/33 Virus RNA at Midbrain Levels of Immunodefective Mice," Journal of Neurovirology, 2001, vol. 7 (2), pp. 117-124.

Ausubel F.M., et al., Eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 " Synthesis and Purification of Oligonucleotides," in: Current Protocols in Molecular Biology" 1998, John Wiley & Sons, Inc., pp. 2.111-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenze, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing Mycobacteria Species," Molecualr and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker C.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clinical Microbiology, 2005, vol. 43 (3), pp. 1064-1068.

Barbour A.G., et al., "Identification of an Uncultivatable Borrelia Species in the Hard Tick Amblyomma Americanum: Possible Agent of a Lyme Disease-Like Illness," The Journal of Infectious Diseases, 1996, vol. 173 (2), pp. 403-409.

Barns S.M., et al., "Detection of Diverse New Francisella-like bacteria in Environmental Samples," Applied and Environmental Microbiology, 2005, vol. 71 (9), pp. 5494-5500.

Baron E.J., "Genetic aspects of Methicillin Resistance in Staphylococcus aureus and MethodsUsed for its Detection in Clinical Laboratories in the United States," Journal of Chemotherapy, 1995, vol. 7 (suppl. 3), pp. 87-92.

Barr I.G., et al., "An Influenza A(H3) Reassortant was Epidemic in Australia and New Zealand in 2003," Journal of Medical Virology, 2005, vol. 76 (3), pp. 391-397.

Barski P., et al., "Rapid Assay for Detection of Methicillin-Resistant Staphylococcus Aureus Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A Streptococci," Journal of Clinical Microbiology, 1996, vol. 34 (4), pp. 953-958.

Beall B., at al., "Survey of emm Gene Sequences and T-Antigen Types from Systemic Streptococcus pyogenes Infection Isolates Collected in San Francisco, california; Atlanta, Georgia; and Connecticut in 1994 and 1995," Journal of Clinical Microbiology, 1997, vol. 35 (5), pp. 1231-1235.

Benko, M. et al., "Family Adenoviridae," Virus Taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al., "Advantages of Thermococcus Kodakaraenis (KOD) DNA Polymerase for PCR-Mass Spectrometry Based Analyses," American Society for Mass Spectrometry, 2003, vol. 14 (6), pp. 601-604.

Berencsi G., et al., "Molecualr Biological Characterization of Adenovirus DNA," Acta Microbiologica et Immunologica Hungarica, 1998, vol. 45 (3-4), pp. 297-304.

Bishop M.J., et al., "Molecular Sequwnce Databases"In: Nucleic Acid and Protein Sequence Analysis, 4th Chapter, Bishop M.J., et al., et al., Eds, IRL Press, 1987, pp. 83-113.

Bisno A.L., "Streptococcus Pyogenes"in: Infectious Diseases and Their Etiologic Agents, vol. 2, Mandell, Eds., Churchill Livingston, New York, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in Staphyiococcus Spp. Strains Isolated from Meat and Dairy Products. Evidence for New Variants of seG and Sel in S. Aurues AB-8802," Journal of Applied Microbiology, 2004, vol. 97 (4), pp. 719-730.

BLAST Search results, Mar. 7, 2006.

Boivin-Jahns V., et al., "Bacterial Diversity in a Deep-Subsurface Clay Environment," Applied and Environmental Microbiology, 1996, vol. 62 (9), pp. 3405-3412.

Bolton E.T., et al., "A General Method for the Isolation of RNA Complementry to DNA," Proceedings of the National Academy of Sciences, 1962, vol. 48, pp. 1390-1397.

Bonk T. et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD for Elisa for Confirmation and Identification of Serogroup Y and W135 Meningcoccal Infections," FEMS Microbiology Letters, 1998, vol. 159 (2), pp. 209-214.

Boubaker K., et al., "Panton-Valentine Leukocidin and Staphyloccoccal Skin Infections in Schoolchildren," Emerging Infectious Diseases, 2004, vol. 10 (1), pp. 121-124.

Bowen J.E., et al., "The Native Virulence Plasmid Combination Affects the Segregational Stability of a Thetareplicating Shuttle Vector in Bacillus Anthracis Var," Journal of Applied Microbiology, 1999, vol. 87 (2), pp. 270-278.
Bowers K.M., et al., "Screening for Methicillin Resistance in Staphylococars Aureus and Coagulasenegative Staphylococci: Evaluation of Three Selective and Mastalex-MRSA latex Agglutination," British Journal of Biomedical Science, 2003, vol. 60 (2), pp. 71-74.
Brakstad O.G., et al., "Direct Identification of Staphylococcus Aureus in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al, "Multiplex Polymerase Chain Reaction for Detection of Genes for Staphylococcus Aureus Themonuclease and Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant Staphylococcus Aureus: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6) pp. 367-777.
Brightwell G. et al., "Genetic Targets for the Detection and Identification of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clinical Microbiology, 2005, vol. 43 (2), pp. 696-702.
Bronzoni R.V.M., et al., "Multiplex Nested PCR for Brazilian Alphavirus Diagnosis,"Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando, FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the Staphylococcal mecA Gene from BACTEC BloodCulture Bottles by the Polymerase Chain Reaction," American Journal of Clinical Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., at al., "Evaluation of MRSA-Screen, a Simple Anti-PBP 2a Slide Latex AgglutinationKit, for Rapid Detection of Methicillin Resistance in Staphylococcus aureus," Journal of Clinical Microbiology, 1999, vol. 37 (5), pp. 1591-1594.
Certificate of Correction mailed Jan. 6, 2009 for U.S. Appl. No. 10/660,996 filed Sep. 12, 2003.
Certificate of Correction mailed Aug. 7, 2007 for U.S. Appl. No. 10/660,997 filed Sep. 12, 2003.
Certificate of Correction mailed Dec. 12, 2006 for U.S. Appl. No. 10/156,608 filed May 24, 2002.
Certificate of Correction mailed Jul. 17, 2007 for U.S. Appl. No. 09/891,793 filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608 filed May 24, 2002.
Certificate of Correction mailed Mar. 31, 2008 for U.S. Appl. No. 10/660,997 filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al.. "New RNA Polymerase from Escerichia Coli Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of Staphylococcus aureus from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.
Chen C.H., et al., Laser Desorption Mass Spectrometry for FastDNA Sequencing [online], Nov. 1994, Retrieved from the Internet:<URL:http://www.ornl.gove/sci/techresources/Human_Genome/publicat/94SANTA/sequencing/segtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N.H., et al., "Mass Spectrometry of Single-Stranded Restriction Fragments Captured by an Undigested Complementry Sequence," Nucleic Acids Research, 2000, vol. 28(8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus Saccharomonaspora," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al,, "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clinical Microbiology, 2005, vol. 43 (4), pp. 1738-1744.
Cloney L., et al., "Rapid Detection of mecA in Methicillin Resistant Staphylococcus Aureus Using Cycling Probe Technology," Molecular and Cellular Probes, 1999, vol. 13 (13), pp. 191-197.

Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus Fusobacterium," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed on Dec. 13, 2002.
Co-pending U.S. Appl. No. 10/323,186, filed on Dec. 18, 2002.
Co-pending U.S. Appl. No. 10/323,187, filed on Dec. 18, 2002.
Co-pending U.S. Appl. No. 10/324,721, filed on Dec. 18, 2002.
Co-pending U.S. Appl. No. 10/521,662, filed on Jul. 21, 2003.
Co-pending U.S. Appl. No. 10/754,415, filed on Jan. 9, 2004.
Co-pending U.S. Appl. No. 10/807,019, filed on Mar. 23, 2004.
Co-pending U.S. Appl. No. 10/845,052, filed on May 12, 2004.
Co-pending U.S. Appl. No. 10/964,571, filed on Oct. 12, 2004.
Co-pending U.S. Appl. No. 11/209,439, filed on Aug. 23, 2005.
Co-pending U.S. Appl. No. 11/674,538, filed on Feb. 13, 2007.
Co-pending U.S. Appl. No. 11/682,259, filed on Mar. 5, 2007.
Co-pending U.S. Appl. No. 11/929,910, filed on Oct. 30, 2007.
Co-pending U.S. Appl. No. 11/930,741, filed on Oct. 31, 2007.
Co-pending U.S. Appl. No. 90/010,209, filed on Jun. 27, 2008.
Co-pending U.S. Appl. No. 90/010,210, filed on Jun. 27, 2008.
Co-pending U.S. Appl. No. 90/010,447, filed on Apr. 9, 2009.
Co-pending U.S. Appl. No. 90/010,448, filed on Apr. 9, 2009.
Co-pending U.S. Appl. No. 60/639068, filed on Dec. 22, 2004.
Co-pending U.S. Appl. No. 60/648,188, filed on Jan. 28, 2005.
Co-pending U.S. Appl. No. 60/369,405, filed on Apr. 1, 2002.
Co-pending U.S. Appl. No. 60/397,365, filed on Jul. 19, 2002.
Co-pending U.S. Appl. No. 60/431,319.
Co-pending U.S. Appl. No. 60/443,443, filed on Jan. 29, 2003.
Co-pending U.S. Appl. No. 60/443,788.
Co-pending U.S. Appl. No. 60/447,529, filed on Feb. 14, 2003.
Co-pending U.S. Appl. No. 60/453,607, filed on Mar. 10, 2003.
Co-pending U.S. Appl. No. 60/461,494.
Co-pending U.S. Appl. No. 60/470,175, May 12, 2003.
Co-pending U.S. Appl. No. 60/501,926, filed on Sep. 11, 2003.
Co-pending U.S. Appl. No. 60/509,911.
Co-pending U.S. Appl. No. 60/604,329, filed on Aug. 24, 2004.
Co-pending U.S. Appl. No. 60/615,337.
Co-pending U.S. Appl. No. 60/701,404, filed on Jul. 21, 2005.
Co-pending U.S. Appl. No. 60/705,631, filed on Aug. 3, 2005.
Co-pending U.S. Appl. No. 60/720,843, filed on Sep. 27, 2005.
Co-pending U.S. Appl. No. 60/747,607, filed on May 18, 2006.
Co-pending U.S. Appl. No. 60/771,101, filed on Feb. 6, 2006.
Co-pending U.S. Appl. No. 60/773,124, filed on Feb. 13, 2006.
Co-pending U.S. Appl. No. 60/891,479.
Co-pending U.S. Appl. No. 60/941,641.
Cornel A.J., et al., "Polymerase Chain Reaction Species Diagnostic Assay for Anopheles Quadrimaculatus Cryptic Species (Diptera:Culicidae) based on Ribosomal DNA ITS2 Sequences," Journal of Mdeical Entomology, 1996, vol. 33 (1), pp. 109-116.
Couto I., et al., "Development of Methicillin Resistance in Clinical Isolates of Staphylococcus Sciuri by Transcriptional Activation of the mecA Homologue Native to the Species," Journal of Bacteriology, 2003, vol. 185 (2), pp. 654-653.
Crain P.F., et al., "Applications of Mass Spectrometry to the Characterization of Oligonucieotides and Nucleic Acids," Current Opinion In Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-SpecificResidues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.

Crawford-Miksza L.K., et al., "Strain Variation in Adenovirus Serotypes 4 and 7a Causing Acute Respitory Disease," Journal of Clinical Microbiology, 1999, vol. 37 (4), pp. 1107-1112.

Crespillo M., et al., "Mitochondrial DNA Sequences for 118 Individuals from Northeastern Spain," International Journal of Legal Medicine, 2000, vol. 114 (1-2), pp. 130-132.

Cui L., et al., "Contribution of a Thickened Cell Wall and Its Glutamine Nonamidated component to the Vancomycin Resistance Expressed by Staphylococcus Aureus Mu50," Antimicrobial Agents and Chemotherapy, 2000, vol. 44 (9), pp. 2276-2285.

Dasen G., et al., "Classification and Identification of Propiolbacteria based on Ribosomal RNA Genes and PCR," Systematic and Applied Microbiology, 1998, vol. 21 (2), pp. 251-259.

De Jong J.C., et al., "Adenoviruses from Human Immunodeficiency Virus-Infected Individuals, Including Two Strains that represent New Candidate Serotypes Ad50 and Ad51 of Species B1 and D, Respectively," Journal of Clinical Microbiology, 1999, vol. 37 (12), pp. 3940-3945.

De La Puente-Redondo V.A., et al., "Comparison of Different PCR Approaches for Typing of Francisella Tularensis Strains," Journal of Clinical Microbiology, 2000, vol. 38 (3), pp. 1016-1022.

Deforce D.L., et al., "Analysis of Oligonucleotides by ESI-MS," Advances in Chromatography, 2000, vol. 40, pp. 539-566.

Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.

Del Blanco Garcia N., et al., "Genotyping of Francisella Tularensis Strains by Pulsed-field gel Electrophroesis, Amplified Fragment Length Polymorphism Fingerprinting, and 16S rRNA gene Sequencing," Journal of Clinical Microbiology, 2002, vol. 40 (8), pp. 2964-2972.

Del Vecchio V.G., et al., "Molecular Genotyping of Methicillin-Resistant Staphylococcus aureus via Fluorophore-Enhanced Repetitive-Sequence PCR," Journal of Clinical Microbiology, 1995, vol. 33 (8), pp. 2141-2144.

Demesure B., et al., "A Set of Universal Primers for Amplification of Polymorphic Non-coding Regions of Mitochondrial and Chioroplast DNA in Plants," Molecular Ecology, 1995, vol. 4, pp. 129-131.

Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.

Deurenberg R.H., et al., "Rapid Detection of Panton-Valentine Leukocidin from Clinical Isolates of Staphylococcus Aureus Strains by Real-Time PCR," FEMS Microbiology Letters, 2004, vol. 240 (2), pp. 225-228.

Deurenberg R.H., et al "The Prevalence of the Staphylococcus Aureus tst Gene among Community- and Hospital-Acquired Strains and Isolates from Wegener's Granulomatosis Patients," FEMS Microbiology Letters, 2005, vol. 245 (1), pp. 185-189.

Deyde V.M. et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.

Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.

Dias Neto E., et al., "Shotgun Sequencing of the Human Transcriptome with ORF Expressed Sequence Tags," Proceedings of the national Academy of Sciences, 2000, vol. 97 (7), pp. 3491-3496.

Diep B.A., et al., "Complete Genome Sequence of USA300, an Epidemic Clone of Community Acquired Meticillin-Resistant Staphylococcus aureus," Lancet, 2006, vol. 367 (9512), pp. 731-739.

Dinauer D.M., et al., "Sequence-Based Typing of HLA Class II DQB1," Tissue Antigens, 2000, vol. 55 (4), pp. 364-368.

Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.

Donehower L.A., et al., "The Use of Primers from Highly Conserved Pol Regions to Identify Uncharacterized Retroviruses by the Polymerase Chain Reaction," Journal of Virological Methods, 1990, Vol. 28 (1), pp. 33-46.

Donofrio J.C., et al., "Detection of Influenza A and B in Respiratory Secretions with.The Polymerase Chain Reaction," PCR Methods and Applications; 1992, vol. 1 (4), pp. 263-268.

Doty P., et al., "Strand Separation and Specific Recombination in Deoxyribonucleic Acids: Physical Chemical Studies," Proceedings of the National Academy of Sciences, 1960, vol. 46 (4), pp. 461-476.

Drosten C., et al., "Identification of a Novel Coronavirus in Patients with Severe Acute Respiratory Syndrome," New England Journal of Medicine, 2003, vol. 348 (20), pp. 1967-1976.

Dubernets S. et al., "A PCR-Based Method for Identification of Lactobacilli at to Genus Level," FEMS Microbiology Letters, 2002, vol. 214 (2), pp. 271-275.

Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.

Ebner K., et al.; "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.

Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 28 (8), pp. 2982-2984.

Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

Echavarria M., et al., "Prediction of Severe Disseminated Adenovirus Infection by Serum PCR," Lancet, 2001, vol. 358 (9279), pp. 384-385.

Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.

Echavarria M., et al., "Use of PCR to Demonstrate Presence of Adenovirus Species B,C, or F as Well as Coinfection with Two Adenovirus Species in Children with Flu-Like Symptoms," Journal of Clinical Microbiology, 2006, vol. 44 (2), pp. 625-627.

Ecker D.J., et al., "Ibis T5000: A Universal Biosensor Approach for Microbiology," Nature Reviews Microbiology, 2008, vol. 6 (7), pp. 553-558.

Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D.J., et al., "The Ibis T5000 Universal Biosensor. An Automated Platform for Pathogen Identfication and Strain Typing," Journal of the Association for Laboratory Automation, 2006, vol. 11 (6), pp. 341-351.

Edwards K.M. et al., "Adenovirus Infections in Young Children," Pediatrics, 1985, vol. 76 (3), pp. 420-424.

Ellis J.S., et al., "Molecular Diagnosis of Influenza," Reviews in Medical Virology, 2002, vol. 12 (6), pp. 375-389.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Elnifro E.M., et al., "PCR and Restriction Endonuclease Analysis for Rapid Identification of Adenovirus Subgenera," Journal of Clinical Microbiology, 2000, vol. 38(6), pp. 2055-2061.

Elsayed S., et al., "Development and Validation of a Molecular Beacon Probe-Based Real-Time Polymerase Chain Reaction Assay for Rapid Detection of Methicillin Resistance in Staphylococcus Aureus," Archives of Pathology and Laboratory Medicine, 2003, vol. 127 (7), pp. 845-849.

EMBL "Arabidopsis Thaliana T-DNA Flanking Sequence, Left Border, Clone 346C06," Accession No. AJ552897, Mar. 29, 2003.

EMBL "Dog (Clone: CXX.147) Primer for STS 147, 3" End, Sequence Tagged Site, Accession No. L15697, Mar. 4, 2000.

EMBL "Human, muscle, Mitochondrial Mutant, 22 nt, segment 2 of 2," Accession No. S90302, Sep. 1, 2004.

EMBL "Sequence 10 from Patent US 6563025," Accession No. AR321656, Aug. 18, 2003.

EMBL "Synthetic Construct DNA, Reverse Primer for Human STS sts-AA031654 at 1p36" Accession No. AB068711, May 21, 2003.

Enright M.C., et al., "A Multilocus Sequence Typing Scheme for Streptococcus Pneumoniae: Identification of Clones Associated with Serious Invasive Disease," Microbiology, 1998, vol. 144 (Pt 11), pp. 3049-3060.

Enright M,C., et al., "Multilocus Sequence Typing for Characterization of Methicillin-Resistant and Methicillin-Susceptible Clones of Staphylococcus Aureus," Journal of Clinical Microbiology, 2000, vol. 38 (3), pp. 1008-1015.

Enright M.C., et al., "Multilocus Sequence Typing of Streptococcus pyogenes and theRelationships between Emm Type and Clone," Infection and Immunity, 2001, vol. 69 (4), pp. 2416-2427.

Enright M.C., et al., "The Evolutionary History of Methicillin-Resistant Staphylococcus Aureus (MRSA)," Proceedings of the National Academy of Sciences, 2002, vol. 99 (11), pp. 7687-7692.

Enright M.C., "The Evolution of a Resistant Pathogen—the Case of MRSA," Current Opinion in Pharmacology, 2003, vol. 3 (5), pp. 474-479.

Eremeeva M.E., et al., "Evaluation of a PCR Assay for Quantitation of Rickettsia rickettsii and Closely Related Spotted Fever Group Rickettsiae," Journal of Microbiology, 2003, vol. 41 (12), pp. 5466-5472.

Erlich H.A., Ed., PCR Technology: Principles and Applications for DNA Amplification, W.H. Freeman and Company, 1989.

Esmans E.L., et al., "Liquid Chromatography-Mass Spectrometry in Nucleoside, Nucleotide and Modified Nucleotide Characterization," Journal of Chromatography, 1998, vol. 794, pp. 109-127.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

European Search Report for Application No. EP10175659.1, mailed on Feb. 9, 2011, 4 pages.

Evans P., et al., "Practical Algorithms for Universal DNA Primer Design: An Exercise in Algorithm Engineering," Currents in Computational Molecular Biology, 2001, pp. 25-26.

Ex Parte Re-Examination Certificate for U.S. Appl. No. 90/010209 mailed Jul. 7, 2009.

Ex Parte Re-Examination Certificate for U.S. Appl. No. 90/010210, mailed Dec. 28, 2010.

Ex Parte Re-Examination Certificate for U.S. Appl. No. 90/010447 mailed Feb. 15, 2011.

Examiner Interview Summary mailed Oct. 3, 2005 for U.S. Appl. No. 10/326,046 filed Dec. 18, 2002.

Examiner Interview Summary mailed Nov. 6, 2008 for U.S. Appl. No. 10/728,486 filed Dec. 5, 2003.

Examiner Interview Summary mailed Jun. 7, 2011 for U.S. Appl. No. 11/930,108 filed Oct. 31, 2007.

Examiner Interview Summary mailed Aug. 10, 2004 for U.S. Appl. No. 09/798,007 filed Mar. 2, 2001.

Examiner Interview Summary mailed Aug. 10, 2004 for U.S. Appl. No. 09/891,793 filed Jun. 26, 2001.

Examiner Interview Summary mailed Aug. 10, 2004 for U.S. Appl. No. 10/156,608 filed May 24, 2002.

Examiner Interview Summary mailed Aug. 10, 2004 for U.S. Appl. No. 10/326,642 filed Dec. 18, 2002.

Examiner Interview Summary mailed May 19, 2003 for U.S. Appl. No. 09/891,793 filed Jun. 26, 2001.

Examiner Interview Summary mailed Oct. 24, 2008 for U.S. Appl. No. 11/582,859 filed Oct. 17, 2006.

Examiner Interview Summary mailed Feb. 27, 2006 for U.S. Appl. No. 10/326,644 filed Dec. 18, 2002.

Examiner Interview Summary mailed Jan. 27, 2006 for U.S. Appl. No. 10/323,211 filed Dec. 18, 2002.

Examiner Interview Summary mailed May 28, 2008 for U.S. Appl. No. 10/660,998 filed Sep. 12, 2003.

Examiner Interview Summary mailed Oct. 28, 2008 for U.S. Appl. No. 11/331,987 filed Jan. 13, 2006.

Examiner Interview Summary mailed Oct. 29, 2008 for U.S. Appl. No. 11/331,978 filed Jan. 13, 2006.

Examiner Interview Summary mailed Oct. 29, 2009 for U.S. Appl. No. 10/660,122 filed Sep. 11, 2003.

Examiner Interview Summary mailed Jul. 31, 2006 for U.S. Appl. No. 10/326,643 filed Dec. 18, 2002.

Extended European Search Opinion for Application No. EP10175659.1, mailed on Feb. 21, 2011, 5 pages.

Extended European Search Report for Application No. EP10179789.2, mailed on Mar. 22, 2011, 9 pages.

Extended European Search Report for Application No. EP10179791.8, mailed on Mar. 17, 2011, 7 pages.

Extended European Search Report for Application No. EP10179795.9, mailed on 22 Mar. 22, 2011, 9 pages.

Facklam R., et al., "Emm Typing and Validation of Provisional M Types for Group A Streptococci," Emerging Infectious Diseases, 1999, vol. 5 (2), pp. 247-253.

Fang H., et al., "Rapid Screening and Identification of Methicillin-Resistant Staphylococcus Aureus from Clinical Samples by Selective-Broth and Real-Time PCR Assay," Journal of Clinical Microbiology, 2003, vol. 41 (7), pp. 2894-2899.

Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.

Farrell D.J., "The Reliability of Microscan Conventional and Rapid Panels to Identify Staphylococcus Aureus and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyornavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.

Final Office Action mailed Aug. 6, 2010 for U.S. Appl. No. 11/929,910 filed Oct. 30, 2007.

Final Office Action mailed Jul. 8, 2010 for U.S. Appl. No. 12/326,800 filed Dec. 2, 2008.

Final Office Action mailed May 12, 2010 for U.S. Appl. No. 11/674,538 filed Feb. 13, 2007.

Final Office Action mailed Apr. 14, 2011 for U.S. Appl. No. 12/049,949 filed Mar. 17, 2008.

Final Office Action mailed Jun. 14, 2011 for U.S. Appl. No. 12/616,422 filed Nov. 11, 2009.

Final Office Action mailed Oct. 14, 2009 for U.S. Appl. No. 10/943,344 filed Sep. 17, 2004.

Final Office Action mailed Nov. 17, 2009 for U.S. Appl. No. 11/582,875 filed Oct. 17, 2006.

Final Office Action mailed Feb. 18, 2010 for U.S. Appl. No. 10/754,415 filed Jan. 9, 2004.

Final Office Action mailed Nov. 20, 2009 for U.S. Appl. No. 11/331,987 filed Jan. 13, 2006.

Final Office Action mailed Jun. 23, 2010 for U.S. Appl. No. 11/930,017 filed Oct. 30, 2007.

Final Office Action mailed Feb. 26, 2009 for U.S. Appl. No. 11/582,863 filed Oct. 17, 2006.

Final Office Action mailed Jul. 28, 2011 for U.S. Appl. No. 11/930,108 filed Oct. 31, 2007.

Final Office Action mailed Jan. 30, 2009 for U.S. Appl. No. 10/844,938 filed May 12, 2004.

Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (3), pp. 538-546.

Fong W.K. et al., "Rapid Solid-Phase Immunoassay for Detection of Methicilin-ResistantStaphylococcus Aureus Using Cycling Probe Technology," Journal of Clinical Microbiology, 2000, vol. 38 (7), pp. 2525-2529.

Fox, A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.

Fox A., et al., "Report of the Bioterrorism Workshop," Journal of Microbiological Methods, 2002, vol. 51 (3), pp. 247-254.

Fox J.P., et al., "The Virus Watch Program: A Continuing Surveillance of Viral Infections in Metropolitan New York Families," American Journal of Epidemiology, 1969, vol. 89 (1), pp. 25-50.

Fox K.F., et al., "Identification of Brucella by Ribosomal-Spacer-Region PCR and Differentiation of Brucell Canis from Other Brucella Spp. Pathogenic for Humans by Carbohydrate Profiles," Journal of Clinical Microbiology, 1998, vol. 36 (11), pp. 3217-3222.

Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.

Francois P., et al., "Rapid Detection of Methicillin-Resistant Staphylococcus Aureus Directly from Sterile or Nonsterile Clinical Samples by a New Molecular Assay," Journal of Clinical Microbiology, 2003, vol. 41 (1), pp. 254-260.

Fraser C.M., et al., "The Mimimal Gene Complement of Mycoplasma Genitalium," Science, 1995, vol. 270 (52350, pp. 397-403.

Freiberg C., et al., "Genome-Wide mRNA Profiling: Impact on Compound Evaluation and Target Identification in Anti-Bacterial research," Targets, 2002, vol. 1 (1), pp. 20-29.

Freymuth F., et al., "Comparison of Multiplex PCR Assays and Conventional Techniques for the Diagnostic of Respitory Virus Infections in Children Admitted to Hospital With an Acute Respitory Illness," Journal of Medical Virology, 2006, vol. 78(11), pp. 1498-1504.

Freymuth F., et al., "Detection of Respitory Syncytial Virus, Parainfluenzavirus 3, Adenovirus Andrhinovirus Sequences in Respitory Tract of Infants by Polymerase Chain Reaction and Hybridzation," Clinical and Diagnostic Virology, 1997, vol. 8 (1), pp. 31-40.

Fuerstenau S.D., et al., "Molecular Weight Determination of Megadaiton DNA Electrospray Ions Using charge Detection Time-of-flight Mass Spectrometry," Rapid Communications in Mass Spectrometry, 1995, vol. 9 (15), pp. 1528-1538.

Fujimoto T., et al., "Single-Tube Multiplex. PCR for Rapid and Sensitive Diagnosis of Subgenus B and Other Subgenera Adenoviruses in clinical Samples," Microbiology and Immunology, 2000, vol. 44 (10), pp. 821-826.

Fujimura S., et al., "Characterization of the mupA Gene in Strains of Methicillin-Resistant Staphylococcus aureus with a Low Level of resistance to Mupirocin," Antimicrobial Agents and Chemotherapy, 2001, vol. 45 (2), pp. 641-642.

Fujimara S., et al., "Isoleucyl-tRNA Synthetase Mutations in Staphylococcus Aureus Clinicallsolates and In Vitro Selection of Low-Level Mupirocin-Resistant Strains," Antimicrobial Agents and Chemotherapy, 2003, vol. 47 (10), pp. 3373-3374.

Fujioka S., et al., "Analysis of Enterovirus Genotypes using Single-Strand Conformation Polymorphisma of Polymerase Chain Reaction Product," Journal of Virological Methods, 1995, vol. 51 (2-3), pp. 253-258.

Gabriel M.N., et al., "Improved mtDNA Sequence Analysis of Forensic Remains using a "Mini-Primer Set"Amplification Strategy," Journal of Forensic Sciences, 2001, vol. 46 (2), pp. 247-253.

Gall J.G., et al., "Construction and Characterization of Hexon-Chimeric Adenoviruses: Specification of Adenovirus Serotype," Journal of Virology, 1998, vol. 72 (12), pp. 10260-10264.

Gammelin M., et al., "Two Subtypes of Nucleoproteins (NP) of Influenza A Viruses," Virology, 1989, vol. 170 (1), pp. 71-80.

Garcia S., et ai., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.

Gaydos C.A., et al., "Adenovirus Vaccines in the U.S. Military," Military Medicine, 1995, vol. 160 (6), pp. 300-304.

Geha D.J., et al., "Multiplex PCR for Identification of Methicillin-Resistant Staphylococci in the Clinical Laboratory," Journal of Clinical Microbiology, 1994, vol. 32 (7), pp. 1768-1772.

Genbank, "{Deletion 6} [Human, Muscle, Mitochondrial Mutant, 22 nt, Segment 2 of 2]," Accession No. S90302.1, Jun. 10, 1992.

Genbank, "Acinetobacter Genomosp. 10 Strain CIP 70.12 RNA Polymerase Subunit B (rpoB) Gene, Complete Cds," Accession No. 78099429, Mar. 11, 2006.

Genbank, "Bovine Parainfluenza Virus 3 Strain Shipping Fever, Complete Genome," Accession No. AF178655, Sep. 19, 2000.

Genbank, "Clostridium Tetani E88, Complete Genome," Accession No. AE015927.1, Feb. 4, 2003.

Genbank, "E. coli Operon rpoBC Coding for the Beta- and Beta"-Subunits of RNA Polymerase (Genes rpoC and rpoB), and Genes rplL, rIpJ, rplA, and rplK Coding for 50S Ribosomal Subunit Proteins L7/L12, L10, L1, and L11, Respectively. (Map position 89-90 min.), Accession No. 42813, Feb. 28, 1992.

Genbank, "E. coli 16S Ribosomal RNA," Accession No. 174375, Aug. 11, 1995.

Genbank, "E.coli Open Reading Frame Upstream of Lou Operon," Accession No. M21150, Sep. 15, 1990.

Genbank, "E.coli rRNA Operon (rrnB) Coding for Glu-tRNA-2, 5S, 16S and 23S rRNA," Accession No. 147581, Sep. 14, 1992.

Genbank, "Enterococcus Malodoratus Strain ATCC43197 Elongation Factor Tu (tufA) Gene, partial Cds," Accession No. AF274728, Dec. 11, 2000.

Genbank "Escherichia Coli str. K-12 substr. MG1655, Complete Genome," Accession No. NC000913, Oct. 15, 2001.

Genbank, "Homo Sapiens HapiotHaplotype.V Mitochondrion, Complete Genome", Accession No. AF381990.1, Dec. 28, 2001.

Genbank, "Human Adenovirus Type 4 Hexon Gene," for Accession No. X84646, Jun. 30, 1995.

Genbank, "Human Coronavirus 229E, Complete Genome," Accession No, AF304460, Jul. 11, 2001.

Genbank, "Human Isolate L34 Mitochondrion D-loop Region", Accession No. U08081.1, Aug. 16, 1994.

GenBank, "il11b08.y1 Human insulinoma Homo sapiens cDNA clone IMAGE:6029534 5-similar to SW:COX3_Human P00414 Cytochrome C Oxidase Polypeptide III;, mRNA sequence", Accession No. BQ581956.1, Jun. 20, 2002.

Genbank; "Influenza B Virus B/Panama/45/90 Polymerase (PB2) mRNA, Complete Cds", Accession No. AF005737, Oct. 4, 1997, pp. 1-3.

Genbank, "Mastadenovirus h7 Hexon Gene," Accession No. Z48571, Apr. 18, 2005.

Genbank, "Mouse Hepatitis Virus Strain MHV-A59 C12 Mutant, Complete Genome," Accession No. AF029248, Jul. 25, 2000.

GenBank, "or72a01.s1 NCI_CGAP_Lu5 Homo sapiens cDNA Clone IMAGE:1601352 3-similar to SW:COX1_Human_P00395 Cytochrome C Oxidase Polypeptide I;, mRNA sequence", Accession No. A1002209.1, Jun. 10, 1998.

Genbank "Staphylococcus Aureus RN4220 ErmC Gene, Partial Cds," Accession No. 18542231, Sep. 16, 2003.

Genbank "Staphylococcus Aureus Strain MSSA476, Complete Genome," Accession No, BX571857.1, Jun. 24, 2004.

Genbank, "Staphylococcus Aureus Subsp. Aureus Mu50, Complete Genorne," Accession No. 15922990. Oct. 4, 2001.

Genbank "Staphylococcus Aureus Subsp. Aureus MW2, Complete Genome," Accession No. GI21281729, May 31, 2002.

Genbank, "Staphylococcus Epidermidis ATCC 12228, Complete Genome," Accession No. AE015929.1, Jan. 2, 2003.
Genbank "Streptococcus Agalactiae 2603V/R, Complete Genome," Accession No. AE009948.1, Aug. 28, 2002.
Genbank, "Streptococcus Anginosus Elongation Factor Tu (tuf) Gene, Partial cds," Accession No. AF276257.1, Jul. 1, 2001.
Genbank, "Streptococcus Pneumoniae Isolate 95.1In00S DNA Gyrase Subunit B (gyeB) Gene, Complete Cds," Accession No. 73916349, Sep. 30, 2005.
Genbank, "Streptococcus Pyogenes Strain MGAS8232, Complete Genome," Accession No. AE009949.1, Apr. 3, 2002.
Genbank, "Venezueian Equine Encephalitis Virus Nonstructural Polyprotein and Structural Polyprotein Genes, Complete Cds," Accession No. AF37505.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5''Fluorogenic Nuclease Assay to Detect and Differentiate Between Ebola Virus Subtypes Zaire and Sudan," Journal of Clinical Microbiology, 2001, vol. 39(11), pp. 4125-4130.
Gilbert N., et al., "Comparison of Commercial Assays for the Quantitation of HBV DNALoad in Healthcare Workers: Caliberation Differences," Journal of Virological Methods, 2002, vol. 100 (1-2), pp. 37-47.
Giles S.R., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant Staphylococcus Aureus Strain and a Biofilm-Producing Methicillin-Resistant Staphylococcus Epidemidis Strain," Journal of Bacteriology, 2005, vol. 187 (7), pp. 2426-2438.
Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.
Ginther C., et al,, "Identifying Individuals by Sequencing Mitochondrial DNA from Teeth," Nature Genetics, 1992, vol. 2(2), pp. 135-138.
Gjoen K.V., et al., "Specific Detection of Coxsackie Viruses A by the Polymerase Chain Reaction," Clinical and Diagnostic Virology, 1997, vol. 8(3), pp. 183-188.
Golden M.R., et al., "Pilot Study of COBAS PCR and Ligase Chain reaction for Detection of Rectal Infections Due to Chlamydia Trachommatis," Journal of Clinical Microbiology, 2003, vol. 41 (5), pp. 2174-2175.
Goto K., et al., "Applications of the Partial 16SrDNA Sequence as an Index for Rapid Identification of Species in the Genus Bacillus," Journal of General and Applied Microbiology, 2000, vol. 46 (1), pp. 1-8.
Gravet A. et al., "characterization of a Novel Structural Member, Luk-E-LukD, of the Bi-Component Staphylococcal Leucotoxins Family," FEBS Letters, 1998, vol. 436(2), pp. 202-208.
Gray G.C., et al., "Adult Adenovirus Infections: Loss of Orphaned Vaccines Precipitates Military respitory Disease Epidemics," Clinical Infectious Diseases, 2000, vol. 31, pp. 663-670.
Greenberg B.D., et al., "Intraspecific Nucleotide Sequence Variability Surrounding the Orgin or Replicationin Human Mitochondrial DNA," Gene, 1983, vol. 21, pp. 33-49.
Griffey, et al., "Detection of Base Pair Mismatches in Duplex DNA and RNA Oligonucleotides Using Electrospray Mass Spectrometry," SPIE, 1997, vol. 2985, pp. 82-86.
Griffin T.J., et al., "Direct Genetic Analysis by Matrix-Assisted Laseer Desoprtion/Ionization Mass Spectrometry," Proceedings of the National Academy of Sciences, 1999, vol. 96 (11), pp. 6301-6306.
Griffin T.J., et al., "Single-Nucleotide Polymorphism Analysis by Maldi-TOF Mass Spectrometry," Trends in Biotechnology, 2000, vol. 18(2), pp. 77-84.
Grondahl B., et al., "Rapid Identification of Nine Microorganisms Causing Acute Respitory TractInfections by Single-Tube Multiplex Reverse Transcription-PCR: Feasibility Study," Journal of Clinical Microiology, 1999, vol. 37 (1), pp. 1-7.
Grundmann H., et al., "Emergence and Resurgence of Meticillin-Resistant Staphylococcus Aureus as a Public-Health Threat," Lancet, 2006, vol. 368(9538), pp. 874-885.
Grzybowski T., et al., "Extremely High Levels of Human Mitochondrial DNA Heteroplasmy in Single Hair Roots," Electrophoresis, 2000, vol. 21 (3), pp. 548-553.
Gu Z., et al., "Multiplexed, Real-Time PCR for Quantitative Detection of Human Adenovirus," Journal of Clinical Microbiology, 2003, vol. 41 (10), pp. 4636-4641.
Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2(2), pp. 217-226.
Haff L.A., et al., "Multiplex Genotyping of PCR Products with Mass Tag-Labeled Primers, " Nucleic Acids Research, 1997, vol. 25 (18), pp. 3749-3750.
Hahner S., et al., "Analysis of Short Tandem Repeat Polymorphisma by Electrospray Ion Trap Mass Spectrometry," Nucleic Acids Research, 2000, vol. 28 (18), pp. E.82.1-E82.8.
Haines J.D., et al., "Medical Response to Bioterroism: Are We Prepared," Journal of Oklahoma State Medical Association, 2000, vol. 93, pp. 187-196.
Hall T.A., et al., "Base Composition Analysis of human Mitochondrial DNA Using Electrospray Ionization Mass Spectrometry: A Novel Tool for the Identification and Differentiation of Humans," Analytical Biochemistry, 2005, vol. 344 (1), pp. 53-69.
Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, vol. 12 (3), pp. 177-185.
Hamel S., et al., "Consensus PCR and Microarray for Diagnosis of the Genus Staphylococcus, Species, and Methicillin resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," archives of Virology, 1996, vol. 141 (11), pp. 2103-2114.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.
Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.
Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.
Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "Sccmecin Staphylococci: Genes on the Move," FEMS Immuol Medical Microbiol, 2006, vol. 46, pp. 8-20.
Hasebe F. et al., "Combined Detection and Genotyping of Chikungunya Virus by a Specific reverse Transcription-Polymerase chain Reaction," Journal of Medical Virology, 2002, vol. 67 (3), pp. 370-374.
Hassan A.A., et al., "Inter- and Intraspecies Variations of the 16S-23S rDNA Intergenic Spacer Region of Various Streptococcal Species," Systemic and Applied Microbiology, 2003, vol. 26(1), pp. 97-103.
Haugland R.A., et al., "Identification of Putative Sequence Specific PCR Primers for Detection of the Toxygenic Fungal Species Stachybotrys Chartarum," Molecular and Cellular Probes, 1998, vol. 12 (6), pp. 387-396.

Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.

He L., et al., "Development of a Capillary High-performance Liquid Chromatography Tandem Mass Spectrometry System Using SWIFT Technology in an Ion Trap/Reflectron time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Virology, 2003, vol. 70, pp. 228-239.

Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.

Herrmann B., et al., "Differentiation of Chiamydia spp. by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., "Sensitive and Rapid Identification of Biological Threat Agents," annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant Staphylococcusaureus," Trends Microbiology, 2001, vol. 9 (10), pp. 486-493.

Hodgson J.E., et al., "Molecular Characterization of the Gene Encoding High-Level Mupirocin Resistancein Staphylococcus aureus J2870," Antimicrobial Agents and Chemotherapy, 1994, vol. 38 (5), pp. 1205-1208.

Hoffman E., et al., "Rescue of Influenza B virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses," Archives of Virology, 2001, vol. 146 (12), pp. 2275-2289.

Hofstadler S.A., et al., "TIGER: The Universal Biosensor," International Journal of Mass Spectrometry, 2005, vol. 242, pp. 23-41.

Holden M.T., et al., "Complete Genomes of Two Clinical Staphylocuccus Aureus Strain: Evidence for the Rapid Evolution of Virulence and Drug Resistance," Proceedings of the National Academy of Sciences, 2004, vol. 101 (26), pp. 9786-9791.

Holland M.M., et al., "Mitochondrial DNA Sequence Analysis—Validation and Use for Forensic Casework," Forensic Science review, 1999, vol. 11 (1), pp. 22-50.

Holland M.M., et al., "Mitochondrial DNA Sequence Analusis of Human Skeletal Remains: Identification of Remains from the Vietnam War," Journal of Forensic Sciences, 1992, vol. 38 (3), pp. 542-553.

Holm L., et al., "Removing Near-Neighbour Redundancy from Large Protein Sequence Collections," Bioinformatics, 1998, vol. 14 (5), pp. 423-429.

Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.

Honda K., et al., "Universal Method of Hypersensitive Nested PCR Toward Forensic DNA typing," International Congress Series, 1998, vol. 7, pp. 28-30.

Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.

Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis os Adenovirus Type 4 Infection Using a Hexon-Based Quantitative Fluorogenic PCR," Diagnostic Microbiology and Infectious Disease, 2002, vol. 42 (4), pp. 227-236.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.

Huber C.G., et al., "On-Line Cation Exchange for Supression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time Pcr Assay for Rapid Detection of Methicillin-Resistantstaphylococcus Aureus Directly from Specimans Containing a Mixture of Staphylococci," Journal of Clinical Microbiology, 2004, vol. 42 (5), pp. 1875-1884.

Hunag C., et al., "Detection of Aboviral RNA Directly from Mosquito Homogenates by Reverse Transcription-Polymerase Chain Reaction," Journal of Virological Methods, 2001, vol. 94(1-2), pp. 121-128.

Hung E.C., et al., "Detection of SARS Coronavirus RNA in the Cerebrospinal Fluid of a Patient with Severe Acute Respitory Syndrome," Clinical Chemistry, 2003, vol. 49 (12), pp. 2108-2109.

Hurdle J.G., et al., "Analysis of Mupirocin Resistance and Fitness in Staphylococcus aureus by Molecular Genetic and Structural Modeling Techniques," Antimicrobial Agents and Chemotherapy, 2004, vol. 48(11), pp. 4366-4376.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hurst G.B., et al., "MALDI-TOF Analysis of Polymerase ChainReaction Products from Methanotrophic Bacteria," Analytical Chemistry, 1998, vol. 70 (13), pp. 2693-2698.

Hutchison C.A., et al., "Maternal Inheritance of Mammalian Mitochondrial DNA," Nature, 1974, vol. 251 (5475), pp. 536-538.

Hyde-Deruyscher R., et al., "Polyomavirus Early-Late Switch is not Regualted at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.

Ihle O., et al., "Efficient Purification of DNA Fragments using a Protein Binding Membrane," Nucleic Acids Research, 2000, vol. 28 (16), p. e76.

Inglis T.J., et al., "Rapid Genotyping Confirmation of Methicillin Resistance," Pathology, 1996, vol. 28 (3), pp. 259-261.

Ingman M., et al., "Mitochondrial Genome Variation and the Origin of Modern Humans," Nature, 2000, vol. 408 (6813), pp. 708-713.

International Preliminary Examination Report for Application No. PCT/US2002/06763, mailed Jun. 11, 2003, 6 pages.

International Preliminary Examination Report for Application No. PCT/US2002/20336, mailed on Apr. 26, 2004, 8 pages.

International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.

International Preliminary Examination Report for Application No. PCT/US2003/38505, mailed on Mar. 3, 2006, 5 pages.

International Preliminary Examination Report for Application No. PCT/US2003/38757, mailed on Feb. 2, 2007, 5 pages.

International Preliminary Examination Report for Application No. PCT/US2003/38761, mailed on Jun. 27, 2006, 6 pages.

International Preliminary Report on Patentability and Written Opinion for Application No. PCT/US04/007236, mailed on Mar. 16, 2006, 7 pages.

International Preliminary Report on Patentability and Written Opinion for Application No. PCT/US2005/00386, mailed on Jul. 10, 2006, 6 pages.

International Preliminary Report on Patentability and Written Opinion for Application No. PCT/US2005/030058, mailed on Sep. 25, 2007, 6 pages.
International Preliminary Report on Patentability and Written Opinion for Application No. PCT/US2005/033707, mailed on Mar. 20, 2007, 6 pages.
International Preliminary Report on Patenability for Application No. PCT/US2004/38757, mailed on Jun. 20, 2006, 1 page.
International Preliminary Report on Patentability for Application No. PCT/US2005/018031, mailed on Nov. 29, 2006, 1 page.
International Preliminary Report for Application No. PCT/US2006/0283977, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US20063/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/020045, mailed on Jan. 8, 2009, 17 pages.
International Search Report and Written Opinion for Application No. PCT/US2008/054926, mailed on Jan. 26, 2009, 15 pages.
International Search Report and Written Opinion for Application No. PCT/US2008/057901, mailed on Aug. 28, 2008, 14 pages.
International Search Report and Written Opinion for Application No. PCT/US2008/064891, mailed on Jun. 29, 2009, 15 pages.
International Search Report for Application No. PCT/US04/007236, mailed on Feb. 24, 2006, 2 pages.
International Search Report for Application No. PCT/US2002/06763, mailed on Oct. 23, 2006, 2 pages.
International Search Report for Application No. PCT/US2002/20336, mailed on Feb. 3, 2003, 4 pages.
International Search Report for Application No. PCT/US2003/009802, mailed on Aug. 3, 2004, 2 pages.
International Search Report for Application No. PCT/US2003/038505, mailed on Apr. 12, 2005, 2 pages.
International Search Report for Application No. PCT/US2003/038830, mailed on Aug. 25, 2004, 4 pages.
International Search Report for Application No. PCT/US2003/22835, mailed on Dec. 12, 2003, 1 page.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/065332, mailed on Nov. 28, 2008, 4 pages.
International Search Report for Application No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42(1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Devergent 16S rRNA-23S rRNA Spacer Sequences of Cyanobacteria," Microbiology, 2000, vol. 146 (pt 6), pp. 1275-1286.
Ito T., et al., "Insights on Antibiotic Resistanceof Staphylococcus Aureus from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant Staphylococcus Aureus," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Gentics, 1995, vol. 91, pp. 33-37.
Jaulhac B., et al., "Specific Detection of the Toxic Shock Syndrome Toxin-1 Gene Using the Polymerase Chain Reaction," Molecular and Cellualar Probes, 1991, vol. 5, pp. 281-284.
Jaulhac B., et al., "Synthetic DNA Probes for Detection of Genes for Enterotoxins A, B, C, D, E and for Tsst-1 In Staphylociccai Strains," Journal of Applied Bacterial, 1992, vol. 72 (5), pp. 386-392.
Jensen M.A., et al., "Rapid Identification of Bacteria on the Basis of Polymerase Chain Reaction-Amplified Ribosomal DNA Spacer Polymorphisma," Applied and Environmental Microbiology, 1993, vol. 59 (4), pp. 945-852.
Jeong J., et al., "Early Screening of Oxacillin-Resistant Staphylococcus Aureus and Staphylococcus Epidermidis from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of Francisella species and Subspecies and Development of a Specific PCR that Distinguishes the Two Major Subspecies of Francisella Tularensis," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in Staphylococcus Aureus by the Polymerase Chain Reaction," Journal of Clinical Microbiology, 1991, vol. 29 (3), pp. 426-430.

Johnson Y.A., et al., "Precise Molecular Weight Determination of PCR Products of the rRNA Intergenic Spacer Region Using Electrospray Quadrupole Mass Spectrometry for Differentiation of B. Subtillis and B. Atrophaeus, Closely elated Species of Bacilli," Journal of Microbiological Methods, 2000, vol. 40 (3), pp. 241-254.

Jonas D., et al., "Rapid PCR-Based Identification of MEthicillin-Resistant Staphylococcus Aureusfrom Screening Swabs," Journal of Clinical Microbiology, 2002, vol. 40(5), pp. 1821-1823.

Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Jurinke C., et al., "Detection of Hepatitis B: Virus DNA In Serum Samples Via Nested PCR and MALDI-TOF Mass Spectrometry," Genetic Analysis: Biomolecular Engineering, 1996, vol. 13 (3), pp. 67-71.

Jurinke C., et al., "MALDI-TOF Mass Spectrometry. A Versatile Tool for High-Performance DNA Analysis," Molecular Biotechnology, 2004, vol. 26 (2), pp. 147-163.

Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.

Kageyama A., et al., "Rapid Detection of Human Fecal Eubacterium Species and Related Genera by Tested PCR Method," Journal of Microbiology, Immunology, 2001, vol. 45 (4), pp. 315-318.

Kajon A.E., et al., "Genome Type Analysis of Brazillian Adenovirus Strains of Serotypres 1,2,3,5,and 7 Collected Between 1976 and 1995," Journal of Medical, 1999, vol. 58 (4), pp. 408-412.

Kasai H., et al., "Construction of the gyrB Database for the Identification and Classification of Bacteria," Genome Informatics. Workshop on Genome Informatics, 1998, pp. 13-21.

Katano H., et al., "Identification of Adeno-Associated Virus Contamination In Cell And Virus By PCR," Biotechniques, 2004, vol. 36 (4), pp. 676-680.

Katayama Y., et al., "Genetic Organization of the Chromosome Region Surrounding mecA inClinical Staphylococcal Strains: Role of is431 -Mediated mecI Deletion in Expression of Resistance inmed-Canying, Low-Level Methicillin-Resistant Staphylococcus haemolyticus," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant Staphylococci by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Datbase Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The Amrican Journal of Tropical Medicine and Hygiene, 1997, vol. 57 (5), pp. 519-525.

Khan S.A., et al., "Simultaneous Detection of Erythromycin-Resistant Methylase Genes ermA and ermC from Staphylococcus Spp. By Multiplex-PCR," Molecular and Cellular Probes, 1999, vol. 13 (5), pp. 381-387.

Kidd A.H., et al., "Rapid Subgenus Identification of Human Adenovirus Isolates bya General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virolofy, 1995, vol. 76 (pt (), pp. 2119-2130.

Kikichi K., et al., "Restriction Fragment Length Polymorphism Analysis of Clinical Isolates of Mycobacterium Haemophilum," Journal of Clinical Microbiology, 1994, vol. 32 (7), pp. 1763-1767.

Kilbourne E.D., "Influenza Pandemics of the 20th Century," Emerging Infectious Disease Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed- Base of Deoxyinosine Residues at the Positions of Codon Degeneracy," Journal od Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesezed RNA up to 150 kDa," Nucleic Acids Research, 1994, vol. 22 (19), pp. 3866-3870.

Kitagawa Y., et al., "Rapid Diagnosis of Methicillin-Resistant Staphylococcus Aureus Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clinical Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of base Substitutions, Nucleotide Additions/Deletions, and Chemical Modifications," Analytical Chemistry, 1999, vol. 71 (14), pp. 2893-2900.

Krahmer M.T., et al., "MS for Identification of Single Nucleotide Polymorphisms and MS/MS for Discrimination of Isomeirc PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of Staphylococcus Aureus and Staphylococcus Epidermidis: Results of the Antimicrobial Resistance Surveillance Study of the Paul-Ehrlich-Society for Chemotherapy, 2001," International JOurnal of Antimicrobial Agents, 2004, vol. 23 (6), pp. 577-581.

Krishnan P.U., et al., "Detection of Methicillin and Mupirocin Resistance in Staphylococcus Aureusisolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a NEw Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348(20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M. et al., "Whole Genome Sequencing of Meticillin-Resistant Staphylococcus Aureus," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "Staphylococcus Aureus Panton Valentine Leukocidin CausesNecrotizing Pneumonia," ScienceExpress, 2007, 8 pages.

Lacroix J.M., et al., "PCR-Based Technique for the Detection of Bacteria in Semen and Urine," Journal of Microbiological Methods, 1996, vol. 26, pp. 61-71.

Lacroix L. et al., "Triplex Formation by Oligonucleotides Containing 5-(1-Propynyl)-2-deoxyuridine: Decreased Magnesium Dependence and Improved Intracellular Gene Targeting," 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L.T., et al., "A Real-Time PCR for SARS-Coronavirus Incorporating Incorporating Target Gene Pre-Amplification," Biochemical and Biophysical Research Communications, 2003, vol. 312 (4), PP. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P. et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-164.

Lee J.A., et al., "Rapid Identification of Human Adenovirus Types 3 and 7 from Respiratory Specimans via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern Equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from Escherichia Coli," European Journal of Biochemistry, 1995, vol. 230(2), pp. 538-548.

Lengyel A., et al., "Characterization of the Main Protein Components of Adenovirus Virion and ItsPossible Use in Laboratory Diagnostics," Acta Microbiologica Immunologica Hungarica, 1998, vol. 43 (3-4), pp. 281-283.

Leroy E.M., et al., "Diagnostics of Ebola Haemorrhagic Fever by RT-PCR in an Epidemic Setting," Journal of Medicinal Virology, 2000, vol. 60 (4), pp. 436-467.

Levi K., et al., "Evaluation of an Isothermal Signal Amplification Method for Rapid Detection of Methicillin-Resistant Staphylococcus Aureus from Patient-Screening Swabs," Journal of Clinical Microbiology, 2003, vol. 41 (7), pp. 3187-3191.

Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.

Levison P.R., et al., "Recent Developments of the Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101"as Expressed in a Growth Chamber Environment," Molecular Breeding, 1999, vol. 5, pp. 33-42.

Li C., et al., "Evolution of H9N2 Inluenza Viruses from Domestic Poultry in Mainland China," Virology, 2005, vol. 4340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, vol. 1263, pp. 610-614.

Li Q.G., et al., "Analysis of 15 Different Genome Types of Adenovirus Type 7 Isolated on FiveContinents," Journal of Virology, 1986, vol. 60 (1), pp. 331-335.

Li Q G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of Caenorhabditis Elegans," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin Inmethicillin-Resistant and Methicillin-Sensitive Staphylococcus Aureus Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of Staphylococcalagr Alleles," Applied and Environmental Microbiology, 2003, vol. 69 (1), pp. 18-23.

Lina G., et al., "Involvement of Paton-Valentine Leukocidin-Producing Staphylococcus Aureus in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantitie of Synthetic Oligonucleotides and DNA Diagnostic Products Dispensed by a Piezoelectric Pipet," Analytical Chemistry, 1997, vol. 69, pp. 4540-4546.

Liitle D.P., et al., "Rapid Sequencing og Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29(1), pp. 81-86.

Liu Y., et al., "An Unusual Gene Arrangement for the Putative Chromosome Replication Origin and Circadianexpression of dnaN in Synechococcus sp. Strain PCC 7942," Gene, 1996, vol. 172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 region of Candidaalbicans and Related Species," Yeast, 1993, vol. 9, pp. 1199-1206.

Louie L., et al., "Evaluation of Three Rapids Methods for Detection of Methicillin Resistance in Staphylococcus Aureus," Journal of Clinical Microbiology, 2000, vol. 38 (6), pp. 2170-2173.

Love B.C., et al., "Cloning and Sequence of the GroESL Heat-Shock Operon of Pasteurella Multocida," Gene, 1995, vol. 166 (1), pp. 179-180.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lu X., et al., "Molecular Typing of Human Adenovirus by PCR and Sequencing of a Partial Region of the Hexon Gene," Archives of Virology, 2006, vol. 151 (8), pp. 1587-1602.

Lubman D.M., Application for Contiuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiology Reviews, 1994, vol. 15 (2-3), pp. 155-173.

Lukashov V.V., et al., "Evolutionary Relationships among Parvoviruses: Virus-Host Coevolution among Autonomous Primate Parvoviruses and Links Between Adeno-Associated and Avian Parvoviruses," Journal of Virology, 2001, vol. 75 (6), pp. 2729-2740.

Ma X.X., et al., "Novel Type of Staphylococcal Cassette Chromosome Mec Identified in Community-Acquired Methicillin-Resistant Staphylcoccus Aureus Starins," Antimicrobial Agents and Chemotherapy, 2002, vol. 46 (4), pp. 1147-1152.

Mack D.H., et al., "A Sensitive Method for the Identification of Uncharacterized Viruses Related To known Virus Groups: Hepadnavirus Model System," Proceedings of the National Academy of Science, 1988, vol. 85 (18), pp. 6977-6981.

Magnuson V.L., et al., "Substrate Nucleotide-Determined Non-Templated Addition of Adenine by Tag DNA Polymerase: Implications for PCR-Based Genotyping and Cloning," BioTechniques, 1996, vol. 21 (4), pp. 700-709.

Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.

Malasig M.D., et al., "Simplified Microneutralization Test for Serotyping Adenovirus Isolates," Journal of Clinical Microbiology, 2001, vol. 39 (8), pp. 2984-2986.

Mangrum J.D., et al., "Solution Compsition and Thermal Denaturationfor the Production of Single-Stranded PCR Amplicons: Piperidine-Induced Destabilization of the DNA Duplex," Journal of the American Society for Mass Spectrometry, 2002, vol. 13 (3), pp. 232-240.

Manian F.A., "Asymptomatic Nasal Carriage of Mupirocin-Resistant, Methicillin-Resistant Staphylococcus Aureus (MRSA) in a Pet Dog Associated with MSRA Infection in Household Contacts," Clinical Infectious Diseases, 2003, vol. 36 (2), pp. e26-e28.

Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Seperation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elogation Factor (3 from Aquifer aeolicus: Cloning, Expression, Purification, and Characterization in a Heterologous Translation System," Protein Expression and Purification, 2000, vol. 18 (3), pp. 257-261.

Martineau F., et al., "Development of a PCR Assay for Identification of Staphylococci at Genus and Species Levels," Journal of Clinical Microbiology, 2001, vol. 39 (7), pp. 2541-2547.

Martineau F., et al., "Species-Specific and Ubiquitous-DNA-Based Assays for Rapid Identification of Staphylococcus Aureus," Journal of Clinical Microbiology, 1998, vol. 36 (3), pp. 618-623.

Martin-Lopez J.V., et al., "Simultaneous PCR Detection of Ica Cluster and Methicillin and Mupirocinresistance Genes in Catheter-Isolated Staphylococcus," International Microbiology, 2004, vol. 7 (1), pp. 63-66.

Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonuleotide N3- >p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on Staphylococcus Aureus," FEMS Microbiology Letters, 2003, vol.220 (2), pp. 287-293.

May A.C., "Percent Sequence Identity: The Need to be Explicit," Structure, 2004, vol. 12 (5), pp. 737-738.

McCabe K.M., et al., "Bacterial Species Identification After DNA Amplification with a Universal Primer Pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740747.

Mehrotra M., et al., "Multiplex PCR for Detection of Genes for Staphylococcus Aureus Enterotoxins, Exfoliative Toxins, Toxic Shock Syndrome Toxin 1, and Methicillin Resistance," Journal of Clinical Microbiology, 2000, vol. 38 (3), pp. 1032-1035.

Meiyu F., et al., "Detection of Flaviviruses by Reverse Transcriptase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of Staphylococcus Aureus and Methicillin-Resistant S. Aureus," Journal of Clinical Microbiology, 2000, vol. 38 (6), pp. 2378-2380.

Merlino J., et al., "Rapid Detection of Non-Multidrug-Resistant and Multidrug-Resistant Methicillin- Resistant Staphylococcus Aureus Using Cycling Probe Technology for the mecA Gene," European Journal of Clinical Microbiology and Infectious Diseases, 2003, vol. 22 (5), pp. 322-323.

Messmer T.O., et al., "Discrimination of Streptococcus Pneumoniae from Other Upper respiratory tract Streptococci by Arbitrary Primed PCR," Clinical Biochemistry, 1995, vol. 28 (6), pp. 567-572.

Metzgar D., et al., "PCR Analysis of Egyptian Repitory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondrial DNA Control Region: Development of an International Standard Forensic Database," Croatian Medical Journal, 2001, vol. 42 (3), pp. 315-327.

Miragaia M., et al., "Genetic Diversity among Mathicillin-Resistant Staphylococcus Epidemis (MRSE)," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "RpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of Fusarium Oxysporum f.sp. Vasinfectum in Cotton Tissue by Polymerase Chain Reaction," Plant Pathology, 1998, vol. 47 (4), pp. 486-494.

Morinaga N., et al., "Purification, Cloning and Characterization of Variant LukE-LukD with Strong Leukocidal Activity of Staphylococcal Bi-Component Leukotoxin Family, " Microbiology and Immunology, 2003, vol. 47 (1), pp. 81-90.

Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al.,"Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C, et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole TIme-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of Staphylococci by Polymerase Chain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93(19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.

Nagy M., et al., "Sequence Analysis of Porcine Adenovirus Serotype 5 Fibre Gene: Evidence for Recombination,"Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene Sequences and Specific Detection for Panton-Valentine Leukocidin," Biochemical and Biophysical Research Communications, 2005, vol. 328 (4), pp. 995-1002.

Nakao H., et al., "Development of a Direct PCR Assay for Detection of the Diphtheria Toxin Gene," Journal of Clinical Microbiology, 1997, vol. 35 (7), pp. 1651-1655.

Narita S., et al., "Phage Conversion of Panton-Valentine Leukocidin in Staphylococcus Aureus: Molecular Analysis of a PVL-Converting Phage, cpSLT," Gene, 2001, vol. 268 (1-2), pp. 195-206.

Naumov G.I., et al., "Discrimination Between the Soil Yeast Species Williopsis Satumus and Williopsis Suaveolens by the Polymerase Chain Reaction with the Universal Primer N21," Microbiology, 2000, vol. 69 (2), pp. 229-233.

Neb Catalog, 1998/1999, pp. 1,79,121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA In Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstruction of Active Recombinant Ship Toxin (Stc) 1 from REcombinant Stxl -A and Sbtl -B Subunits Independently Produced by E. Coli Clones," FEMS Microbiol Letters, 1999, vol. 178 (1), pp. 13-18.

Non-Final Office Action mailed Feb. 2, 2007 for U.S. Appl. No. 10/844,938 filed May 12, 2004.

Non-Final Office Action mailed Oct. 2, 2009 for U.S. Appl. No. 11/929,707 filed Oct. 30, 2007.

Non-Final Office Action mailed Aug. 4, 2010 for U.S. Appl. No. 12/049,949 filed Mar. 17, 2008.

Non-Final Office Action mailed Apr. 6, 2009 for U.S. Appl. No. 11/331,987 filed Jan. 13, 2006.

Non-Final Office Action mailed Apr. 7, 2006 for U.S. Appl. No. 10/964,571 filed Oct. 12, 2004.

Non-Final Office Action mailed Aug. 7, 2007 for U.S. Appl. No. 10/844,938 filed May 12, 2004.

Non-Final Office Action mailed Jun. 10, 2009 for U.S. Appl. No. 10/844,938 filed May 12, 2004.

Non-Final Office Action mailed Jan. 12, 2010 for U.S. Appl. No. 11/491,376 filed Jul. 21, 2006.

Non-Final Office Action mailed Oct. 13, 2010 for U.S. Appl. No. 10/754,415 filed Jan. 9, 2004.

Non-Final Office Action mailed Sep. 16, 2009 for U.S. Appl. No. 11/233,630 filed Sep. 21, 2005.

Non-Final Office Action mailed Apr. 17, 2009 for U.S. Appl. No. 12/211,641 filed Sep. 16, 2008.

Non-Final Office Action mailed Nov. 19, 2003 for U.S. Appl. No. 09/798,007 filed Mar. 2, 2001.

Non-Final Office Action mailed Aug. 20, 2007 for U.S. Appl. No. 11/582,863 filed Oct. 17, 2006.

Non-Final Office Action mailed May 20, 2008 for U.S. Appl. No. 10/844,938 filed May 12, 2004.

Non-Final Office Action mailed Oct. 20, 2004 for U.S. Appl. No. 09/891,793 filed Jun. 26, 2001.

Non-Final Office Action mailed Feb. 23, 2009 for U.S. Appl. No. 10/660,122 filed Sep. 11, 2003.

Non-Final Office Action mailed May 26, 2010 for U.S. Appl. No. 11/869,449 filed Oct. 9, 2007.

Non-Final Office Action mailed Jul. 27, 2006 for U.S. Appl. No. 11/209,439 filed Aug. 8, 2005.
Non-Final Office Action mailed Jun. 28, 2010 for U.S. Appl. No. 11/930,002 filed Oct. 30, 2007.
Non-Final Office Action mailed Sep. 28, 2009 for U.S. Appl. No. 11/930,017 filed Oct. 30, 2007.
Non-Final Office Action mailed Dec. 29, 2010 for U.S. Appl. No. 12/616,422 filed Nov. 11, 2009.
Non-Final Office Action mailed Apr. 30, 2010 for U.S. Appl. No. 11/930,108 filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Notice of Allowance and Examiner Interview Summary mailed Jul. 21, 2011 for U.S. Appl. No. 10/754,415 filed Jan. 9, 2004.
Notice of Allowance mailed Apr. 1, 2011 for U.S. Appl. No. 11/233,630 filed Sep. 21, 2005.
Notice of Allowance mailed Jun. 3, 2009 for U.S. Appl. No. 11/331,978 filed Jan. 13, 2006.
Notice of Allowance mailed Aug. 5, 2010 for U.S. Appl. No. 11/233,630 filed Sep. 21, 2005.
Notice of Allowance mailed Aug. 6, 2009 for U.S. Appl. No. 10/728,486 filed Dec. 5, 2003.
Notice of Allowance mailed Aug. 9, 2011 for U.S. Appl. No. 11/932,002 filed Oct. 30, 2007.
Notice of Allowance mailed Jun. 9, 2011 for U.S. Appl. No. 11/331,987 filed Jan. 13, 2006.
Notice of Allowance mailed Jun. 9, 2011 for U.S. Appl. No. 11/491,376 filed Jul. 21, 2006.
Notice of Allowance mailed Dec. 10, 2010 for U.S. Appl. No. 11/233,630 filed Sep. 21, 2005.
Notice of Allowance mailed Dec. 10, 2010 for U.S. Appl. No. 11/491,376 filed Jul. 21, 2006.
Notice of Allowance mailed Nov. 12, 2009 for U.S. Appl. No. 10/728,486 filed Dec. 5, 2003.
Notice of Allowance mailed Dec. 15, 2008 for U.S. Appl. No. 11/331,978 filed Jan. 13, 2006.
Notice of Allowance mailed Sep. 18, 2009 for U.S. Appl. No. 10/660,998 filed Sep. 12, 2003.
Notice of Allowance mailed Nov. 24, 2009 for U.S. Appl. No. 11/331,978 filed Jan. 13, 2006.
Notice of Allowance mailed May 25, 2011 for U.S. Appl. No. 11/929,707 filed Oct. 30, 2007.
Notice of Allowance mailed Oct. 29, 2009 for U.S. Appl. No. 10/660,122 filed Sep. 11, 2003.
Nubel U., et al., "PCR Primers to Amplify 16S rRNA Genes from Cyanbacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectromettry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT—ICR Mass Spectrometry," The American Society For Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity anf Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of iieS-2 GEne Encoding Mupirocin Resistance in Methicillin-Resistant Staphylococcus Aureus by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Forensic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia, and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608 filed May 24, 2002.
Office Action mailed May 1, 2006 for U.S. Appl. No. 10/660,998 filed Sep. 12, 2003.
Office Action mailed Feb. 2, 2011 for U.S. Appl. No. 11/869,449 filed Oct. 9, 2007.
Office Action mailed Jan. 2, 2009 for U.S. Appl. No. 11/060,135 filed Feb. 17, 2005.
Office Action mailed Jun. 2, 2006 for U.S. Appl. No. 10/933,928 filed Sep. 3, 2004.
Office Action mailed Jun. 2, 2008 for U.S. Appl. No. 11/331,978 filed Jan. 13, 2006.
Office Action mailed Oct. 2, 2008 for U.S. Appl. No. 11/223,630 filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998 filed Sep. 12, 2003.
Office Action mailed Aug. 3, 2009 for U.S. Appl. No. 11/754,174 filed May 25, 2007.
Office Action mailed Dec. 3, 2003 for U.S. Appl. No. 10/325,527 filed Dec. 18, 2002.
Office Action mailed Feb. 3, 2011 for U.S. Appl. No. 12/326,800 filed Dec. 2, 2008.
Office Action mailed Nov. 3, 2008 for U.S. Appl. No. 10/728,486 filed Dec. 5, 2003.
Office Action mailed Apr. 4, 2008 for U.S. Appl. No. 10/829,826 filed Apr. 22, 2004.
Office Action mailed Dec. 4, 2006 for Indian Application No. 1136KOLNP2003 filed Mar. 4, 2002 .
Office Action mailed Feb. 4, 2009 for U.S. Appl. No. 11/404,561 filed Apr. 12, 2006.
Office Action mailed Jun. 4, 2009 for U.S. Appl. No. 10/754,415 filed Jan. 9, 2004.
Office Action mailed May 4, 2010 for U.S. Appl. No. 90/010,447 filed Apr. 9, 2009.

Office Action mailed May 4, 2010 for U.S. Appl. No. 90/010,448 filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for for European Application No. 02709785.6 filed Mar. 4, 2002.
Office Action mailed Sep. 5, 2006 for U.S. Appl. No. 10/660,996 filed Sep. 12, 2003.
Office Action mailed Jan. 6, 2011 Israel Application No. 157661 filed Mar. 4, 2002.
Office Action mailed Jul. 6, 2006 for U.S. Appl. No. 10/660,122 filed Sep. 11, 2003.
Office Action mailed Jul. 6, 2007 for U.S. Appl. No. 10/829,826 filed Apr. 22, 2004.
Office Action mailed Mar. 6, 2009 for U.S. Appl. No. 11/233,630 filed Sep. 21, 2005.
Office Action mailed Nov. 6, 2002 for U.S. Appl. No. 09/798,007 filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998 filed Sep. 12, 2003.
Office Acton mailed Aug. 7, 2007 for U.S. Appl. No. 10/660,998 filed Sep. 12, 2003.
Office Action mailed Feb. 7, 2008 for European Application No. 09766752.8 filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007 filed Mar. 2, 2001.
Office Action mailed Jan. 8, 2007 for U.S. Appl. No. 09/891,793 filed Jun. 26, 2001.
Office Action mailed Mar. 8, 2005 for U.S. Appl. No. 09/891,793 filed Jun. 26, 2001.
Office Action mailed Mar. 8, 2007 for U.S. Appl. No. 11/060,135 filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608 filed May 24, 2002.
Office Action mailed Dec. 9, 2009 for U.S. Appl. No. 90/010,210 filed Jun. 27, 2008.
Office Action mailed Dec. 9, 2009 for U.S. Appl. No. 90/010,447 filed Apr. 9, 2009.
Office Action mailed Dec. 9, 2009 for U.S. Appl. No. 90/010,448 filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122 filed Sep. 11, 2003.
Office Action mailed Jul. 9, 2008 for U.S. Appl. No. 11/331,987 filed Jan. 13, 2006.
Office Action mailed Mar. 9, 2004 for U.S. Appl. No. 09/891,793 filed Jun. 26, 2001.
Office Action mailed Nov. 9, 2010 for U.S. Appl. No. 11/331,987 filed Jan. 13, 2006.
Office Action mailed Dec. 10, 2008 for U.S. Appl. No. 10/829,826 filed Apr. 22, 2004.
Office Action mailed Dec.10, 2009 for U.S. Appl. No. 11/929,910 filed Oct. 30, 2007.
Office Action mailed Feb. 10, 2005 for U.S. Appl. No. 09/798,007 filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210 filed Jun. 27, 2008.
Office Action mailed Jun. 10, 2010 for U.S. Appl. No. 90/010,447 filed Apr. 9, 2009.
Office Action mailed Jun. 10, 2010 for U.S. Appl. No. 90/010,448 filed Apr. 9, 2009.
Office Action mailed Oct. 10, 2007 for U.S. Appl. No. 10/754,415 filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793 filed Jun. 26, 2001.
Office Action mailed Aug. 11, 2010 for U.S. Appl. No. 90/010,447 filed Apr. 9, 2009.
Office Action mailed Aug. 11, 2010 for U.S. Appl. No. 90/010,448 filed Apr. 9, 2009.
Office Action mailed Dec. 11, 2007 for U.S. Appl. No. 10/660,998 filed Sep. 12, 2003.
Office Action mailed Jul. 11, 2003 for U.S. Appl. No. 09/798,007 filed Mar. 2, 2001.
Office Action mailed Jun. 11, 2010 for U.S. Appl. No. 90/010,210 filed Jun. 27, 2008.
Office Action mailed Mar. 11, 2005 for U.S. Appl. No. 10/325,527 filed Dec. 18, 2002.
Office Action mailed May 11, 2007 for U.S. Appl. No. 10/728,486 filed Dec. 5, 2003.
Office Action mailed Jul. 12, 2006 for U.S. Appl. No. 09/891,793 filed Jun. 26, 2001.
Office Action mailed Jul. 12, 2006 for U.S. Appl. No. 10/660,669 filed Sep. 12, 2003.
Office Action mailed Jun. 12, 2008 for U.S. Appl. No. 10/754,415 filed Jan. 9, 2004.
Office Action mailed Jun. 12, 2009 for Chinese Application No. 200420016187.9 filed May 13, 2004.
Office Action mailed May 12, 2002 for U.S. Appl. No. 09/798,007 filed Mar. 2, 2001.
Office Action mailed Aug. 13, 2009 for U.S. Appl. No. 11/674,538 filed Feb. 13, 2007.
Office Action mailed Jul. 13, 2004 for U.S. Appl. No. 09/891,793 filed Jun. 26, 2001.
Office Action mailed Jul. 13, 2007 for U.S. Appl. No. 11/233,630 filed Sep. 21, 2005.
Office Action mailed Jul. 13, 2010 for U.S. Appl. No. 11/929,930 filed Oct. 30, 2007.
Office Action mailed Mar. 13, 2006 for U.S. Appl. No. 10/754,415 filed Jan. 9, 2004.
Office Action mailed Nov. 13, 2003 for U.S. Appl. No. 09/891,793 filed Jun. 26, 2001.
Office Action mailed Sep. 13, 2006 for U.S. Appl. No. 09/891,793 filed Jun. 26, 2001.
Office Action mailed Jul. 14, 2004 for U.S. Appl. No. 10/326,642 filed Dec. 18, 2002.
Office Action mailed Jun. 14, 2004 for U.S. Appl. No. 09/891,793 filed Jun. 26, 2001.
Office Action mailed Mar. 14, 2011 for U.S. Appl. No. 11/930,002 filed Oct. 30, 2007.
Office Action mailed Aug. 15, 2008 for U.S. Appl. No. 11/331,978 filed Jan. 13, 2006.
Office Action mailed Dec. 15, 2008 for Israel Application No. 157661 filed Mar. 4, 2002.
Office Action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135 filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978 filed Jan. 13, 2006.
Office Action mailed Sep. 15, 2005 for U.S. Appl. No. 10/156,608 filed May 24, 2002.
Office Action mailed Apr. 16, 2002 for U.S. Appl. No. 09/798,007 filed Mar. 2, 2001.

Office Action mailed Apr. 16, 2008 for U.S. Appl. No. 11/223,630 filed Sep. 21, 2005.
Office Action mailed Apr. 16, 2009 for U.S. Appl. No. 90/010,210 filed Jun. 27, 2008.
Office Action mailed Aug. 16, 2004 for U.S. Appl. No. 10/325,527 filed Dec. 18, 2002.
Office Action mailed Aug. 16, 2010 for U.S. Appl. No. 11/929,707 filed Oct. 30, 2007.
Office Action mailed Feb. 16, 2011 for U.S. Appl. No. 11/929,910 filed Oct. 30, 2007.
Office Action mailed Jul. 16, 2007 for U.S. Appl. No. 11/331,987 filed Jan. 13, 2006.
Office Action mailed Mar. 16, 2006 for U.S. Appl. No. 09/891,793 filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561 filed Apr. 12, 2006.
Office Action mailed Nov. 16, 2009 for Japanese Application No. 200558488 filed Dec. 5, 2003.
Office Action mailed Jun. 17, 2008 for U.S. Appl. No. 11/582,863 filed Oct. 17, 2006.
Office Action mailed Mar. 17, 2006 for U.S. Appl. No. 10/660,122 filed Sep. 11, 2003.
Office Action mailed Nov. 17, 2006 for U.S. Appl. No. 10/754,415 filed Jan. 9, 2004.
Office Action mailed Oct. 17, 2007 for U.S. Appl. No. 10/728,486 filed Dec. 5, 2003.
Office Action mailed OCt. 17, 2008 for U.S. Appl. No. 11/331,978 filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122 filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108 filed Oct. 31, 2007.
Office Action mailed May 18, 2005 for New Zealand Application No. 527857 filed Mar. 4, 2002.
Office Action Sep. 18, 2006 for U.S. Appl. No. 10/660,997 filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998 filed Sep. 12, 2003.
Office Action mailed Jan. 19, 2007 for U.S. Appl. No. 11/059,776 filed Feb. 17, 2005.
Office Action mailed May 19, 2005 for U.S. Appl. No. 09/891,793 filed Jun. 26, 2001.
Office Action mailed Nov. 19, 2004 for U.S. Appl. No. 10/156,608 filed May 24, 2002.
Office Action mailed Oct. 19, 2007 for U.S. Appl. No. 11/210,516 filed Aug. 24, 2005.
Office Action mailed Sep. 19, 2006 for U.S. Appl. No. 10/660,122 filed Sep. 11, 2003.
Office Action mailed Sep. 19, 2007 for U.S. Appl. No. 10/660,122 filed Sep. 11, 2003.
Office Action mailed Apr. 20, 2007 for U.S. Appl. No. 10/660,122 filed Sep. 11, 2003.
Office Action mailed Apr. 20, 2009 for U.S. Appl. No. 10/891,337 filed Jul. 14, 2004.
Office Action mailed Dec. 20, 2006 for U.S. Appl. No. 10/728,486 filed Dec. 5, 2003.
Office Action mailed Jul. 20, 2005 for U.S. Appl. No. 10/156,608 filed May 24, 2002.
Office Action mailed Jun. 20, 2002 for U.S. Appl. No. 09/798,007 filed Mar. 2, 2001.
Office Action mailed Nov. 20, 2003 for U.S. Appl. No. 10/323,438 filed Dec. 18, 2002.
Office Action mailed Nov. 20, 2006 for U.S. Appl. No. 09/891,793 filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447 filed Apr. 9, 2009.
Office Action mailed Sep. 20, 2010 for U.S. Appl. No. 90/010,448 filed Apr. 9, 2009.
Office Action mailed Apr. 21, 2009 for U.S. Appl. No. 90/010,209 filed Jun. 27, 2008.
Office Action mailed Mar. 21, 2008 for U.S. Appl. No. 10/660,122 filed Sep. 11, 2003.
Office Action mailed May 21, 2008 for U.S. Appl. No. 10/943,344 filed Sep. 17, 2004.
Office Action mailed Nov. 21, 2003 for U.S. Appl. No. 10/326,642 filed Dec. 18, 2002.
Office Action mailed Nov. 21, 2006 for U.S. Appl. No. 10/660,997 filed Sep. 12, 2003.
Office Action mailed Oct. 21, 2005 for U.S. Appl. No. 10/326,641 filed Dec. 18, 2002.
Office Action mailed Oct. 21, 2009 for U.S. Appl. No. 12/326,800 filed Dec. 2, 2008.
Office Action mailed Apr. 22, 2009 for U.S. Appl. No. 11/491,376 filed Jul. 21, 2006.
Office Action mailed Jul. 22, 2008 for U.S. Appl. No. 90/010,209 filed Jun. 27, 2008.
Office Action mailed Jul. 22, 2008 for U.S. Appl. No. 990/010,210 filed Jun. 27, 2008.
Office Action mailed Nov. 22, 2006 for U.S. Appl. No. 10/660,996 filed Sep. 12, 2003.
Office Action mailed Oct. 22, 2007 for U.S. Appl. No. 11/331,987 filed Jan. 13, 2006.
Office Action mailed Sep. 22, 2003 for U.S. Appl. No. 09/798,007 filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210 filed Jun. 27, 2008.
Office Action mailed Feb. 23, 2009 for U.S. Appl. No. 10/943,344 filed Sep. 17, 2004.
Office Action mailed Jan. 23, 2008 for U.S. Appl. No. 10/728,486 filed Dec. 5, 2003.
Office Action mailed Jan. 23, 2008 for U.S. Appl. No. 11/059,776 filed Feb. 17, 2005.
Office Action mailed May 23, 2003 for U.S. Appl. No. 09/891,793 filed Jun. 26, 2001.
Office Action mailed May 23, 2005 for U.S. Appl. No. 10/156,608 filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447 filed Apr. 9, 2009.
Office Action mailed Apr. 24, 2009 for U.S. Appl. No. 90/010,448 filed Apr. 9, 2009.
Office Action mailed Aug. 24, 2010 for U.S. Appl. No. 90/010,210 filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642 filed Dec. 18, 2002.
Office Action mailed Jan. 24, 2005 for U.S. Appl. No. 10/326,642 filed Dec. 18, 2002.
Office ACtion mailed Jan. 24, 2007 for U.S. Appl. No. 10/660,998 filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135 filed Feb. 17, 2005.
Office Action mailed Jul. 24, 2009 for U.S. Appl. No. 11/754,182 filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930 filed Oct. 30, 2007.

Office Action mailed Nov. 24, 2009 for U.S. Appl. No. 90/010,210 filed Jun. 27, 2008.
Office Action mailed Sep. 24, 2009 for U.S. Appl. No. 90/010,210 filed Jun. 27, 2008.
Office Action mailed Aug. 25, 2009 for U.S. Appl. No. 11/754,169 filed May 25, 2007.
Office Action mailed Jun. 25, 2009 for U.S. Appl. No. 11/869,449 filed Oct. 9, 2007.
Office Action mailed Jun. 25, 2009 for U.S. Appl. No. 90/010,210 filed Jun. 27, 2008.
Office Action mailed Mar. 25, 2008 for U.S. Appl. No. 11/060,135 filed Feb. 17, 2005.
Office Action mailed Aug. 26, 2003 for U.S. Appl. No. 09/891,793 filed Jun. 26, 2001.
Office Action mailed Aug. 26, 2010 Canadian Application No. 2508584 filed Dec. 5, 2003.
Office Action mailed Jul. 26, 2004 for U.S. Appl. No. 10/323,438 filed Dec. 18, 2002.
Office Action mailed May 26, 2005 for U.S. Appl. No. 10/156,608 filed May 24, 2002.
Office Action mailed May 26, 2006 for U.S. Appl. No. 10/660,997 filed Sep. 12, 2003.
Office Action mailed Feb. 27, 2003 for U.S. Appl. No. 09/798,007 filed Mar. 2, 2001.
Office Action mailed Feb. 27, 2007 for U.S. Appl. No. 10/754,415 filed Jan. 9, 2004.
Office Action mailed Feb. 27, 2007 for U.S. Appl. No. 10/943,344 filed Sep. 17, 2004.
Office Action mailed Jul. 27, 2006 for U.S. Appl. No. 10/728,486 filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415 filed Jan. 9, 2004.
Office Action mailed Feb. 28, 2006 for U.S. Appl. No. 10/660,996 filed Sep. 12, 2003.
Office Action mailed Jul. 28, 2009 for U.S. Appl. No. 11/754,163 filed May 25, 2007.
Office Action mailed Jul. 28, 2010 for U.S. Appl. No. 90,010,210 filed Jun. 27, 2008.
Office Action mailed May 28, 2003 for U.S. Appl. No. 09/798,007 filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776 filed Feb. 17, 2005.
Office Action mailed Oct. 29, 2009 for U.S. Appl. No. 90/010,447 filed Apr. 9, 2009.
Office Action mailed Oct. 29, 2009 for U.S. Appl. No. 90/010,448 filed Apr. 9, 2009.
Office Action mailed Aug. 30, 2007 for U.S. Appl. No. 10/754,415 filed Jan. 9, 2004.
Office Action mailed Jul. 30, 2008 for Australian Application No. 2004248107 filed Apr. 23, 2004.
Office Action ,ailed Jul. 30, 2009 for Japanese Application No. 2002570692 filed Mar. 4, 2002.
Office Action mailed Jun. 30, 2004 for U.S. Appl. No. 09/798,007 filed Mar. 2, 2001.
Office Action mailed Jun. 30, 2010 for U.S. Appl. No. 90/010,210 filed Jun. 27, 2008.
Office Action mailed Jun. 30, 2010 for U.S. Appl. No. 90/010,447 filed Apr. 9, 2009.
Office Action mailed Jun. 30, 2010 for U.S. Appl. No. 90/010,448 filed Apr. 9, 2009.
Office Action mailed May 30, 2006 for U.S. Appl. No. 10/660,996 filed Sep. 12, 2003.
Office Action mailed Nov. 30, 2009 for U.S. Appl. No. 10/660,122 filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007 filed Mar. 2, 2001.
Office Action mailed Jan. 31, 2007 for Philippines Application No. PH12003500824 filed Mar. 4, 2002.
O'Guinn M.L., et al., "Field Detection of Eastern Equine Encephalitis Virus in the Amazon Basin region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant Staphylococcus Aureus," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant Staphylococcus Aureus Clones in the Community," Journal of Clinical Microbiology, 2002, vol. 40 (11), pp.4289-4294.
Oliveira D.C., et al., "Genetic Organization of the Downstream Region of the mecA Element inMethicillin-Resistant Staphylococcus aureus Isolates Carrying Different Polymorphisma of This Region," Antimicrobial Agents and Chemotherapy, 2000, vol. 44 (7), pp. 1906-1910.
Oliveira D.C, et al., "Multiplex PCR Strategy for Rapid Identification of Structural Types and Variants of the mec Element in Methicillin-Resistant Staphylococcus aureus," Antimicrobial Agents and Chemotherapy, 2002, vol. 46 (7), pp. 2155-2161.
Olsen B., et al., "Transhemispheric Exchange of Lyme Disease Spyrohetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimans by a Multiplex Reverse Transcription-PCR Assay," Journal of Clinical Microbiology, 1998, vol. 36 (11), pp. 3149-3154.
OStrander E.A., et al., "Identification and Characterization of Dinucleotide Repeat (CA)n Markers for Genetic Mapping in Dog," Genomics, 1993, vol. 16 (1), pp. 207-213.
Ounisshi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run ti Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNASequence Analysis to a Forensic Case, " International Journal of Legal Medicine, 1998, vol. 111 (3), pp. 124-132.
Partial European Search Report for Application No. EP01106974, mailed on Dec, 16, 2002, 2 pages.
Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetcs, 1990, vol. 124 (3), pp. 735-742.
Pawa A., et al., "Co-Transfer of Plasmids in Association with Conjugative Transfer of Mupirocin or Mupirocin and Penicillin Resistance in Methicillin-Resistant Staphylococcus Aureus," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.

Peng X., et al., "Rapid Detection of Shigella Species in Environmental Sewage by an Immunocapture PCR with Universal Primers," Applied and Environmental Microbiology, 2002, vol. 68 (5), pp. 2580-2583.

Perez-Roth E., et al., "Multiplex PCR for Simultaneous Identification of Staphylococcus aureus and Detection of Methicillin and Mupirocin Resistance," Journal of Clinical Microbiology, 2001, vol. 39 (11), pp. 4037-4041.

Peters S.E., et al., "Quantification of the Detection of Pneumocystis Carinii by DNA Amplification," Molecular and Cellur Probes, 1992, vol. 6 (2), pp. 115-117.

Pfeffer M., et al., "Genus-Specific Detection of Alphaviruses bya Semi-Mested ReverseTranscription-Polymerase Chain Reaction," American Journal of Tropical Medicine and Hygiene, 1997, vol. 57 (6), pp. 709-718.

Pfeffer M., et al., "Specific Detection of Chikungunya Virus Using a RT-PCR.Nested PCR Combination," Journal of Veterinary Medicine B, 2002, vol. 49 (1), pp. 49-54.

Pieles U., et al., "Matrix-Assisted Laser Desorption Ionization Time-of-Flight Spectrometry: APowerful Tool for the Mass and Sequence Analysis of natural and Modified Oligonucleotides, 787 reexamination," Nucleic Acids REsearch, 1993, vol. 21 (14), pp. 3191-3196.

Pillai S.D., et al., "Rapid Molecular Detection of Microbial Pathogens: Breakthroughs and Challenges," Archives of Virology, 1997, vol. 13, pp. 67-82.

Piper J., et al., "Commercially Available Technique for Rapid Laboratory Detection of MethicillinResistance Among Staphylococcus Aureus," Diagnostic Microbiology and Infectious Disease, 1988, vol. 11 (3), pp. 177-180.

Poddar S.K., et al., "Detection of Adenovirus using PCR and Molecular Beacon," Journal of Virological Methods, 1999, vol. 11 (3), pp. 177-180.

Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.

Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.

Pring-Akerblom P., et al., "PCR-Based Detection and Typing of Human Adenoviruses in Clinical Samples," Research in Virology, 1997, vol. 148 (3), pp. 225-231.

Promega. T4 Polynucleotide Kinase, Technical Bulletin No. 519, 2002.

Puthavathana P., et al., "Molecular Characterization of the Complete Genome of Human Influenza H5N1 Virus Isolates from Thailand," Journal of General Virology, 2005, vol. 86 (2), pp. 423-433.

Qadri S.M., et al., "Rapid Detection of Methicillin-Resistant Staphylococcus Aureus by CrystalMRSA ID System," Journal of Clinical Microbiology, 1994, vol. 32 (7), pp. 1830-1832.

Raaum R.L., et al., "Catarrhine Primate Divergence Dates Estimated from Complete Mitochondria Gemones: Concordance with Fossil and Nuclear DNA Evidence," Journal of Human Evolution, 2005, vol. 48 (3), pp. 237-357.

Ramisse V., et al., "Identification and Characterization of Bacillus Anthracis by Multiplex PCR Analysis of Sequences on Plasmids pX01 and pX02 and Chromosomal DNA," Fems Microbiology Letters, 1996, vol. 145 (1), pp. 9-16.

Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.

Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.

Reischl U., "Application of Molecular Biology-Based Methods to theDiagnosis of Infectious Diseases 1, e72-e77.," Frontiers in Bioscience, 1996, vol. 1 (1), pp. e72-e77.

Reischl U., et al., "Rapid Identification of MEthicillin-Resistant Staphylococcus aureus and Simultaneous Species Confirmation Using Real-Time Fluorescence PCR," Journal of Clinical Microbiology, 2000, vol. 38 (6), pp. 2429-2433.

Roberts M.M., et al., "Three-Dimensional Structure of the Adenovirus Major Coat Protein Hexon," Science, 1986, vol. 232 (4754), pp. 1148-1151.

Roberts M.S., et al., "Recombination and Migration Rates in Natural Populations of Bacillus Subtillis and Bacillus Mojavensis," Evolution, 1995, vol. 49 (6), pp. 1081-1094.

Robinson D.A., et al., "Multilocus Sequence Typing and the Evolution of Methicillin-Resistant Staphylococcus Aureus," Clinical Microbiology and Infection, 2004, vol. 10, pp. 92-97.

Rong S., et al., "Design and Application of 60mer Oligonucleotide Microarray in SARS Coronavirus Detection," Chinese Science Bulletin, 2003, vol. 48 (12), pp. 1165-1169.

Ross P., et al., "High Level Multiplex Genotyping by MALDI-TOF Mass Spectrometry," Nature Biotechnology, 1998, vol. 16 (13), pp. 1347-1351.

Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.

Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.

Rota P.A., et al., "Sequencing of a cDNA Clone of the Nucleoprotein Gene of Influenza B/Ann Arbor/1/86," Nucleic Acids Research, 1989, vol. 17 (9), pp. 3595.

Ruan Y., et al., "Comparative Full-Length Genome Sequence Analysis of 14 SARS Coroavirus Isolates and Common Mutations Associated with the Putative Origins of Infection," The Lancet, 2003, vol. 361, pp. 1779-1785, 1832.

Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.

Rupf S., et al., "Quantitative Determination of Streptococcus Mutans by using Competitive Polymerasechain Reaction," European Journal of Oral Sciences, 1999, vol. 107 (2), pp. 75-81.

Russell K.L., et al., "Transmission Dynamics and Prospective Enviromental Sampling of Adenovirus in a Military Recruit Setting," Journal of Infectious Diseases, 2006, vol. 194 (7), pp. 877-885.

Sabat A., et al., "Comparison of PCR-Based Methods for Typing Staphylococcus Aureus Isolates," Journal of Clinical Microbiology, 2006, vol. 44 (10), pp. 3804-3807.

Sackesen C., et al., "Use of Polymerase Chain Reaction for Detection of Adenovirus in Children Withor Without Wheezing," Turkish Journal of Pediatrics, 2005, vol. 47 (3), pp. 227-231.

Sakai H., et al., "Simultaneous Detection of Staphylococcus Aureus and Coagulase-Negative Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.

Sala M., et al., "Ambiguous Base Pairing of the Purine Analogue 1-(2-Deoxy-B-D -Ribofuranosyl)-Imidazole-4- Carboxamide During PCR," Nucleic Acids Research, 1996, vol. 24 (17), pp. 3302-3306.

Sambrook J., et al., "Molecular Cloning-A Laboratory Manual," 1989, Cold Spring Harbor Laboratory Press, Table of Contents.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Sampath R., et al., "Rapid Identification of Emerging Pathogens: Coronavirus," Emerging Infectious Diseases, 2005, vol. 11 (3), pp. 373-379.

Sanchez A., et al., "Detection and Molecular Characterization of Ebola Viruses Causing Disease in Human and Nonhuman Primates," Journal of Infectious Diseases, 1999, vol. 179 (1), pp. S164-S169.

Sanchez J.L., et al., "Epidemic of Adenovirus-Induced Respiratory Illness Among US Military Recruits: Epidemiologic and Immuno-logic Risk Factors in Healthy, Young adults," Jounal of Medical Virology, 2001, vol. 65 (4), pp. 710-718.

Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.

Santos S.R., et al., "Identification and Phylogenetic Sorting of Bacterial Lineages with Universally Conserved Genes and Proteins," Environmental Microbiology, 2004, vol. 6 (7), pp. 754-759.

Sarantis H., et al., "Comprehensive Detection and Serotyping of Human Adenoviruses by PCR and Sequencing," Journal of Clinical Microbiology, 2004, vol. 42 (9), pp. 3963-3969.

Sauer S., et al., "A Novel Procedure for Efficient Genotyping of Single Nucleotide Polymorphisms," Nucleic Acids Research, 2000, vol. 28 (5), pp. E13.1-E13.8.

Scaramozzino N., et al., "Comparison of Flavirus Universal Primer Pairs and Development of a rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Schena M., et al., "Genome Analysis with Gene Expression Microarrays," Bioessays, 1996, vol. 18 (5), pp. 427-431.

Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.

Schlecht N.F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a Marine Pikoplankton Community by 16s rRNA Gene cloning and Sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in Staphylococcus Aureus Isolates," Journal of Medical Microbiology, 1998, vol. 47 (4), pp. 335-340.

Schmitz, F.J., et al., "Development of Resistance to Ciprofloxacin, Rifampin, and Mupirocin in Methicillin-Susceptible and -Resistant Staphylococcus Aureus Isolates," Antimicrobial Agents and Chemotherapy, 2000, vol. 44 (11), pp. 3229-3231.

Schmitz F.J., et al., "Specific Information Concerning Taxonomu, Pathogenicity and Methicillin Esistance of Staphylococci Obtained by a Multiplex PCR," Journal of Medical Microbiology, 1997, vol. 46 (9), pp. 773-778.

Schram K.H., et al., "Mass Spectrometry of Nucleic Acid Components," Methods of Biochemical Analysis, 1990, vol. 34, pp. 203-280.

Schultz J.C., et al., "Polymerise Chain Reaction Products Analyzed by Charge Detection Mass Spectrometry," Rapid Communications in Mass Spectrometry, 1999, vol. 13 (10, pp. 15-20.

Schwartz M., et al., "Prenatal Diagnosis of Alpha-1-Antitrypsin Deficiency Using Polymerase Chainreaction (PCR), Compariosn of Conventional RFLP Methods with PCR used in Combination with Allelespecific Oligonucleotides or RFLP Analysis," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain REaction-Amplified DNA Fragments of Clostridium Botulinum Type E Neurotoxin Gene By High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomeleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillpmaviruses but Not That of Adenoviruses and Herpesviruses," Journal of Virology, 1994, vol. 68 (8), pp. 4785-4796.
Shaver Y.J, et al., "Restriction Fragment Length Polymorphism of rRNA Operons for Discrimination amd Intergenic Spacer Sequences for Cataloging of BACILUS Subtilis Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the Gene for Toxic Shock Syndrome Toxin 1 in Siaphylococcusaureus by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant Staphylococcus Aureus," Journal of Clinical Microbiology, 1994, vol. 32 (8), pp. 1866-1869.
Shresthna N.K., et al., "Rapid Identification of Staphylococcus Aureus and the MecA Gene from BacT/ALERT Blood Culture Bottles by USing the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 1818 (3), pp. 831-837.
Skov R.L., et al., "Evaluation of a New 3-h Hybridization Method for Detecting the MecA Gene in Staphylococcus Aureus and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a real-Time Reverse Transcriptase PCR Assay for Type A Influenzavirus and The Avian H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trahalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Strommenger B., et al., "Multiplex PCR Assay for Simultaneous Detection of Nine Clinically Relevant Antibiotic Resistance Genes in Staphylococcus Aureus," Journal of Clinical Microbiology, 2003, vol. 41 (9), pp. 4089-4094.
Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.
Sumner J.W., et al., "PCR Amplification and Comparison of Nucleotide Sequences from the groESL Heat Shock Operon of Ehrlichia Species," Journal of Critical Microbiology, 1997, vol. 35 (8), pp. 2087-2092.
Sundsfjord A., et al., "Genetic Methods for Detection of Antimicrobial Resistance," APMIS: Acta Pathologica, Microbiologica, et Immunologica Scandinavica, 2004, vol. 112 (11-12), pp. 815-837.
Supplementary European Search Report for Application No. 04775904.8, mailed on Jul. 7, 2008, 8 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary Partial European Search Report for Application No. EP02709785.6, mailed on Sep. 1, 2005, 5 pages.
Supplementary Partial European Search Report for Application No. EP05751872.2, mailed on Jan. 28, 2008, 8 pages.
Supplementary Partial European Search Report for Application No. EP05856582.1, mailed on Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection/Institut Pasteur, 2002, vol. 4 (13), pp. 1327-1333.
Swenson J.M., et al., "Performance of Eight Methods, Including Two New apid Methods, for Detection of Oxacillin Resistance in a Challenge Set of Staphylococcis Aureus Organisms," Journal of Clinical Microbiology, 2001, vol. 39 (10), pp. 3785-3788.
Takagaki Y., et al., "Four Factors are Required for 3—End Cleavage of Pre-mRNAs," Genes and Development, 1989, vol. 3 (11), pp. 1711-1724.
Takahashi H., et al., "Characterization of gryA, gryB, grlB Mutations in Fluoroquinolone—Resistant Clinical Isolates of Staphylococcus Aureus," The Journal of Antimicrobial Chemotherapy, 1998, vol. 41 (1), pp. 49-57.
Takahata M., et al., "Mutations in the GyrA and Gr1A Genes of Quinolone-Resistant Clinical Isolates of Methicillin-Resistant Staphylococcus Aureus," The Journal of Antimicrobial Chemotherapy, 1996, vol. 38 (3), pp. 543-546.
Takayama R., et al., "Quantificationof Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Talaat A.M., et al., "Gemone-Directed Primers for Selective Labeling of Bacterial Transcripts for DNA Microarray Analysis," Nature Biotechnolgy, 2000, vol. 17, pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant Staphylococcus Aureus Isolated in Fukushima Medical College Hospital," Fukushima Journal of Medical Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assistes Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Asspciated Methicillin-ResistantStaphylococcus Aureus Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Senstivity of Progrgessive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," THe Journal of the American Medical Association, 2004, vol. 292 (11), pp. 1333-1340.
Tokue Y., et al., "Comparison of a Polymerase Chain REaction Assay and a Conventional Microbiologic Method for Detection of Methicillin-Resistant Slaphylococcus Aureus," Antimocrobial Agents and Chemotherapy, 1992, vol. 36 (1), pp. 6-9.
Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.
Top F.H. Jr., "Control of Adenovirus Acute Respiratory Disease in U.S. Army Trainees," The Yale Journal of Biology and Medicine, 1975, vol. 43 (3), pp. 185-195.

Torroni A., et al., "Classification of European mtDNA from an Analysis of Three European Populations," Genetics, 1996, vol. 144 (4), pp. 1835-1850.

Towner K.J., et al., "Development and Evaluation of a PCR-Based Immunoassay for the Rapid Detection of Methicillin-Resistant Staphylococcus Aureus," Journal of Medical Microbiology, 1998, vol. 47 (7), pp. 607-613.

Tsuneyoshi T., et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in Staphylococcus Aureus Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistance Staphylococcus Aureus Expressing High-and Low-Level Mupirocin Resistance," Journal of Medical Microbiology, 2001, vol. 50 (10), pp. 909-915.

Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.

Unal S., et al., "Detection of Methicillin-Resistant Staphylococci by Using the Polymerase Chain Reaction," Journal of Clinical Microbiology, 1992, vol. 30 (7), pp. 1685-1691.

Upton A., et al., "Mupirocin and Staphylococcus Aureus: A Recent Paradigm of Emerging Antibiotic Resistance," The Journal of Antimicrobial Chemotherapy, 2003, vol. 51 (3), pp. 613-617.

Vabret A., et al., "Development of a PCR-an Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleotides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.

Van Der Vossen J.M., et al., "DNA Based Typing Identification and Detection Systems for Food Spoilage Microorganism: Development and Implementation," International Journal of Food Microbiology, 1996, vol. 33 (1), pp. 35-49.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame In-EncodedPart of Antervirus Replicase Is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The Brisitsh Journal of General Practic, 2001, vol. 51 (469), pp. 630-634.

Van Elden L.J., et al., "Simultaneos Detection of Influenza Viruses A and B Using Real-Time Quantitative PCR," Journal of Clinical Microbiology, 2001, vol. 39 (1), pp. 196-200.

Van Ert M.N., et al., "Mass Spectrometry Provides Accurate Characterization of Two Genetic Marker Types in Bacillus Anthracis," Bio Techniques, 2004, vol. 37 (4), pp. 642-651.

Van Leeuwen W.B., et al., "Multilocus Sequence Typing of Staphylococcus Aureus with DNA Array TEchnology," Journal of Clinical Microbiology, 2003, vol. 41 (7), pp. 3323-3326.

Van Leeuwen W.B., et al., "Rapid Detection of Methicillin-Resistance in Staphylococcus Aureus Isolates by the MRSA-Screen Latex Agglutination Test," Journal of Clinical Microbiology, 1999, vol. 37 (9), pp. 3029-3030.

Vanchiere J.A., et al., "Detection of BK Virus and Simian Virus 40 in the Urine of Healthy Children," Journal of Medical Virology, 2005, vol. 75 (3), pp. 447-454.

Vanderhallen H., et al., "Identification of Encephalomyocarditis Virus in Clinical Samples by Reverse Transcription-PCR Followed by genetic Typing Using Sequence Analysis," Journal of Clinical Microbiology, 1998, vol. 36 (12), pp. 3464-3467.

Vannuffel P., et al., "Rapid and Specific Molecular Identification of Methicillin-Resistant Staphylococcus Aureus in Endothracheal Aspirates from Mechanically Ventilated Patients," Journal of Clinical Microbiology, 1998, vol. 36 (8), pp. 2366-2368.

Vannuffel P., et al., "Specific Detection of Methicillin-Resistant Staphylococcus Species by Multiplex PCR," Journal of Clinical Microbiology, 1995, vol. 33 (11), pp. 2864-2867.

Verma S., et al., "Modified Oligonucleotides: Synthesis and Strategy for Users," Annual Review of Biochemistry, 1998, vol. 67, pp. 99-134.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.

Voelter C., et al., "Screening Human Tumor Samples with a Broad-Spectrum Polymerase Chain Reaction Method for the Detection of Polymaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infectious Due to Coagulase-Negative Staphylococci," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant Staphylococcus aureus Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Deecting Methicillin-Resistance in Staphylocicci," The Journal of Antimicrobial Chemotherapy, 1996, vol. 37 (5), pp. 901-909.

Walter J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: The gyrB Database for Identification and Classification of Bacteria," Nucleic Acids Research, 2001, vol. 29 (1), pp. 344-345.

Weissenbacher M., et al., "Etilogic and Clinical Evaluation of Acute Lower Respiratory TractInfections in Young Argentinean Children: An Overview," Reviews of Infectious Disease, 1990, vol. 12 (Suppl *), pp. S889-S898.

Welham K.J., et al., "The Characterization of Micro-Organisms by Matrix-Assised Laser Desorption/Lonization Time-of-Flight Mass Spectrometry," Rapid Communications in Mass Spectrometry, 1998, vol. 12 (4), pp. 176-180.

Wertheim H.F., et al., "Effect of Mupirocin Treatment on Nasal, Pharyngeal, and Perineal Carriage of Staphylococcus Aureus in Healthy Adults," Antimicrobial Agents and Chemotherapy, 2005, vol. 49 (4), pp. 1465-1467.

Westermann P., et al., "Inhibition of Expression of SV40 Virus Large T-Antigen by Antisense Oligodeoxyribonucleotides," Biomedica Biochemica Acta, 1989, vol. 1, pp. 85-93.

Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.

Wichelhaus T.A., et al., "Rapid Detection of Epidemic Starins of Methicillin-ResistantStaphylococcus Aureus," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "Rapid Identification of Bacterial by PCR-Single-Strand Confromation Polymorphism," Journal of Clinical Microbiology, 1994, vol. 32 (12), pp. 3002-3007.

Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4(&), pp. 566-577.

Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Enviromental Mass Spectrometry, 1987, vol. 14, pp. 111-116.

Woo T.H., et al., "Identification of Leptospira Inadai by Continuous Monitoring of Fluorescence during Rapid Cycle PCR," Systematic and Applied Microbiology, 1998, vol. 21 (1), pp. 89-96.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, mailed on May 15, 2006, 5 pages.

Wu S., et al., "Genetic Organization of the mecA Region in Methicillin-Susceptible and Methicillin-Resistant Starins of Staphylococcus Sciuri," The Journal of Bacteriology, 1998, vol. 180 (2), pp. 236-242.

Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.

Wunschel D., et al., "Discrimination Among the B. Cereus Group, in Comparison to B. Subtillis, by Structural Carbohydrate Profiles and Ribosomal RNA Spacer Region PCR," Systematic and Applied Microbiology, 1994, vol. 17, pp. 625-635.

Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.

Wunschel D.S., et al., "Heterogeneity in Bacillus Cereus PCR Products Detected by ESI-FTICR Mass Spectrometry," Analytical Chemistry, 1998, vol. 70 (6), pp. 1203-1207.

Wunshel D.S., et al., "Mass spectrometric characterization of DNA for molecular biological applications: advances using MALDI and ESI," Advances in Mass Spectrometry, 1998, vol. 14, Elsevier, pp. 377-406.

Xu L., et al., "Electrophore Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of HumanAdenovirus, 3, 7, and 21 by a Multiplex PCR Assay," Journal of Medical Virology, 2001, vol. 64 (4), pp. 537-542.

Xu X., et al., "Intercontinental Circulation of Human Influenza A(H1N2) Reassortant Viruses During the 2001-2002 Influenza Season," THe Journal of Infectious Diseases, 2002, vol. 186 (10), pp. 1490-1493.

Yao Z.P., et al., "Mass Spectrometry Based Proteolytic Mapping for Rapid Virus Identification," Analytical Chemistry, 2002, vol. 74 (11), pp. 2529-2534.

Yasui T., et al., "A Specific Oligonucleotide Primer Deection of Lactobacillus Lindneri by Polymerase Chain Reaction," Canadian Journal of Microbiology, 1997, vol. 43 (2), pp. 157-163.

Ye K., et al., "Three Distinct Promoters Direct Transcription of Different 5''Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphtyridone Antibiotic, Against Staphylococcus Aureus Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), pp. 1457-1468.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of Staphylococcus Aureus from Coagulase-Negative Staphylococci," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-Biofilm-Forming Staphylococcus Epidemidis Strain (ATCC 12228)," Molecular Microbiology, 2003, vol. 49 (6), pp. 1577-1593.

\* cited by examiner

SEQUENCE LISTING

<160> NUMBER OF SEQ ID NOS: 70

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
taggatggtg atatggttga tacaggcttt gg                          32

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ttcagatgtc tgtgtggcgg ccta                                   24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tcgggatgta atggctggtt                                        20

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
tcaggatggt ttttggtaga ggctatagt                              29

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
tagatgatag tgacattgca tataaatatg ca                          32

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tgacgaacca cagcgtcaca                                        20

<210> SEQ ID NO 7
<211> LENGTH: 28
<212> TYPE: DNA

<213> ORGANISM: Artificial Sequence
<220> FEATURE:
<223> OTHER INFORMATION: Primer

<400> SEQUENCE: 7
tacacacaat tccttggaag cacaggca         28

<210> SEQ ID NO 8
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: n is inosine

<400> SEQUENCE: 8
tactgttatn caggatggtg atatggt           27

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
tctgcaacca tttgcaaata atctggatat tt      32

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
tacatattca tccgtgctta caaccttaga         30

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
taccatgtcc gaacctgtat ctgt               24

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
tgcctgtgct tccaaggaat tgtgtgtaat a       31

<210> SEQ ID NO 13
<211> LENGTH: 28
<212> TYPE: DNA
<213> ORGANISM: Artificial Sequence
<220> FEATURE:
<223> OTHER INFORMATION: Primer

```
<400> SEQUENCE: 13
tttctgctcg tttataatgt ctacacat                                      28

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tgcacacaac ggacacacaa a                                             21

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
ttaggtcctg cacagccgca taatg                                         25

<210> SEQ ID NO 16
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is inosine

<400> SEQUENCE: 16
tctgcaacca tttgnaaata atctggatat tt                                 32

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
taggatggtg atatggttga tacaggcttt gg                                 32

<210> SEQ ID NO 18
<211> LENGTH: 32
<212> TYPE: DNA
<213> ORGANISM: Artificial Sequence
<220> FEATURE:
<223> OTHER INFORMATION: Primer

<400> SEQUENCE: 18
taggatggtg atatggttga tacaggcttt gg                                 32

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
taggatggtg atatggttga tacaggcttt gg                                 32
```

```
<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
taggatggtg atatggttga tacaggcttt gg                                    32

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
taggatggtg atatggttga tacaggcttt gg                                    32

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
taggatggtg atatggttga tacaggcttt gg                                    32

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
taggatggtg atatggttga tacaggcttt gg                                    32

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
taggatggtg atatggttga tacaggcttt gg                                    32

<210> SEQ ID NO 25
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (29)..(29)
<223> OTHER INFORMATION: n is inosine

<400> SEQUENCE: 25
taggatggtg atatggttga tacaggctnt gg                                    32

<210> SEQ ID NO 26
<211> LENGTH: 32
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (27)..(27)
<223> OTHER INFORMATION: n is inosine
<220> FEATURE:
<221> NAME/KEY: misc_feature
<222> LOCATION: (29)..(29)
<223> OTHER INFORMATION: n is inosine

<400> SEQUENCE: 26
taggatggtg atatggttga tacaggntnt gg                               32

<210> SEQ ID NO 27
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (27)..(27)
<223> OTHER INFORMATION: n is inosine
<220> FEATURE:
<221> NAME/KEY: misc_feature
<222> LOCATION: (29)..(29)
<223> OTHER INFORMATION: n is inosine

<400> SEQUENCE: 27
taggatggtg atatggttga tacnggntnt gg                               32

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
tactgttatt caggatggtg atatggt                                     27

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
tactgttatt caggatggtg atatggt                                     27

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
tactgttatt caggatggtg atatggt                                     27

<210> SEQ ID NO 31

<400> SEQUENCE: 31
```

000

<210> SEQ ID NO 32
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n is inosine

<400> SEQUENCE: 32
tactgttatt caggatgggng atatggt                                          27

<210> SEQ ID NO 33
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (19)..(19)
<223> OTHER INFORMATION: n is inosine

<400> SEQUENCE: 33
tactgttatn caggatgggng atatggt                                          27

<210> SEQ ID NO 34
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n is inosine

<400> SEQUENCE: 34
ttcagatgtc tgtgtggcng ccta                                              24

<210> SEQ ID NO 35
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (19)..(19)
<223> OTHER INFORMATION: n is inosine

<400> SEQUENCE: 35
ttcagatgtc tntgtggcng ccta                                              24

<210> SEQ ID NO 36
<211> LENGTH: 28
<212> TYPE: DNA
<213> ORGANISM: Artificial Sequence

```
<220> FEATURE:
<223> OTHER INFORMATION: Primer

<400> SEQUENCE: 36
tggaaatcct ttttctcaag gacgtggt                                              28

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
tggaaatcct ttttctcaag gacgtggt                                              28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
tggaaatcct ttttctcaag gacgtggt                                              28

<210> SEQ ID NO 39
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (17)..(17)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 39
tagatgatag tganatngca tatnaatatg ca                                         32

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
tatggtgcag tgggcatttg ataatg                                                26

<210> SEQ ID NO 41
<211> LENGTH: 26
<212> TYPE: DNA
<213> ORGANISM: Artificial Sequence
<220> FEATURE:
<223> OTHER INFORMATION: Primer

<400> SEQUENCE: 41
tatggtgcag tgggcatttg ataatg                                                26
```

```
<210> SEQ ID NO 42
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is inosine

<400> SEQUENCE: 42
tatggtgcag tgggcatntg ataatg                                              26

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
tatggtgcag tgggcatttg ataatg                                              26

<210> SEQ ID NO 44
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(33)
<223> OTHER INFORMATION: n is inosine

<400> SEQUENCE: 44
tctgcaacca tttgcaaata atctggatat ttnca                                    35

<210> SEQ ID NO 45
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (33)..(33)
<223> OTHER INFORMATION: n is inosine

<400> SEQUENCE: 45
tctgcaacca tttgnaaata atctggatat ttnca                                    35

<210> SEQ ID NO 46
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine
<220> FEATURE:
<221> NAME/KEY: misc_feature
<222> LOCATION: (33)..(33)
<223> OTHER INFORMATION: n is inosine

<400> SEQUENCE: 46
```
tctgcaacca tttnnaaata atctggatat ttnca                       35

<210> SEQ ID NO 47
<211> LENGTH: 32
<212> TYPE: DNA
<213> ORGANISM: Artificial Sequence
<220> FEATURE:
<223> OTHER INFORMATION: Primer

<400> SEQUENCE: 47
tctgcaacca tttgaaaata atctggatat tt                          32

<210> SEQ ID NO 48
<211> LENGTH: 32
<212> TYPE: DNA
<213> ORGANISM: Artificial Sequence
<220> FEATURE:
<223> OTHER INFORMATION: Primer

<400> SEQUENCE: 48
tctgcaacca tttgaaaata atctggatat tt                          32

<210> SEQ ID NO 49
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is inosine

<400> SEQUENCE: 49
tctgcaacca tttgnaaata atctggatat tt                          32

<210> SEQ ID NO 50
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine

<400> SEQUENCE: 50
tctgcaacca tttnnaaata atctggatat tt                          32

<210> SEQ ID NO 51
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine
<220> FEATURE:
<221> NAME/KEY: misc_feature
<222> LOCATION: (17)..(17)
<223> OTHER INFORMATION: n is inosine

<400> SEQUENCE: 51
tctgcaacca tttnnanata atctggatat tt                          32

```
<210> SEQ ID NO 52
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is inosine

<400> SEQUENCE: 52
tctgcaacca tttgnaaata atctggatat tt                                  32

<210> SEQ ID NO 53
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine

<400> SEQUENCE: 53
tctgcaacca tttnnaaata atctggatat tt                                  32

<210> SEQ ID NO 54
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine
<220> FEATURE:
<221> NAME/KEY: misc_feature
<222> LOCATION: (17)..(17)
<223> OTHER INFORMATION: n is inosine

<400> SEQUENCE: 54
tctgcaacca tttnnanata atctggatat tt                                  32

<210> SEQ ID NO 55
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is inosine

<400> SEQUENCE: 55
tctgcaacca tttgnaaata atctggatat tt                                  32

<210> SEQ ID NO 56
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine

<400> SEQUENCE: 56
```
tctgcaacca tttnnaaata atctggatat tt                                    32

<210> SEQ ID NO 57
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine
<220> FEATURE:
<221> NAME/KEY: misc_feature
<222> LOCATION: (17)..(17)
<223> OTHER INFORMATION: n is inosine

<400> SEQUENCE: 57
tctgcaacca tttnnanata atctggatat tt                                    32

<210> SEQ ID NO 58

<400> SEQUENCE: 58

000

<210> SEQ ID NO 59
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine

<400> SEQUENCE: 59
tctgcaacca tttnnaaata atctggatat tt                                    32

<210> SEQ ID NO 60
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is inosine
<220> FEATURE:
<221> NAME/KEY: misc_feature
<222> LOCATION: (17)..(17)
<223> OTHER INFORMATION: n is inosine

<400> SEQUENCE: 60
tctgcaacca tttnnanata atctggatat tt                                    32

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
tacatattca tccgtgctta caaccttaga                                       30

<210> SEQ ID NO 62

-continued

```
<211> LENGTH: 30
<212> TYPE: DNA
<213> ORGANISM: Artificial Sequence
<220> FEATURE:
<223> OTHER INFORMATION: Primer

<400> SEQUENCE: 62
tacatattca tccgtgctta caaccttaga                                            30

<210> SEQ ID NO 63
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is inosine

<400> SEQUENCE: 63
tagtattttg tcctgccacn catttaaacg                                            30

<210> SEQ ID NO 64
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: n is inosine

<400> SEQUENCE: 64
tagtattttg tcctgccann catttaaacg                                            30

<210> SEQ ID NO 65
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(20)
<223> OTHER INFORMATION: n is inosine

<400> SEQUENCE: 65
tagtattttg tcctgccnnn catttaaacg                                            30

<210> SEQ ID NO 66
<211> LENGTH: 28
<212> TYPE: DNA
<213> ORGANISM: Artificial Sequence
<220> FEATURE:
<223> OTHER INFORMATION: Primer

<400> SEQUENCE: 66
tttctgctcg tttataatgt ctacacat                                              28

<210> SEQ ID NO 67
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(21)
```

```
<223> OTHER INFORMATION: n is inosine

<400> SEQUENCE: 67
ttgcttttta aaaatgcagn ngcatt                                        26

<210> SEQ ID NO 68
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(21)
<223> OTHER INFORMATION: n is inosine

<400> SEQUENCE: 68
ttgcttttta aaaatgcnnn ngcatt                                        26

<210> SEQ ID NO 69
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(21)
<223> OTHER INFORMATION: n is inosine

<400> SEQUENCE: 69
ttgcttttta aaaatgcagn ngcatt                                        26

<210> SEQ ID NO 70
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(13)
<223> OTHER INFORMATION: n is inosine
<220> FEATURE:
<221> NAME/KEY: misc_feature
<222> LOCATION: (20)..(20)
<223> OTHER INFORMATION: n is inosine

<400> SEQUENCE: 70
tatttgcctg cnnattgctn tttaaaaa                                      28
```

COMPOSITIONS FOR USE IN IDENTIFICATION OF PAPILLOMAVIRUS

CROSS REFERENCE TO RELATED PATENT APPLICATIONS

The present application claims the benefit of priority to U.S. Provisional Application No. 61/102,324, filed Oct. 2, 2008 and is further a continuation-in-part of U.S. patent application Ser. No. 11/368,233, filed Mar. 3, 2006 (now abandoned), which claims the benefit of priority to U.S. Provisional Application Nos. 60/658,248, filed Mar. 3, 2005, 60/705,631, filed Aug. 3, 2005, 60/732,539, filed Nov. 1, 2005, and 60/740,617, filed Nov. 28, 2005, which are each incorporated by reference in their entirety.

STATEMENT OF GOVERNMENT SUPPORT

This invention was made with United States government support under NIH/NIAID contract No. N01 A140100 awarded by the National Institutes of Health. The United States government has certain rights in the invention.

SEQUENCE LISTING

The instant application contains a Sequence Listing which has been submitted via EFS-Web and is hereby incorporated by reference in its entirety. Said ASCII copy, is named DIBIS0106USP1 SequenceListing.txt, and is 16 kilobytes in size.

FIELD OF THE INVENTION

The present invention relates generally to identification of Human papillomavirus (HPV), and provides methods, compositions and kits useful for this purpose when combined, for example, with molecular mass or base composition analysis.

BACKGROUND OF THE INVENTION

Papillomaviruses are a diverse group of DNA-based viruses that infect the skin and mucous membranes of humans and a variety of animals. Approximately 130 HPV types have been identified. About 30-40 HPV types are typically transmitted through sexual contact and infect the anogenital region. Different HPV types are associated with different pathological risks. Some HPV types result in latent infection, while some can cause warts, and others may cause a subclinical infection resulting in precancerous lesions. Persistent infection with a "high-risk" subset of sexually transmitted HPV may lead to potentially precancerous lesions and can progress to invasive cancer. HPV infection is a necessary factor in the development of nearly all cases of cervical cancer.

SUMMARY OF THE INVENTION

The present invention relates generally to detection and identification of HPV, and provides methods, compositions and kits useful for this purpose when combined, for example, with molecular mass or base composition analysis. However, the compositions and methods find use in a variety of biological sample analysis techniques and are not limited to processes that employ or require molecular mass or base composition analysis. For example, primers described herein find use in a variety of research, surveillance, and diagnostic approaches that utilize one or more primers, including a variety of approaches that employ the polymerase chain reaction.

Ito further illustrate, in certain embodiments, the invention for the rapid detection and characterization of papillomavirus. In some embodiments the present invention provides a composition comprising at least one purified oligonucleotide primer pair that comprises forward and reverse primers, wherein said primer pair comprises nucleic acid sequences that are substantially complementary to nucleic acid sequences of two or more different bioagents belonging to the Papillomaviridae family, wherein the primer pair is configured to produce amplicons comprising different base compositions that correspond to the two or more different bioagents. In addition to compositions and kits that include one or more of the primer pairs described herein, the invention also relates to methods and systems.

In one aspect, the present invention provides compositions comprising at least one purified oligonucleotide primer pair that comprises forward and reverse primers about 15 to 35 nucleobases in length, wherein the forward primer comprises at least 70% identity (e.g., 70% . . . 75% . . . 90% . . . 95% . . . 100%) with a sequence selected from SEQ ID NOs: 1-8 and 17-43, and wherein the reverse primer comprises at least 70% identity (e.g., 70% . . . 75% . . . 90% . . . 95% . . . 100%) with a sequence selected from SEQ ID NOs: 9-16 and 44-70. Typically, the primer pair is configured to hybridize with HPV nucleic acids. In further embodiments, the primer pair is selected from the group of primer pair sequences consisting of: SEQ ID NOS: 1: 9, 2: 10, 3: 11, 4: 12, 5: 13, 6: 14, 7: 15, 8: 16, 17:44, 18:45, 19:46, 20:47, 21:48, 22:49, 23:50, 24:51, 25:52, 26:53, 27:54, 28:55, 29:56, 30:57, 31:58, 32:59, 33:60, 34:61, 35:62, 36:63, 37:64, 38:65, 39:66, 40:67, 41:68, 42:69, and 43:70. In certain embodiments, the forward and/or reverse primer has a base length selected from the group consisting of: 15, 16, 17, 18, 19, 20, 21, 22, 23, 24, 25, 26, 27, 28, 29, 30, 31, 32, 33, 34, or 34 nucleotides, although both shorter and longer primers may be used.

In another aspect, the invention provides a purified oligonucleotide primer pair, comprising a forward primer and a reverse primer that each independently comprise 14 to 40 consecutive nucleobases selected from the primer pair sequences shown in Table 1 and/or Table 2, which primer pair is configured to generate an amplicon between about 50 and 150 consecutive nucleobases in length.

In another aspect, the invention provides a kit comprising at least one purified oligonucleotide primer pair that comprises forward and reverse primers that are about 20 to 35 nucleobases in length, and wherein the forward primer comprises at least 70%, at least 80%, at least 90%, at least 95%, or at least 100% sequence identity with a sequence selected from the group consisting of SEQ ID NOS: 1-8 and 17-43, and the reverse primer comprises at least 70% sequence identity (e.g., 75%, 85%, or 95%) with a sequence selected from the group consisting of SEQ ID NOS: 9-16 and 44-70. In some embodiments, the kit comprises a primer pair that is a broad range survey primer pair (e.g., specific for nucleic acid of a housekeeping gene found in many or all members of a category of organism).

In other embodiments, the amplicons produced with the primers are 45 to 200 nucleobases in length (e.g., 45 . . . 75 . . . 125 . . . 175 . . . 200). In some embodiments, a non-templated T residue on the 5'-end of said forward and/or reverse primer is removed. In still other embodiments, the forward and/or reverse primer further comprises a non-templated T residue on the 5'-end. In additional embodiments, the forward and/or reverse primer comprises at least one molecular mass modifying tag. In some embodiments, the forward and/or reverse primer comprises at least one modified nucleobase. In further embodiments, the modified nucleobase is 5-propynyluracil or 5-propynylcytosine. In other embodiments, the modified nucleobase is a mass modified nucleobase. In still other embodiments, the mass modified nucleobase is 5-Iodo-C. In additional embodiments, the modified nucleobase is a universal nucleobase. In some embodiments, the universal nucleobase is inosine. In certain embodiments, kits comprise the compositions described herein.

In particular embodiments, the present invention provides methods of determining a presence of an HPV in at least one sample, the method comprising: (a) amplifying one or more (e.g., two or more, three or more, four or more, etc.; one to two, one to three, one to four, etc.; two, three, four, etc.) segments of at least one nucleic acid from the sample using at least one purified oligonucleotide primer pair that comprises forward and reverse primers that are about 20 to 35 nucleobases in length, and wherein the forward primer comprises at least 70% (e.g., 70% ... 75% ... 90% ... 95% ... 100%) sequence identity with a sequence selected from the group consisting of SEQ ID NOs: 1-8 and 17-43, and the reverse primer comprises at least 70% (e.g., 70% ... 75% ... 90% ... 95% ... 100%) sequence identity with a sequence selected from the group consisting of SEQ ID NOs: 9-16 and 44-70 to produce at least one amplification product; and (b) detecting the amplification product, thereby determining the presence of the HPV in the sample.

In certain embodiments, step (b) comprises determining an amount of the HPV in the sample. In further embodiments, step (b) comprises detecting a molecular mass of the amplification product. In other embodiments, step (b) comprises determining a base composition of the amplification product, wherein the base composition identifies the number of A residues, C residues, T residues, G residues, U residues, analogs thereof and/or mass tag residues thereof in the amplification product, whereby the base composition indicates the presence of the HPV in the sample or identifies the pathogenicity of the HPV in the sample. In particular embodiments, the methods further comprise comparing the base composition of the amplification product to calculated or measured base compositions of amplification products of one or more known HPV present in a database, for example, with the proviso that sequencing of the amplification product is not used to indicate the presence of or to identify the HPV, wherein a match between the determined base composition and the calculated or measured base composition in the database indicates the presence of or identifies the HPV. In some embodiments, the identification of HPV is at the biological kingdom level, phylum level, class level, order level, family level, genus level, species level, sub-type level (e.g., stain level), genotype level, or individual identity level.

In some embodiments, the present invention provides methods of identifying one or more HPV bioagents in a sample, the method comprising: amplifying two or more segments of a nucleic acid from the one or more HPV bioagents in the sample with two or more oligonucleotide primer pairs to obtain two or more amplification products (e.g., from a single bioagent); (b) determining two or more molecular masses and/or base compositions of the two or more amplification products; and (c) comparing the two or more molecular masses and/or the base compositions of the two or more amplification products with known molecular masses and/or known base compositions of amplification products of known HPV bioagents produced with the two or more primer pairs to identify the one or more HPV bioagents in the sample. In certain embodiments, the methods comprise identifying the one or more HPV bioagents in the sample using three, four, five, six, seven, eight or more primer pairs. In other embodiments, the one or more HPV bioagents in the sample cannot be identified using a single primer pair of the two or more primer pairs. In particular embodiments, the methods comprise obtaining the two or more molecular masses of the two or more amplification products via mass spectrometry. In certain embodiments, the methods comprise calculating the two or more base compositions from the two or more molecular masses of the two or more amplification products. In some embodiments, the HPV bioagents are selected from the group consisting of a HPV genus, a species thereof, a sub-species thereof, and combinations thereof.

In some embodiments, the present invention provides methods of identifying one or more strains of HPV in a sample, the method comprising: (a) amplifying two or more segments of a nucleic acid from the one or more HPV in the sample with first and second oligonucleotide primer pairs to obtain two or more amplification products, wherein the first primer pair is a broad range survey primer pair, and wherein the second primer pair produces an amplicon that reveals species, sub-type, strain, or genotype-specific information; (b) determining two or more molecular masses and/or base compositions of the two or more amplification products; and (c) comparing the two or more molecular masses and/or the base compositions of the two or more amplification products with known molecular masses and/or known base compositions of amplification products of known HPV produced with the first and second primer pairs to identify the HPV in the sample. In some embodiments, the second primer pair amplifies a portion of a gene from HPV.

In certain embodiments, the second primer pair comprises forward and reverse primers that are about 20 to 35 nucleobases in length, and wherein the forward primer comprises at least 70% sequence identity with a sequence selected from the group consisting of SEQ ID NOs: 1-8 and 17-43, and the reverse primer comprises at least 70% sequence identity with a sequence selected from the group consisting of SEQ ID NOs: 9-16 and 44-70 to produce at least one amplification product. In further embodiments, the obtaining the two or more molecular masses of the two or more amplification products is via mass spectrometry. In some embodiments, the methods comprise calculating the two or more base compositions from the two or more molecular masses of the two or more amplification products. In further embodiments, the HPV is selected from the group consisting of: the family Papillomaviridae, the genus Alphapapillomavirus, the genus Betapapillomavirus, the genus Gammapapillomavirus, the genus Mupapillomavirus, and the genus Nupapillomavirus.

In some embodiments, the second primer pair is selected from the group of primer pair sequences consisting of: SEQ ID NOS: 1: 9, 2: 10, 3: 11, 4: 12, 5: 13, 6: 14, 7: 15, 8: 16, 17:44, 18:45, 19:46, 20:47, 21:48, 22:49, 23:50, 24:51, 25:52, 26:53, 27:54, 28:55, 29:56, 30:57, 31:58, 32:59, 33:60, 34:61, 35:62, 36:63, 37:64, 38:65, 39:66, 40:67, 41:68, 42:69, and 43:70. In other embodiments, the determining the two or more molecular masses and/or base compositions is conducted without sequencing the two or more amplification products. In certain embodiments, the HPV in the sample cannot be identified using a single primer pair of the first and second primer pairs. In other embodiments, the HPV in the sample is identified by comparing three or more molecular masses and/or base compositions of three or more amplification products with a database of known molecular masses and/or known base compositions of amplification products of known HPV produced with the first and second primer pairs, and a third primer pair.

In further embodiments, members of the first and second primer pairs hybridize to conserved regions of the nucleic acid that flank a variable region. In some embodiments, the variable region varies between at least two species of HPV. In particular embodiments, the variable region uniquely varies between at least two (e.g., 3, 4, 5, 6, 7, 8, 9, 10, . . . , 20, etc.) genuses, species, sub-types, strains, or genotypes of HPV.

In some embodiments, the present invention provides systems comprising: (a) a mass spectrometer configured to detect one or more molecular masses of amplicons produced using at least one purified oligonucleotide primer pair that comprises forward and reverse primers about 15 to 35 nucleobases in length, wherein the forward primer comprises at least 70% (e.g., 70% . . . 75% . . . 90% . . . 95% . . . 100%) identity with a sequence selected from SEQ ID NOs: 1-8 and 17-43, and wherein the reverse primer comprises at least 70% (e.g., 70% . . . 75% . . . 90% . . . 95% . . . 100%) identity with a sequence selected from SEQ ID NOs: 9-16 and 44-70; and (b) a controller operably connected to the mass spectrometer, the controller configured to correlate the molecular masses of the amplicons with one or more species of HPV identities. In certain embodiments, the second primer pair is selected from the group of primer pair sequences consisting of: SEQ ID NOS: 1: 9, 2: 10, 3: 11, 4: 12, 5: 13, 6: 14, 7: 15, 8: 16, 17:44, 18:45, 19:46, 20:47, 21:48, 22:49, 23:50, 24:51, 25:52, 26:53, 27:54, 28:55, 29:56, 30:57, 31:58, 32:59, 33:60, 34:61, 35:62, 36:63, 37:64, 38:65, 39:66, 40:67, 41:68, 42:69, and 43:70. In other embodiments, the controller is configured to determine base compositions of the amplicons from the molecular masses of the amplicons, which base compositions correspond to the one or more species of HPV. In particular embodiments, the controller comprises or is operably connected to a database of known molecular masses and/or known base compositions of amplicons of known species of HPV produced with the primer pair.

In certain embodiments, the database comprises molecular mass information for at least three different bioagents. In other embodiments, the database comprises molecular mass information for at least 2 . . . 10 . . . 50 . . . 100 . . . 1000 . . . 10,000, or 100,000 different bioagents. In particular embodiments, the molecular mass information comprises base composition data. In some embodiments, the base composition data comprises at least 10 . . . 50 . . . 100 . . . 500 . . . 1000 . . . 1000 . . . 10,000 . . . or 100,000 unique base compositions. In other embodiments, the database comprises molecular mass information for a bioagent from two or more genuses selected from the group consisting of, but not limited to alphapapillomavirus, betapapillomavirus, gammapapillomavirus. mupapillomavirus, and nupapillomavirus. In some embodiments, the database comprises molecular mass information for a bioagent from each of the genuses alphapapillomavirus, betapapillomavirus, gammapapillomavirus, mupapillomavirus, nupapillomavirus. In further embodiments, the database comprises molecular mass information for a HPV bioagent. In further embodiments, the database is stored on a local computer. In particular embodiments, the database is accessed from a remote computer over a network. In further embodiments, the molecular mass in the database is associated with bioagent identity. In certain embodiments, the molecular mass in the database is associated with bioagent geographic origin. In particular embodiments, bioagent identification comprises interrogation of the database with two or more different molecular masses (e.g., 2, 3, 4, 5, . . . 10 . . . 25 or more molecular masses) associated with the bioagent.

In some embodiments, the present invention provides compositions comprising at least one purified oligonucleotide primer 15 to 35 nucleobases in length, wherein the oligonucleotide primer comprises at least 70% (e.g., 70% . . . 75% . . . 90% . . . 95% . . . 100%) identity with a sequence selected from SEQ ID NOs: 1-16 and 17-70.

BRIEF DESCRIPTION OF THE DRAWINGS

The foregoing summary and detailed description is better understood when read in conjunction with the accompanying drawings which are included by way of example and not by way of limitation.

DETAILED DESCRIPTION OF EMBODIMENTS

Figure 1:
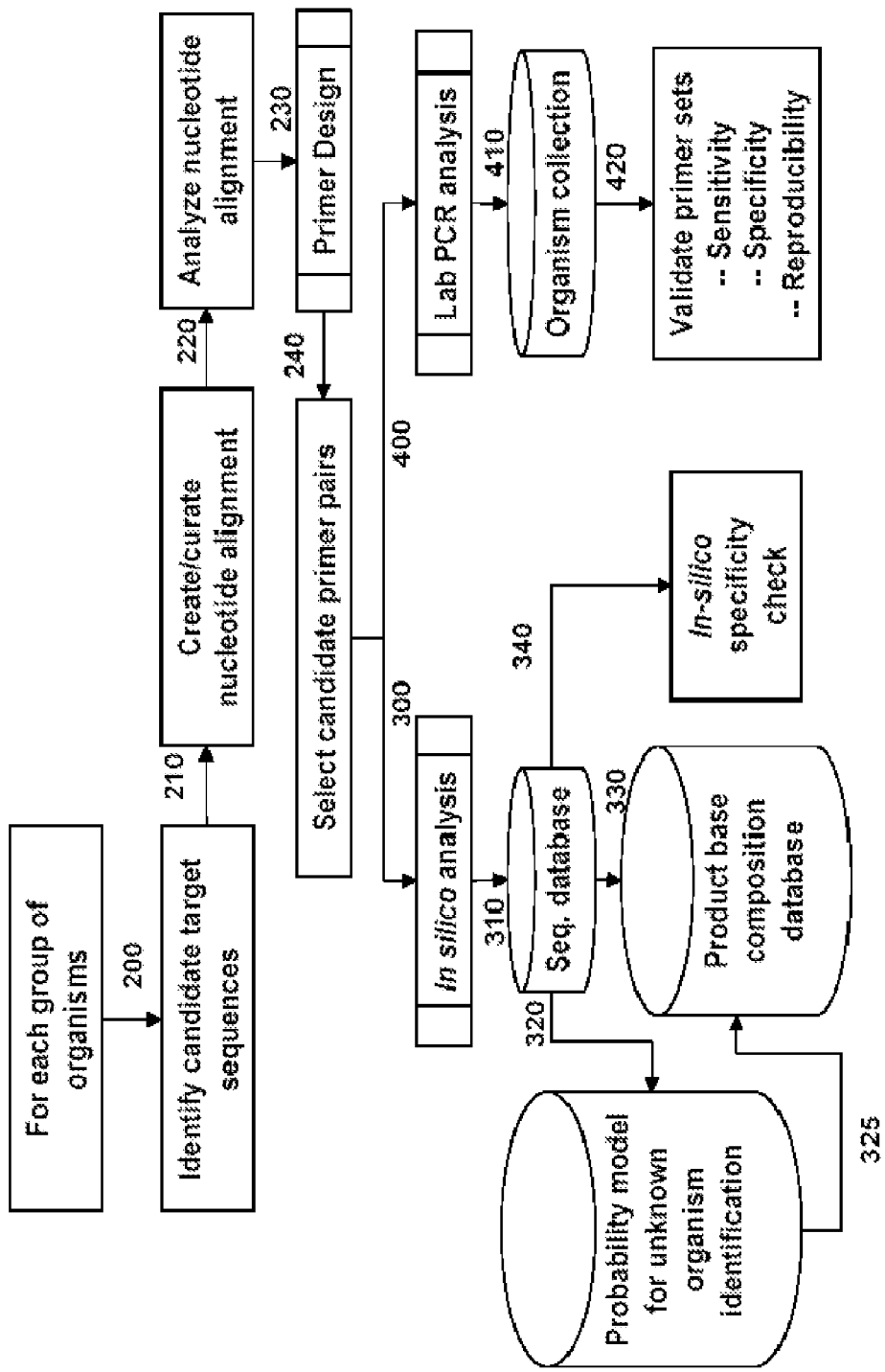
FIG. 1 shows a process diagram illustrating one embodiment of the primer pair selection process.

It is to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

As used herein, the term "about" means encompassing plus or minus 10%. For example, about 200 nucleotides refers to a range encompassing between 180 and 220 nucleotides.

As used herein, the term "amplicon" or "bioagent identifying amplicon" refers to a nucleic acid generated using the primer pairs described herein. The amplicon is typically double stranded DNA; however, it may be RNA and/or DNA: RNA. In some embodiments, the amplicon comprises DNA complementary to HPV RNA, DNA, or cDNA. In some embodiments, the amplicon comprises sequences of conserved regions/primer pairs and intervening variable region. As discussed herein, primer pairs are configured to generate amplicons from HPV nucleic acid. As such, the base composition of any given amplicon may include the primer pair, the complement of the primer pair, the conserved regions and the variable region from the bioagent that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used to generate the molecular mass data. Generally, the amplicon further comprises a length that is compatible with mass spectrometry analysis. Bioagent identifying amplicons generate base compositions that are preferably unique to the identity of a bioagent (e.g., HPV).

Amplicons typically comprise from about 45 to about 200 consecutive nucleobases (i.e., from about 45 to about 200 linked nucleosides). One of ordinary skill in the art will appreciate that this range expressly embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length. One of ordinary skill in the art will further appreciate that the above range is not an absolute limit to the length of an amplicon, but instead represents a preferred length range. Amplicon lengths falling outside of this range are also included herein so long as the amplicon is amenable to calculation of a base composition signature as herein described.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

As used herein, the term "base composition" refers to the number of each residue comprised in an amplicon or other nucleic acid, without consideration for the linear arrangement of these residues in the strand(s) of the amplicon. The amplicon residues comprise, adenosine (A), guanosine (G), cytidine, (C), (deoxy)thymidine (T), uracil (U), inosine (I), nitroindoles such as 5-nitroindole or 3-nitropyrrole, dP or dK (Hill F et al. Polymerase recognition of synthetic oligodeoxyribonucleotides incorporating degenerate pyrimidine and purine bases. *Proc Natl Acad Sci USA*. 1998 Apr. 14; 95(8): 4258-63), an acyclic nucleoside analog containing 5-nitroindazole (Van Aerschot et al., *Nucleosides and Nucleotides,* 1995, 14, 1053-1056), the purine analog 1-(2-deoxy-beta-D-ribofuranosyl)-imidazole-4-carboxamide, 2,6-diaminopurine, 5-propynyluracil, 5-propynylcytosine, phenoxazines, including G-clamp, 5-propynyl deoxy-cytidine, deoxy-thymidine nucleotides, 5-propynylcytidine, 5-propynyluridine and mass tag modified versions thereof, including 7-deaza-2'-deoxyadenosine-5'-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$. In some embodiments, the non-natural nucleosides used herein include 5-propynyluracil, 5-propynylcytosine and inosine. Herein the base composition for an unmodified DNA amplicon is notated as $A_wG_xC_yT_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon. Base compositions are calculated from a molecular mass measurement of an amplicon, as described below. The calculated base composition for any given amplicon is then compared to a database of base compositions. A match between the calculated base composition and a single database entry reveals the identity of the bioagent.

As used herein, a "base composition probability cloud" is a representation of the diversity in base composition resulting from a variation in sequence that occurs among different isolates of a given species, family or genus. Base composition calculations for a plurality of amplicons are mapped on a pseudo four-dimensional plot. Related members in a family, genus or species typically cluster within this plot, forming a base composition probability cloud.

As used herein, the term "base composition signature" refers to the base composition generated by any one particular amplicon.

As used herein, a "bioagent" means any biological organism or component thereof or a sample containing a biological organism or component thereof, including microorganisms or infectious substances, or any naturally occurring, bioengineered or synthesized component of any such microorganism or infectious substance or any nucleic acid derived from any such microorganism or infectious substance. Those of ordinary skill in the art will understand fully what is meant by the term bioagent given the instant disclosure. Still, a non-exhaustive list of bioagents includes: cells, cell lines, human clinical samples, mammalian blood samples, cell cultures, bacterial cells, viruses, viroids, fungi, protists, parasites, rickettsiae, protozoa, animals, mammals or humans. Samples may be alive, non-replicating or dead or in a vegetative state (for example, vegetative bacteria or spores). Preferably, the bioagent is an HPV such as Alphapapillomavirus or Gammapapillomavirus.

As used herein, a "bioagent division" is defined as group of bioagents above the species level and includes but is not limited to, orders, families, genus, classes, clades, genera or other such groupings of bioagents above the species level.

As used herein, "broad range survey primers" are primers designed to identify an unknown bioagent as a member of a particular biological division (e.g., an order, family, class, Glade, or genus). However, in some cases the broad range survey primers are also able to identify unknown bioagents at the species or sub-species level. As used herein, "division-wide primers" are primers designed to identify a bioagent at the species level and "drill-down" primers are primers designed to identify a bioagent at the sub-species level. As used herein, the "sub-species" level of identification includes, but is not limited to, strains, subtypes, variants, and isolates. Drill-down primers are not always required for identification at the sub-species level because broad range survey intelligent primers may, in some cases provide sufficient identification resolution to accomplishing this identification objective.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "conserved region" in the context of nucleic acids refers to a nucleobase sequence (e.g., a subsequence of a nucleic acid, etc.) that is the same or similar in two or more different regions or segments of a given nucleic acid molecule (e.g., an intramolecular conserved region), or that is the same or similar in two or more different nucleic acid molecules (e.g., an intermolecular conserved region). To illustrate, a conserved region may be present in two or more different taxonomic ranks (e.g., two or more different genera, two or more different species, two or more different subspecies, and the like) or in two or more different nucleic acid molecules from the same organism.

To further illustrate, in certain embodiments, nucleic acids comprising at least one conserved region typically have between about 70%-100%, between about 80-100%, between about 90-100%, between about 95-100%, or between about 99-100% sequence identity in that conserved region. A conserved region may also be selected or identified functionally as a region that permits generation of amplicons via primer extension through hybridization of a completely or partially complementary primer to the conserved region for each of the target sequences to which conserved region is conserved.

The term "correlates" refers to establishing a relationship between two or more things. In certain embodiments, for example, detected molecular masses of one or more amplicons indicate the presence or identity of a given bioagent in a sample. In some embodiments, base compositions are calculated or otherwise determined from the detected molecular masses of amplicons, which base compositions indicate the presence or identity of a given bioagent in a sample.

As used herein, in some embodiments the term "database" is used to refer to a collection of base composition molecular mass data. In other embodiments the term "database" is used to refer to a collection of base composition data. The base composition data in the database is indexed to bioagents and to primer pairs. The base composition data reported in the database comprises the number of each nucleoside in an amplicon that would be generated for each bioagent using each primer. The database can be populated by empirical data. In this aspect of populating the database, a bioagent is selected and a primer pair is used to generate an amplicon. The amplicon's molecular mass is determined using a mass spectrometer and the base composition calculated therefrom without sequencing i.e., without determining the linear sequence of nucleobases comprising the amplicon. Note that base composition entries in the database may be derived from sequencing data (i.e., known sequence information), but the base composition of the amplicon to be identified is determined without sequencing the amplicon. An entry in the database is made to associate correlate the base composition with the bioagent and the primer pair used. The database may also be populated using other databases comprising bioagent information. For example, using the GenBank database it is possible to perform electronic PCR using an electronic representation of a primer pair. This in silico method may provide the base composition for any or all selected bioagent(s) stored in the GenBank database. The information may then be used to populate the base composition database as described above. A base composition database can be in silico, a written table, a reference book, a spreadsheet or any form generally amenable to databases. Preferably, it is in silico on computer readable media.

The term "detect", "detecting" or "detection" refers to an act of determining the existence or presence of one or more targets (e.g., bioagent nucleic acids, amplicons, etc.) in a sample.

As used herein, the term "etiology" refers to the causes or origins, of diseases or abnormal physiological conditions.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length sequence or fragment thereof are retained.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to nucleic acid sequences that are not found naturally associated with the gene sequences in the chromosome or are associated with portions of the chromosome not found in nature (e.g., genes expressed in loci where the gene is not normally expressed).

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. In context of the present invention, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated as Plus/Plus. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" or "core viral gene" refers to a gene encoding a protein or RNA involved in basic functions required for survival and reproduction of a bioagent. Housekeeping genes include, but are not limited to, genes encoding RNA or proteins involved in translation, replication, recombination and repair, transcription, nucleotide metabolism, amino acid metabolism, lipid metabolism, energy generation, uptake, secretion and the like.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_m$) of the formed hybrid, and the G:C ratio within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, "intelligent primers" or "primers" or "primer pairs," in some embodiments, are oligonucleotides that are designed to bind to conserved sequence regions of one or more bioagent nucleic acids to generate bioagent identifying amplicons. In some embodiments, the bound primers flank an intervening variable region between the conserved binding sequences. Upon amplification, the primer pairs yield amplicons e.g., amplification products that provide base composition variability between the two or more bioagents. The variability of the base compositions allows for the identification of one or more individual bioagents from, e.g., two or more bioagents based on the base composition distinctions. In some embodiments, the primer pairs are also configured to generate amplicons amenable to molecular mass analysis. Further, the sequences of the primer members of the primer pairs are not necessarily fully complementary to the conserved region of the reference bioagent. For example, in some embodiments, the sequences are designed to be "best fit" amongst a plurality of bioagents at these conserved binding sequences. Therefore, the primer members of the primer pairs have substantial complementarity with the conserved regions of the bioagents, including the reference bioagent.

In some embodiments of the invention, the oligonucleotide primer pairs described herein can be purified. As used herein, "purified oligonucleotide primer pair," "purified primer pair," or "purified" means an oligonucleotide primer pair that is chemically-synthesized to have a specific sequence and a specific number of linked nucleosides. This term is meant to explicitly exclude nucleotides that are generated at random to yield a mixture of several compounds of the same length each with randomly generated sequence. As used herein, the term "purified" or "to purify" refers to the removal of one or more components (e.g., contaminants) from a sample.

As used herein, the term "molecular mass" refers to the mass of a compound as determined using mass spectrometry, for example, ESI-MS. Herein, the compound is preferably a nucleic acid. In some embodiments, the nucleic acid is a double stranded nucleic acid (e.g., a double stranded DNA nucleic acid). In some embodiments, the nucleic acid is an amplicon. When the nucleic acid is double stranded the molecular mass is determined for both strands. In one embodiment, the strands may be separated before introduction into the mass spectrometer, or the strands may be separated by the mass spectrometer (for example, electro-spray ionization will separate the hybridized strands). The molecular mass of each strand is measured by the mass spectrometer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonyl-methyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68: 90-99; the phosphodiester method of Brown et al. (1979) *Meth Enzymol.* 68: 109-151; the diethylphosphoramidite method of Beaucage et al. (1981) *Tetrahedron Lett.* 22: 1859-1862; the triester method of Matteucci et al. (1981) *J Am Chem Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

As used herein a "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, etc.) from one or more HPV. Samples can include, for example, blood, saliva, urine, feces, anorectal swabs, vaginal swabs, cervical swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As is used herein, the term "single primer pair identification" means that one or more bioagents can be identified using a single primer pair. A base composition signature for an amplicon may singly identify one or more bioagents.

As used herein, a "sub-species characteristic" is a genetic characteristic that provides the means to distinguish two members of the same bioagent species. For example, one viral strain may be distinguished from another viral strain of the same species by possessing a genetic change (e.g., for example, a nucleotide deletion, addition or substitution) in one of the viral genes, such as the RNA-dependent RNA polymerase.

As used herein, in some embodiments the term "substantial complementarity" means that a primer member of a primer pair comprises between about 70%-100%, or between about 80-100%, or between about 90-100%, or between about 95-100%, or between about 99-100% complementarity with the conserved binding sequence of a nucleic acid from a given bioagent. Similarly, the primer pairs provided herein may comprise between about 70%-100%, or between about 80-100%, or between about 90-100%, or between about 95-100% identity, or between about 99-100% sequence identity with the primer pairs disclosed in Tables 1 and 2. These ranges of complementarity and identity are inclusive of all whole or partial numbers embraced within the recited range numbers. For example, and not limitation, 75.667%, 82%, 91.2435% and 97% complementarity or sequence identity are all numbers that fall within the above recited range of 70% to 100%, therefore forming a part of this description. In some embodiments, any oligonucleotide primer pair may have one or both primers with less then 70% sequence homology with a corresponding member of any of the primer pairs of Tables 1 and 2 if the primer pair has the capability of producing an amplification product corresponding to the desired HPV identifying amplicon.

A "system" in the context of analytical instrumentation refers a group of objects and/or devices that form a network for performing a desired objective.

As used herein, "triangulation identification" means the use of more than one primer pair to generate a corresponding amplicon for identification of a bioagent. The more than one primer pair can be used in individual wells or vessels or in a multiplex PCR assay. Alternatively, PCR reactions may be carried out in single wells or vessels comprising a different primer pair in each well or vessel. Following amplification the amplicons are pooled into a single well or container which is then subjected to molecular mass analysis. The combination of pooled amplicons can be chosen such that the expected ranges of molecular masses of individual amplicons are not overlapping and thus will not complicate identification of signals. Triangulation is a process of elimination, wherein a first primer pair identifies that an unknown bioagent may be one of a group of bioagents. Subsequent primer pairs are used in triangulation identification to further refine the identity of the bioagent amongst the subset of possibilities generated with the earlier primer pair. Triangulation identification is complete when the identity of the bioagent is determined. The triangulation identification process may also be used to reduce false negative and false positive signals, and enable reconstruction of the origin of hybrid or otherwise engineered bioagents. For example, identification of the three part toxin genes typical of *B. anthracis* (Bowen et al., *J Appl Microbiol.*, 1999, 87, 270-278) in the absence of the expected compositions from the *B. anthracis* genome would suggest a genetic engineering event.

As used herein, the term "unknown bioagent" can mean, for example: (i) a bioagent whose existence is not known (for example, the SARS coronavirus was unknown prior to April 2003) and/or (ii) a bioagent whose existence is known (such as the well known bacterial species *Staphylococcus aureus* for example) but which is not known to be in a sample to be analyzed. For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, the second meaning (ii) of "unknown" bioagent would apply because the SARS coronavirus became known to science subsequent to April 2003 because it was not known what bioagent was present in the sample.

As used herein, the term "variable region" is used to describe a region that falls between any one primer pair described herein. The region possesses distinct base compositions between at least two bioagents, such that at least one bioagent can be identified at, for example, the family, genus, species or sub-species level. The degree of variability between the at least two bioagents need only be sufficient to allow for identification using mass spectrometry analysis, as described herein.

As used herein, a "wobble base" is a variation in a codon found at the third nucleotide position of a DNA triplet. Variations in conserved regions of sequence are often found at the third nucleotide position due to redundancy in the amino acid code.

Provided herein are methods, compositions, kits, and related systems for the detection and identification of bioagents (e.g., species of HPV) using bioagent identifying amplicons. In some embodiments, primers are selected to hybridize to conserved sequence regions of nucleic acids derived from a bioagent and which flank variable sequence regions to yield a bioagent identifying amplicon which can be amplified and which is amenable to molecular mass determination. In some embodiments, the molecular mass is converted to a base composition, which indicates the number of each nucleotide in the amplicon. Systems employing software and hardware useful in converting molecular mass data into base composition information are available from, for example, Ibis Biosciences, Inc. (Carlsbad, Calif.), for example the Ibis T5000 Biosensor System, and are described in U.S. patent application Ser. No. 10/754,415, filed Jan. 9, 2004, incorporated by reference herein in its entirety. In some embodiments, the molecular mass or corresponding base composition of one or more different amplicons is queried against a database of molecular masses or base compositions indexed to bioagents and to the primer pair used to generate the amplicon. A match of the measured base composition to a database entry base composition associates the sample bioagent to an indexed bioagent in the database. Thus, the identity of the unknown bioagent is determined. No prior knowledge of the unknown bioagent is necessary to make an identification. In some instances, the measured base composition associates with more than one database entry base composition. Thus, a second/subsequent primer pair is generally used to generate an amplicon, and its measured base composition is similarly compared to the database to determine its identity in triangulation identification. Furthermore, the methods and other aspects of the invention can be applied to rapid parallel multiplex analyses, the results of which can be employed in a triangulation identification strategy. Thus, in some embodiments, the present invention provides rapid throughput and does not require nucleic acid sequencing or knowledge of the linear sequences of nucleobases of the amplified target sequence for bioagent detection and identification.

Particular embodiments of the mass-spectrum based detection methods are described in the following patents, patent applications and scientific publications, all of which are herein incorporated by reference as if fully set forth herein: U.S. Pat. Nos. 7,108,974; 7,217,510; 7,226,739; 7,255,992; 7,312,036; 7,339,051; US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338; 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; WO2007/100397; WO2007/118222; Ecker et al., Ibis T5000: a universal biosensor approach for microbiology. *Nat Rev Microbiol.* 2008 Jun. 3.; Ecker et al., The Microbial Rosetta Stone Database: A compilation of global and emerging infectious microorganisms and bioterrorist threat agents. *BMC Microbiology.* 2005. 5(1): 19.; Ecker et al., The Ibis T5000 Universal Biosensor: An Automated Platform for Pathogen Identification and Strain Typing. *JALA.* 2006. 6(11): 341-351.; Ecker et al., The Microbial Rosetta Stone Database: A common structure for microbial biosecurity threat agents. *J Forensic Sci.* 2005. 50(6): 1380-5.; Ecker et al., Identification of *Acinetobacter* species and genotyping of *Acinetobacter baumannii* by multilocus PCR and mass spectrometry. *J Clin Microbiol.* 2006 August; 44(8): 2921-32.; Ecker et al., Rapid identification and strain-typing of respiratory pathogens for epidemic surveillance. *Proc Natl Acad Sci USA.* 2005 May 31; 102(22):8012-7. Epub 2005 May 23; Wortmann et al., Genotypic evolution of *Acinetobacter baumannii* Strains in an outbreak associated with war trauma, *Infect Control Hosp Epidemiol.* 2008 June; 29(6): 553-555.; Hannis et al., High-resolution genotyping of *Campylobacter* species by use of PCR and high-throughput mass spectrometry. *J Clin Microbiol.* 2008 April; 46(4): 1220-5.; Blyn et al., Rapid detection and molecular serotyping of adenovirus by use of PCR followed by electrospray ionization mass spectrometry. *J Clin Microbiol.* 2008 February; 46(2):644-51.; Eshoo et al., Direct broad-range detection of alphaviruses in mosquito extracts, *Virology.* 2007 Nov. 25; 368(2):286-95.; Sampath et al., Global surveillance of emerging Influenza virus genotypes by mass spectrometry. *PLoS ONE.* 2007 May 30; 2(5):e489.; Sampath et al., Rapid identification of emerging infectious agents using PCR and electrospray ionization mass spectrometry. *Ann N Y Acad. Sci.* 2007 April; 1102: 109-20.; Hujer et al., Analysis of antibiotic resistance genes in multidrug-resistant *Acinetobacter* sp. isolates from military and civilian patients treated at the Walter Reed Army Medical Center. *Antimicrob Agents Chemother.* 2006 December; 50(12):4114-23.; Hall et al., Base composition analysis of human mitochondrial DNA using electrospray ionization mass spectrometry: a novel tool for the identification and differentiation of humans. *Anal Biochem.* 2005 Sep. 1; 344(1):53-69.; Sampath et al., Rapid identification of emerging pathogens: coronavirus. *Emerg Infect Dis.* 2005 Mar.; 11(3):373-9.; Jiang Y, Hofstadler S A. A highly efficient and automated method of purifying and desalting PCR products for analysis by electrospray ionization mass spectrometry. *Anal Biochem.* 2003. 316: 50-57.; Jiang et al., Mitochondrial DNA mutation detection by electrospray mass spectrometry. *Clin Chem.* 2006. 53(2): 195-203. Epub Dec 7.; Russell et al., Transmission dynamics and prospective environmental sampling of adenovirus in a military recruit setting. *J Infect Dis.* 2006. 194(7): 877-85. Epub 2006 Aug. 25.; Hofstadler et al., Detection of microbial agents using broadrange PCR with detection by mass spectrometry: The TIGER concept. Chapter in *Encyclopedia of Rapid Microbiological Methods.* 2006.; Hofstadler et al., Selective ion filtering by digital thresholding: A method to unwind complex ESI-mass spectra and eliminate signals from low molecular weight chemical noise. *Anal Chem.* 2006. 78(2): 372-378.; Hofstadler et al., TIGER: The Universal Biosensor. *Int J Mass Spectrom.* 2005. 242(1): 23-41.; Van Ert et al., Mass spectrometry provides accurate characterization of two genetic marker types in *Bacillus anthracis. Biotechniques.* 2004. 37(4): 642-4, 646, 648.; Sampath et al., Forum on Microbial Threats: Learning from SARS: Preparing for the Next Disease Outbreak—Workshop Summary (ed. Knobler S E, Mahmoud A, Lemon S.) The National Academies Press, Washington, D.C. 2004. 181-185.

In certain embodiments, bioagent identifying amplicons amenable to molecular mass determination produced by the primers described herein are either of a length, size or mass compatible with a particular mode of molecular mass determination, or compatible with a means of providing a fragmentation pattern in order to obtain fragments of a length compatible with a particular mode of molecular mass determination. Such means of providing a fragmentation pattern of an amplicon include, but are not limited to, cleavage with restriction enzymes or cleavage primers, sonication or other means of fragmentation. Thus, in some embodiments, bioagent identifying amplicons are larger than 200 nucleobases and are amenable to molecular mass determination following restriction digestion. Methods of using restriction enzymes and cleavage primers are well known to those with ordinary skill in the art.

In some embodiments, amplicons corresponding to bioagent identifying amplicons are obtained using the polymerase chain reaction (PCR). Other amplification methods may be used such as ligase chain reaction (LCR), low-stringency single primer PCR, and multiple strand displacement amplification (MDA). (Michael, S F., *Biotechniques* (1994), 16:411-412 and Dean et al., *Proc. Natl. Acad. Sci. U.S.A.* (2002), 99, 5261-5266).

Figure 2:
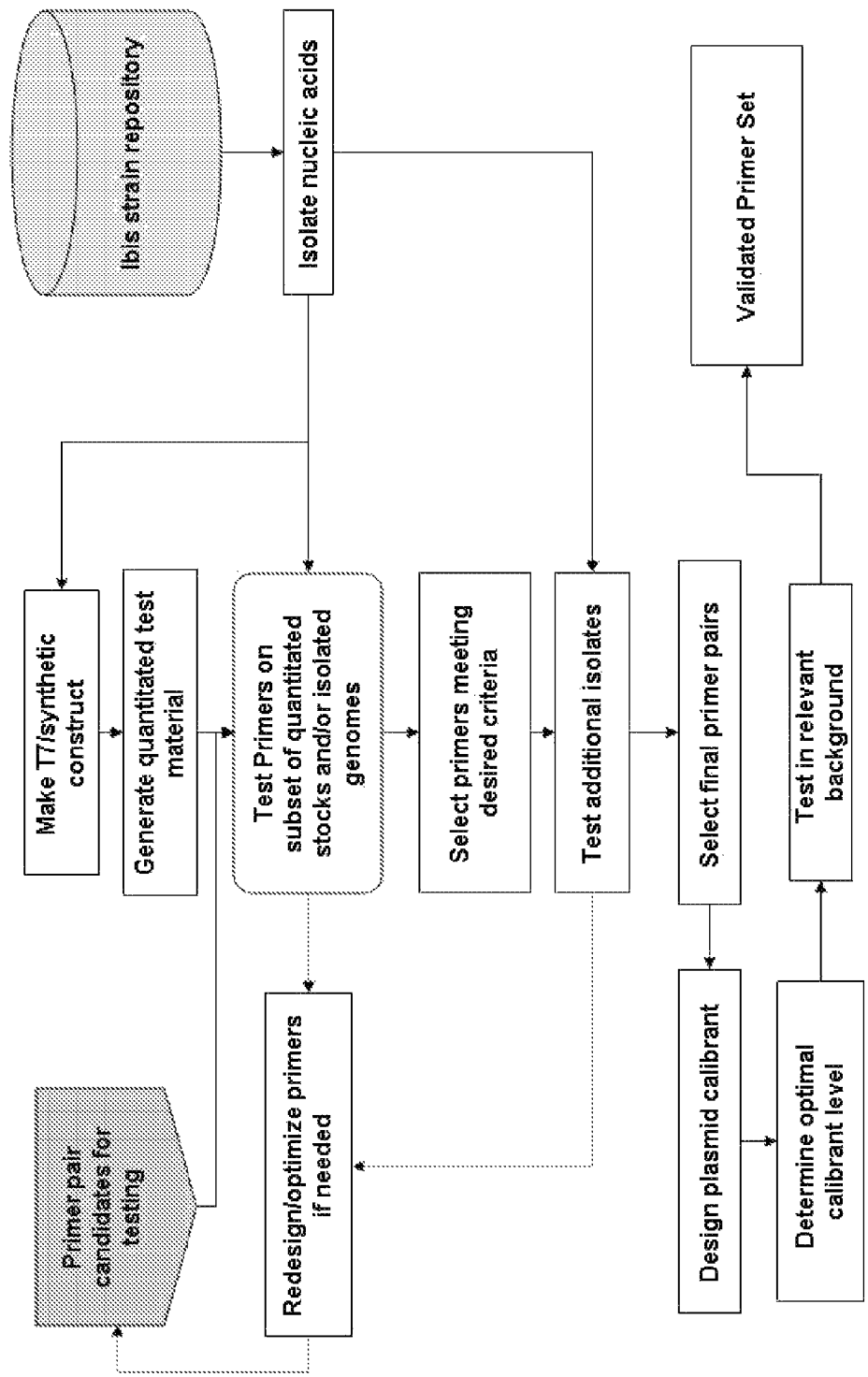
FIG. 2 shows a process diagram illustrating one embodiment of the primer pair validation process. Here select primers are shown meeting test criteria. Criteria include but are not limited to, the ability to amplify targeted HPV nucleic acid, the ability to exclude non-target bioagents, the ability to not produce unexpected amplicons, the ability to not dimerize, the ability to have analytical limits of detection of ≦100 genomic copies/reaction, and the ability to differentiate amongst different target organisms.

One embodiment of a process flow diagram used for primer selection and validation process is depicted in FIGS. 1 and 2. For each group of organisms, candidate target sequences are identified (200) from which nucleotide sequence alignments are created (210) and analyzed (220). Primers are then configured by selecting priming regions (230) to facilitate the selection of candidate primer pairs (240). The primer pair sequence is typically a "best fit" amongst the aligned sequences, such that the primer pair sequence may or may not be fully complementary to the hybridization region on any one of the bioagents in the alignment. Thus, best fit primer pair sequences are those with sufficient complementarity with two or more bioagents to hybridize with the two or more bioagents and generate an amplicon. The primer pairs are then subjected to in silico analysis by electronic PCR (ePCR) (300) wherein bioagent identifying amplicons are obtained from sequence databases such as GenBank or other sequence collections (310) and tested for specificity in silico (320). Bioagent identifying amplicons obtained from ePCR of GenBank sequences (310) may also be analyzed by a probability model which predicts the capability of a given amplicon to identify unknown bioagents. Preferably, the base compositions of amplicons with favorable probability scores are then stored in a base composition database (325). Alternatively, base compositions of the bioagent identifying amplicons obtained from the primers and GenBank sequences are directly entered into the base composition database (330). Candidate primer pairs (240) are validated by in vitro amplification by a method such as PCR analysis (400) of nucleic acid from a collection of organisms (410). Amplicons thus obtained are analyzed to confirm the sensitivity, specificity and reproducibility of the primers used to obtain the amplicons (420).

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers typically are employed as compositions for use in methods for identification of bioagents as follows: a primer pair composition is contacted with nucleic acid of an unknown isolate suspected of comprising HPV. The nucleic acid is then amplified by a nucleic acid amplification technique, such as PCR for example, to obtain an amplicon that represents a bioagent identifying amplicon. The molecular mass of the strands of the double-stranded amplicon is determined by a molecular mass measurement technique such as mass spectrometry, for example. Preferably the two strands of the double-stranded amplicon are separated during the ionization process; however, they may be separated prior to mass spectrometry measurement. In some embodiments, the mass spectrometer is electrospray Fourier transform ion cyclotron resonance mass spectrometry (ESI-FTICR-MS) or electrospray time of flight mass spectrometry (ESI-TOF-MS). A list of possible base compositions may be generated for the molecular mass value obtained for each strand, and the choice of the base composition from the list is facilitated by matching the base composition of one strand with a complementary base composition of the other strand. A measured molecular mass or base composition calculated therefrom is then compared with a database of molecular masses or base compositions indexed to primer pairs and to known bioagents. A match between the measured molecular mass or base composition of the amplicon and the database molecular mass or base composition for that indexed primer pair correlates the measured molecular mass or base composition with an indexed bioagent, thus identifying the unknown bioagent (e.g. the species of HPV). In some embodiments, the primer pair used is at least one of the primer pairs of Tables 1 and 2. In some embodiments, the method is repeated using a different primer pair to resolve possible ambiguities in the identification process or to improve the confidence level for the identification assignment (triangulation identification). In some embodiments, for example, where the unknown is a novel, previously uncharacterized organism, the molecular mass or base composition from an amplicon generated from the unknown is matched with one or more best match molecular masses or base compositions from a database to predict a family, genus, species, sub-type, etc. of the unknown. Such information may assist further characterization of the unknown or provide a physician treating a patient infected by the unknown with a therapeutic agent best calculated to treat the patient.

In certain embodiments, HPV is detected with the systems and methods of the present invention in combination with other bioagents, including viruses, bacteria, fungi, or other bioagents. In particular embodiments, a panel is employed that includes HPV and other related or un-related bioagents. Such panels may be specific for a particular type of bioagent, or specific for a specific type of test (e.g., for testing the safety of blood, one may include commonly present viral pathogens such as HCV, HIV, and bacteria that can be contracted via a blood transfusion).

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR).

In some embodiments, the oligonucleotide primers are broad range survey primers which hybridize to conserved regions of nucleic acid. The broad range primer may identify the unknown bioagent depending on which bioagent is in the sample. In other cases, the molecular mass or base composition of an amplicon does not provide sufficient resolution to identify the unknown bioagent as any one bioagent at or below the species level. These cases generally benefit from further analysis of one or more amplicons generated from at least one additional broad range survey primer pair, or from at least one additional division-wide primer pair, or from at least one additional drill-down primer pair. Identification of sub-species characteristics may be required, for example, to determine a clinical treatment of patient, or in rapidly responding to an outbreak of a new species, sub-type, etc. of pathogen to prevent an epidemic or pandemic.

One with ordinary skill in the art of design of amplification primers will recognize that a given primer need not hybridize with 100% complementarity in order to effectively prime the synthesis of a complementary nucleic acid strand in an amplification reaction. Primer pair sequences may be a "best fit" amongst the aligned bioagent sequences, thus they need not be fully complementary to the hybridization region of any one of the bioagents in the alignment. Moreover, a primer may hybridize over one or more segments such that intervening or adjacent segments are not involved in the hybridization event (e.g., for example, a loop structure or a hairpin structure). The primers may comprise at least 70%, at least 75%, at least 80%, at least 85%, at least 90%, at least 95% or at least 99% sequence identity with any of the primers listed in Tables 1 and 2. Thus, in some embodiments, an extent of variation of 70% to 100%, or any range falling within, of the sequence identity is possible relative to the specific primer sequences disclosed herein. To illustrate, determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489). In some embodiments, complementarity of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range falling within) sequence identity with the primer sequences specifically disclosed herein.

In some embodiments, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of, e.g., Taq DNA polymerase (Magnuson et al., *Biotechniques,* 1996, 21, 700-709), an occurrence which may lead to ambiguous results arising from molecular mass analysis.

Primers may contain one or more universal bases. Because any variation (due to codon wobble in the third position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" base pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., *Nucleosides and Nucleotides,* 1995, 14, 1001-1003), the degenerate nucleotides dP or dK, an acyclic nucleoside analog containing 5-nitroindazole (Van Aerschot et al., *Nucleosides and Nucleotides.,* 1995, 14, 1053-1056) or the purine analog 1-(2-deoxy-beta-D-ribofuranosyl)-imidazole-4-carboxamide (Sala et al., *Nucl. Acids Res.,* 1996, 24, 3302-3306).

In some embodiments, to compensate for weaker binding by the wobble base, oligonucleotide primers are configured such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S. Pre-Grant Publication No. 2003-0170682; also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a possible source of ambiguity in the determination of base composition of amplicons. Addition of mass-modifying tags to certain nucleobases of a given primer will result in simplification of de novo determination of base composition of a given bioagent identifying amplicon from its molecular mass.

In some embodiments, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{13}N$ and $^{13}C$.

In some embodiments, the molecular mass of a given bioagent (e.g., a species of HPV) identifying amplicon is determined by mass spectrometry. Mass spectrometry is intrinsically a parallel detection scheme without the need for radioactive or fluorescent labels, because an amplicon is identified by its molecular mass. The current state of the art in mass spectrometry is such that less than femtomole quantities of material can be analyzed to provide information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplicons using one of a variety of ionization techniques to convert the sample to the gas phase. These ionization methods include, but are not limited to, electrospray ionization (ESI), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used include, but are not limited to, Fourier transform ion cyclotron resonance mass spectrometry (FT-ICR-MS), time of flight (TOF), ion trap, quadrupole, magnetic sector, Q-TOF, and triple quadrupole.

In some embodiments, assignment of previously unobserved base compositions (also known as "true unknown base compositions") to a given phylogeny can be accomplished via the use of pattern classifier model algorithms. Base compositions, like sequences, may vary slightly from strain to strain within species, for example. In some embodiments, the pattern classifier model is the mutational probability model. In other embodiments, the pattern classifier is the polytope model. A polytope model is the mutational probability model that incorporates both the restrictions among strains and position dependence of a given nucleobase within a triplet. In certain embodiments, a polytope pattern classifier is used to classify a test or unknown organism according to its amplicon base composition.

In some embodiments, it is possible to manage this diversity by building "base composition probability clouds" around the composition constraints for each species. A "pseudo four-dimensional plot" may be used to visualize the concept of base composition probability clouds. Optimal primer design typically involves an optimal choice of bioagent identifying amplicons and maximizes the separation between the base composition signatures of individual bioagents. Areas where clouds overlap generally indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of an unknown bioagent whose assigned base composition has not been previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

Provided herein is bioagent classifying information at a level sufficient to identify a given bioagent. Furthermore, the process of determining a previously unknown base composition for a given bioagent (for example, in a case where sequence information is unavailable) has utility by providing additional bioagent indexing information with which to populate base composition databases. The process of future bioagent identification is thus improved as additional base composition signature indexes become available in base composition databases.

Figure 3:
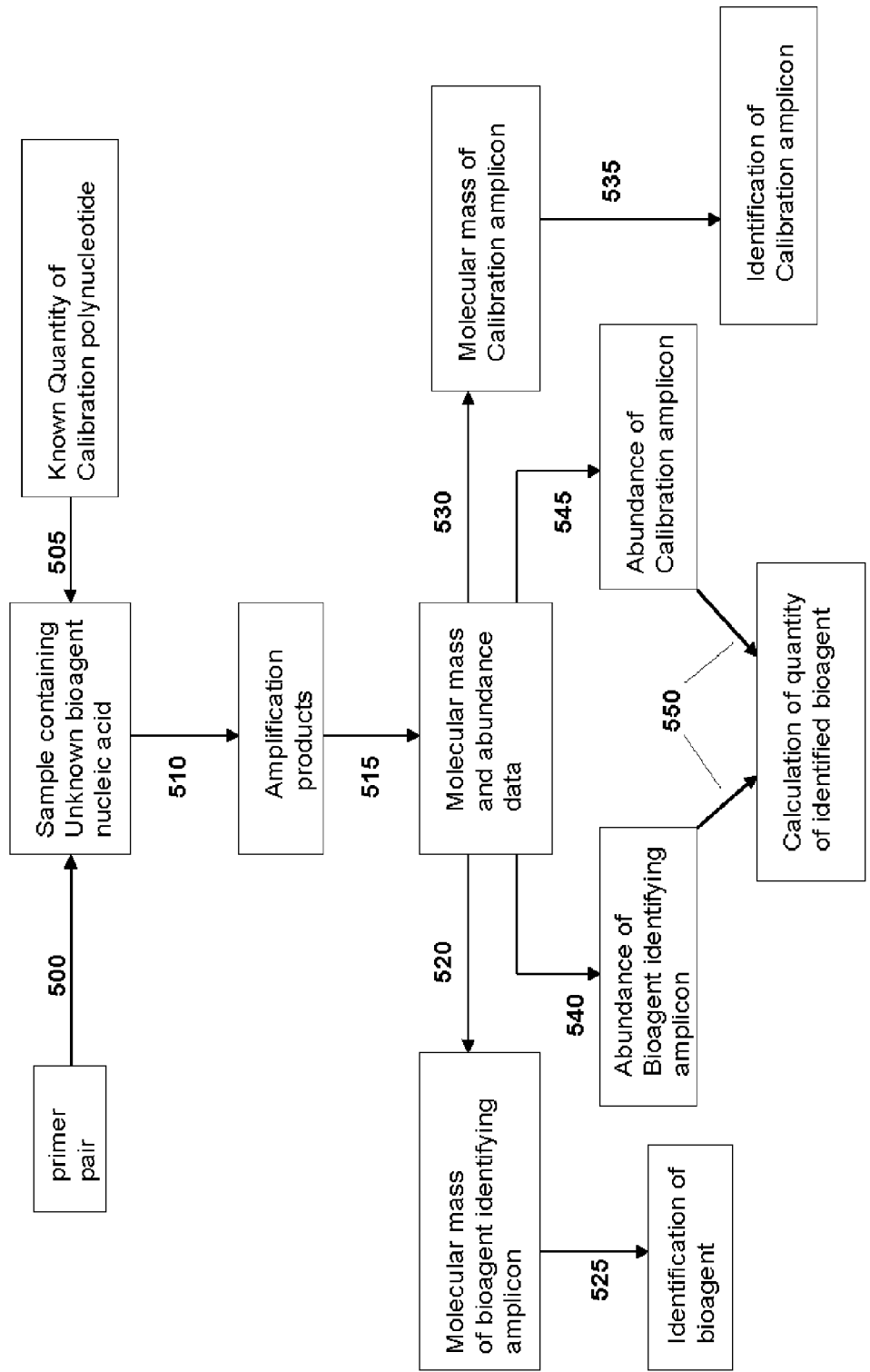
FIG. 3 shows a process diagram illustrating an embodiment of the calibration method.

In some embodiments, the identity and quantity of an unknown bioagent may be determined using the process illustrated in FIG. 3. Primers (500) and a known quantity of a calibration polynucleotide (505) are added to a sample containing nucleic acid of an unknown bioagent. The total nucleic acid in the sample is then subjected to an amplification reaction (510) to obtain amplicons. The molecular masses of amplicons are determined (515) from which are obtained molecular mass and abundance data. The molecular mass of the bioagent identifying amplicon (520) provides for its identification (525) and the molecular mass of the calibration amplicon obtained from the calibration polynucleotide (530) provides for its quantification (535). The abundance data of the bioagent identifying amplicon is recorded (540) and the abundance data for the calibration data is recorded (545), both of which are used in a calculation (550) which determines the quantity of unknown bioagent in the sample.

In certain embodiments, a sample comprising an unknown bioagent is contacted with a primer pair which amplifies the nucleic acid from the bioagent, and a known quantity of a polynucleotide that comprises a calibration sequence. The amplification reaction then produces two amplicons: a bioagent identifying amplicon and a calibration amplicon. The bioagent identifying amplicon and the calibration amplicon are distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent by base composition analysis. The abundance data enables calculation of the quantity of the bioagent, based on the knowledge of the quantity of calibration polynucleotide contacted with the sample.

In some embodiments, construction of a standard curve in which the amount of calibration or calibrant polynucleotide spiked into the sample is varied provides additional resolution and improved confidence for the determination of the quantity of bioagent in the sample. Alternatively, the calibration polynucleotide can be amplified in its own reaction vessel or vessels under the same conditions as the bioagent. A standard curve may be prepared there from, and the relative abundance of the bioagent determined by methods such as linear regression: In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single construct (preferably a vector) which functions as the calibration polynucleotide.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide gives rise to a calibration amplicon. Failure to produce a measurable calibration amplicon indicates a failure of amplification or subsequent analysis step such as amplicon purification or molecular mass determination. Reaching a conclusion that such failures have occurred is, in itself, a useful event. In some embodiments, the calibration sequence is comprised of DNA. In some embodiments, the calibration sequence is comprised of RNA.

In some embodiments, a calibration sequence is inserted into a vector which then functions as the calibration polynucleotide. In some embodiments, more than one calibration sequence is inserted into the vector that functions as the calibration polynucleotide. Such a calibration polynucleotide is herein termed a "combination calibration polynucleotide." It should be recognized that the calibration method should not be limited to the embodiments described herein. The calibration method can be applied for determination of the quantity of any bioagent identifying amplicon when an appropriate standard calibrant polynucleotide sequence is designed and used.

In certain embodiments, primer pairs are configured to produce bioagent identifying amplicons within more conserved regions of an HPV, while others produce bioagent identifying amplicons within regions that are may evolve more quickly. Primer pairs that characterize amplicons in a conserved region with low probability that the region will evolve past the point of primer recognition are useful, e.g., as a broad range survey-type primer. Primer pairs that characterize an amplicon corresponding to an evolving genomic region are useful, e.g., for distinguishing emerging bioagent strain variants.

The primer pairs described herein provide reagents, e.g., for identifying diseases caused by emerging types of HPV. Base composition analysis eliminates the need for prior knowledge of bioagent sequence to generate hybridization probes. Thus, in another embodiment, there is provided a method for determining the etiology of a particular stain when the process of identification of is carried out in a clinical setting, and even when a new strain is involved. This is possible because the methods may not be confounded by naturally occurring evolutionary variations.

Another embodiment provides a means of tracking the spread of any species or strain of HPV when a plurality of samples obtained from different geographical locations are analyzed by methods described above in an epidemiological setting. For example, a plurality of samples from a plurality of different locations may be analyzed with primers which produce bioagent identifying amplicons, a subset of which identifies a specific strain. The corresponding locations of the members of the strain-containing subset indicate the spread of the specific strain to the corresponding locations.

Also provided are kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to twenty primer pairs, from one to ten primer pairs, from one to eight pairs, from one to five primer pairs, from one to three primer pairs, or from one to two primer pairs. In some embodiments, the kit may comprise one or more primer pairs recited in Tables 1 and 2. In certain embodiments, kits include all of the primer pairs recited in Table 1, or Table 2, or Tables 1 and 2.

In some embodiments, the kit may also comprise a sufficient quantity of reverse transcriptase, a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. In some embodiments, the kit further comprises instructions for analysis, interpretation and dissemination of data acquired by the kit. In other embodiments, instructions for the operation, analysis, interpretation and dissemination of the data of the kit are provided on computer readable media. A kit may also comprise amplification reaction containers such as microcentrifuge tubes, microtiter plates, and the like. A kit may also comprise reagents or other materials for isolating bioagent nucleic acid or bioagent identifying amplicons from amplification reactions, including, for example, detergents, solvents, or ion exchange resins which may be linked to magnetic beads. A kit may also comprise a table of measured or calculated molecular masses and/or base compositions of bioagents using the primer pairs of the kit.

The invention also provides systems that can be used to perform various assays relating to HPV detection or identification. In certain embodiments, systems include mass spectrometers configured to detect molecular masses of amplicons produced using purified oligonucleotide primer pairs described herein. Other detectors that are optionally adapted for use in the systems of the invention are described further below. In some embodiments, systems also include controllers operably connected to mass spectrometers and/or other system components. In some of these embodiments, controllers are configured to correlate the molecular masses of the amplicons with bioagents to effect detection or identification. In some embodiments, controllers are configured to determine base compositions of the amplicons from the molecular masses of the amplicons. As described herein, the base compositions generally correspond to the HPV species identities. In certain embodiments, controllers include, or are operably connected to, databases of known molecular masses and/or known base compositions of amplicons of known species of HPV produced with the primer pairs described herein. Controllers are described further below.

In some embodiments, systems include one or more of the primer pairs described herein (e.g., in Tables 1 and 2). In certain embodiments, the oligonucleotides are arrayed on solid supports, whereas in others, they are provided in one or more containers, e.g., for assays performed in solution. In certain embodiments, the systems also include at least one detector or detection component (e.g., a spectrometer) that is configured to detect detectable signals produced in the container or on the support. In addition, the systems also optionally include at least one thermal modulator (e.g., a thermal cycling device) operably connected to the containers or solid supports to modulate temperature in the containers or on the solid supports, and/or at least one fluid transfer component (e.g., an automated pipettor) that transfers fluid to and/or from the containers or solid supports, e.g., for performing one or more assays (e.g., nucleic acid amplification, real-time amplicon detection, etc.) in the containers or on the solid supports.

Detectors are typically structured to detect detectable signals produced, e.g., in or proximal to another component of the given assay system (e.g., in a container and/or on a solid support). Suitable signal detectors that are optionally utilized, or adapted for use, herein detect, e.g., fluorescence, phosphorescence, radioactivity, absorbance, refractive index, luminescence, or mass. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, or scanning detectors. Detectors are also described in, e.g., Skoog et al., Principles of Instrumental Analysis, 5$^{th}$ Ed., Harcourt Brace College Publishers (1998), Currell, Analytical Instrumentation: Performance Characteristics and Quality, John Wiley & Sons, Inc. (2000), Sharma et al., Introduction to Fluorescence Spectroscopy, John Wiley & Sons, Inc. (1999), Valeur, Molecular Fluorescence: Principles and Applications, John Wiley & Sons, Inc. (2002), and Gore, Spectrophotometry and Spectrofluorimetry: A Practical Approach, 2.sup.nd Ed., Oxford University Press (2000), which are each incorporated by reference.

As mentioned above, the systems of the invention also typically include controllers that are operably connected to one or more components (e.g., detectors, databases, thermal modulators, fluid transfer components, robotic material handling devices, and the like) of the given system to control operation of the components. More specifically, controllers are generally included either as separate or integral system components that are utilized, e.g., to receive data from detectors (e.g., molecular masses, etc.), to effect and/or regulate temperature in the containers, or to effect and/or regulate fluid flow to or from selected containers. Controllers and/or other system components are optionally coupled to an appropriately programmed processor, computer, digital device, information appliance, or other logic device (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display or liquid crystal display), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a graphic user interface (GUI), or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming.

Figure 4:
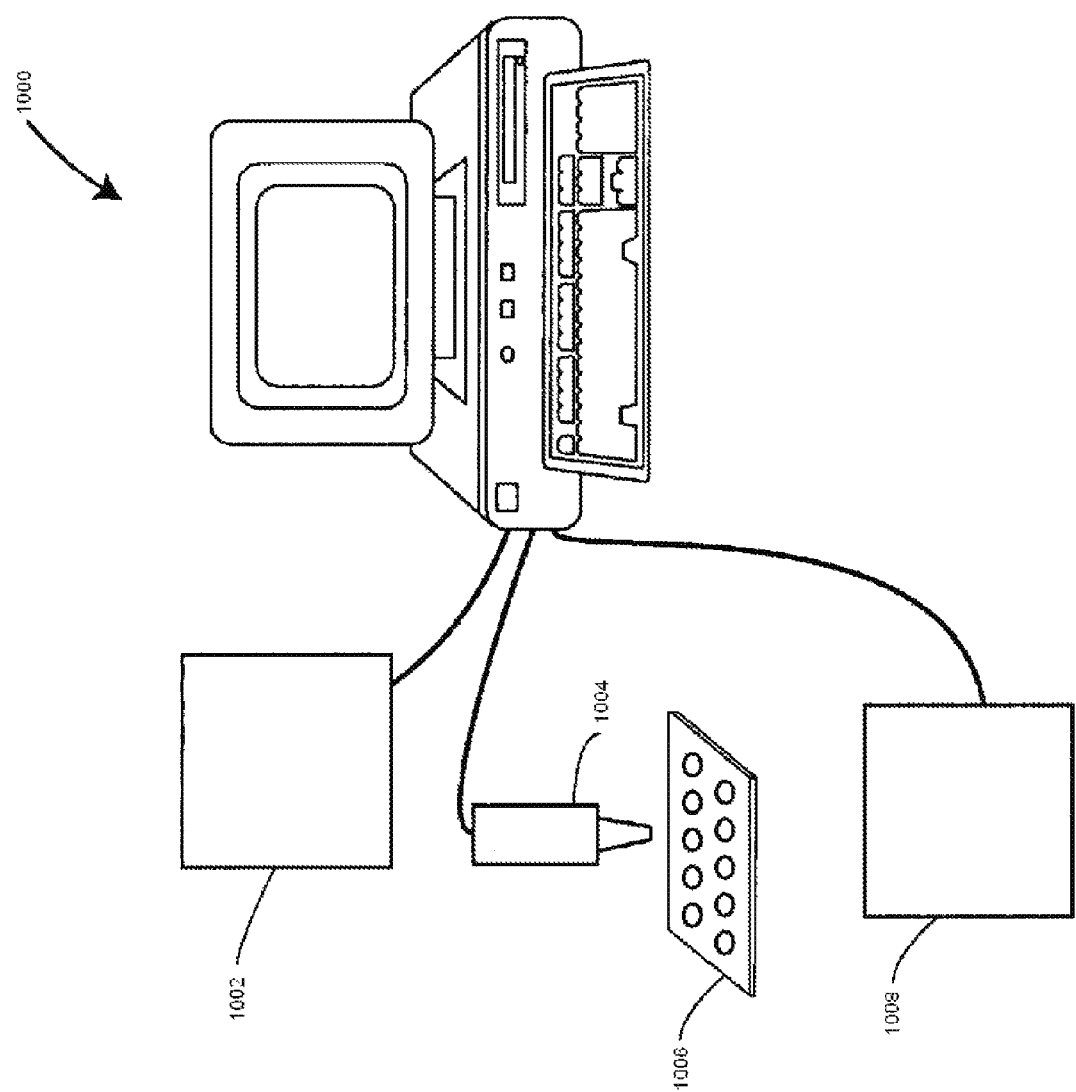
FIG. 4 shows a block diagram showing a representative system.

FIG. 4 is a schematic showing a representative system that includes a logic device in which various aspects of the present invention may be embodied. As will be understood by practitioners in the art from the teachings provided herein, aspects of the invention are optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform as desired. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

More specifically, FIG. 4 schematically illustrates computer 1000 to which mass spectrometer 1002 (e.g., an ESI-TOF mass spectrometer, etc.), fluid transfer component 1004

(e.g., an automated mass spectrometer sample injection needle or the like), and database 1008 are operably connected. Optionally, one or more of these components are operably connected to computer 1000 via a server (not shown in FIG. 4). During operation, fluid transfer component 1004 typically transfers reaction mixtures or components thereof (e.g., aliquots comprising amplicons) from multi-well container 1006 to mass spectrometer 1002. Mass spectrometer 1002 then detects molecular masses of the amplicons. Computer 1000 then typically receives this molecular mass data, calculates base compositions from this data, and compares it with entries in database 1008 to identify species or strains of HPV in a given sample. It will be apparent to one of skill in the art that one or more components of the system schematically depicted in FIG. 4 are optionally fabricated integral with one another (e.g., in the same housing).

compositions for PCR amplicons derived from HPV. The T5000 Biosensor System is a mass spectrometry based universal biosensor that uses mass measurements to derived base compositions of PCR amplicons to identify bioagents including, for example, bacteria, fungi, viruses and protozoa (S. A. Hofstadler et. al. *Int. J. Mass Spectrom*. (2005) 242:23-41, herein incorporated by reference). For this HPV assay primers from Tables 1 and 2 may be employed to generate PCR amplicons. The base composition of the PCR amplicons can be determined and compared to a database of known HPV base compositions to determine the identity of a HPV in a sample. Tables 1 and 2 shows exemplary primers pairs for detecting alphapapillomavirus, betapapillomavirus, gammapapillomavirus, Mupapillomavirus, and Nupapillomavirus. In Tables 1A and 2A, "I" represents inosine and Tp=5-propynyluracil (also known as propynylated thymine).

TABLE 1A

Primer Sequences

| Primer Pair Number | Primer Direction | Primer Sequence | SEQ ID NO: |
|---|---|---|---|
| 2534 | Forward | TAGGATGGTGATATGGTTGATACAGGCTTTGG | 1 |
| 2534 | Reverse | TCTGCAACCATTTGCAAATAATCTGGATATTT | 9 |
| 2537 | Forward | TTCAGATGTCTGTGTGGCGGCCTA | 2 |
| 2537 | Reverse | TACATATTCATCCGTGCTTACAACCTTAGA | 10 |
| 2540 | Forward | TAGATGATAGTGACATTGCATATAAATATGCA | 5 |
| 2540 | Reverse | TTTCTGCTCGTTTATAATGTCTACACAT | 13 |
| 2544 | Forward | TGACGAACCACAGCGTCACA | 6 |
| 2544 | Reverse | TGCACACAACGGACACACAAA | 14 |
| 2545 | Forward | TCGGGATGTAATGGCTGGTT | 3 |
| 2545 | Reverse | TACCATGTCCGAACCTGTATCTGT | 11 |
| 2546 | Forward | TCAGGATGGTTTTTGGTAGAGGCTATAGT | 4 |
| 2546 | Reverse | TGCCTGTGCTTCCAAGGAATTGTGTGTAATA | 12 |
| 2547 | Forward | TACACACAATTCCTTGGAAGCACAGGCA | 7 |
| 2547 | Reverse | TTAGGTCCTGCACAGCCGCATAATG | 15 |
| 2684 | Forward | TACTGTTATICAGGATGGTGATATGGT | 8 |
| 2684 | Reverse | TCTGCAACCATTTGIAAATAATCTGGATATTT | 16 |

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLE 1

High-Throughput ESI-Mass Spectrometry Assay for the Identification of HPV

This example describes a HPV pathogen identification assay which employs mass spectrometry determined base

TABLE 1B

Primer Pair Names and Reference Amplicon Lengths

| Primer Pair Number | Primer Pair Name | Reference Amplicon Length |
|---|---|---|
| 2534 | PAV_IMP_NC001526_6222-6355_2 | 134 |
| 2537 | PaV_A9_NC001526_5632-5720 | 89 |
| 2540 | PaV_A9_NC001526_1972-2112 | 141 |
| 2544 | PaV_A7_NC001357_748-895 | 148 |
| 2545 | PaV_A7_NC001357_947-1057 | 111 |
| 2546 | PaV_A10_NC000904_875-1027 | 153 |
| 2547 | PaV_A10_NC000904_1000-1079 | 80 |
| 2684 | PAV_IMP_MOD_NC001526_6212_6355_4 | 144 |

TABLE 1C

Individual Primer Names and Hybridization Coordinates

| Primer Pair Number | Primer Direction | Individual Primer Names |
|---|---|---|
| 2534 | Forward | PAV_IMP_NC001526_6222_6253_F |
| 2534 | Reverse | PAV_IMP_NC001526_6324_6355_R |
| 2537 | Forward | PAV_A9_NC001526_5632_5655_F |
| 2537 | Reverse | PAV_A9_NC001526_5691_5720_R |
| 2540 | Forward | PAV_A9_NC001526_1972_2003_F |
| 2540 | Reverse | PAV_A9_NC001526_2085_2112_R |
| 2544 | Forward | PAV_A7_NC001357_748_767_F |
| 2544 | Reverse | PAV_A7_NC001357_875_895_R |
| 2545 | Forward | PAV_A7_NC001357_947_966_F |
| 2545 | Reverse | PAV_A7_NC001357_1034_1057_R |
| 2546 | Forward | PAV_A10_NC000904_875_903_F |
| 2546 | Reverse | PAV_A10_NC000904_997_1027_R |
| 2547 | Forward | PAV_A10_NC000904_1000_1027_F |
| 2547 | Reverse | PAV_A10_NC000904_1055_1079_R |
| 2684 | Forward | PAV_IMP_MOD_NC001526_6212_6238_2_F |
| 2684 | Reverse | PAV_IMP_MOD_NC001526_6324_6355_2_R |

TABLE 1D

Gene Targets and GenBank gi Numbers

| Primer Pair Number | Target Genome Segment | HPV Strains Resolved | GenBank Reference gi Number |
|---|---|---|---|
| 2534 | major capsid protein | All Important HPVs | 9627100 |
| 2537 | major capsid protein | 16/31 and other A9 HPV | 9627100 |
| 2540 | replication protein | 16/31 and other A9 HPV | 9627100 |
| 2544 | E7 protein | 18/45 and other A7 HPV | 9626069 |
| 2545 | E1 protein | 18/45 and other A7 HPV | 9626069 |
| 2546 | E1 protein | 6/11 and other A10 HPV | 9633484 |
| 2547 | E1 protein | 6/11 and other A10 HPV | 9633484 |
| 2684 | major capsid protein | All Important HPVs | 9627100 |

TABLE 2A

Primer Sequences

| Primer Pair Number | Primer Direction | Primer Sequence | SEQ ID NO: |
|---|---|---|---|
| 2670 | Forward | TAGGATGGTGATATGGTTGATACAGGCTTTGG | 17 |
| 2670 | Reverse | TCTGCAACCATTTGCAAATAATCTGGATATTTCA | 44 |
| 2671 | Forward | TAGGATGGTGATATGGTTGATACAGGCTTTGG | 18 |
| 2671 | Reverse | TCTGCAACCATTTGIAAATAATCTGGATATTTCA | 45 |
| 2672 | Forward | TAGGATGGTGATATGGTTGATACAGGCTTTGG | 19 |
| 2672 | Reverse | TCTGCAACCATTTIIAAATAATCTGGATATTTCA | 46 |
| 2673 | Forward | TAGGATGGTGATATGGTTGATACAGGCTTTGG | 20 |
| 2673 | Reverse | TCTGCAACCATpTpTpGAAAATAATCTGGATATTT | 47 |
| 2674 | Forward | TAGGATGGTGATATGGTTGATACAGGCTTTGG | 21 |
| 2674 | Reverse | TCTGCAACCATTTGAAAATAATCTGGATATTT | 48 |
| 2675 | Forward | TAGGATGGTGATATGGTTGATACAGGCTTTGG | 22 |
| 2675 | Reverse | TCTGCAACCATTTGIAAATAATCTGGATATTT | 49 |
| 2676 | Forward | TAGGATGGTGATATGGTTGATACAGGCTTTGG | 23 |
| 2676 | Reverse | TCTGCAACCATTTIIAAATAATCTGGATATTT | 50 |
| 2677 | Forward | TAGGATGGTGATATGGTTGATACAGGCTTTGG | 24 |
| 2677 | Reverse | TCTGCAACCATTTIIAIATAATCTGGATATTT | 51 |
| 2678 | Forward | TAGGATGGTGATATGGTTGATACAGGCTIGG | 25 |
| 2678 | Reverse | TCTGCAACCATTTGIAAATAATCTGGATATTT | 52 |
| 2679 | Forward | TAGGATGGTGATATGGTTGATACAGGITITGG | 26 |
| 2679 | Reverse | TCTGCAACCATTTIIAAATAATCTGGATATTT | 53 |
| 2680 | Forward | TAGGATGGTGATATGGTTGATACIGGITITGG | 27 |
| 2680 | Reverse | TCTGCAACCATTTIIAIATAATCTGGATATTT | 54 |
| 2681 | Forward | TACTGTTATTCAGGATGGTGATATGGT | 28 |

TABLE 2A-continued

Primer Sequences

| Primer Pair Number | Primer Direction | Primer Sequence | SEQ ID NO: |
|---|---|---|---|
| 2681 | Reverse | TCTGCAACCATTTGIAAATAATCTGGATATTT | 55 |
| 2682 | Forward | TACTGTTATTCAGGATGGTGATATGGT | 29 |
| 2682 | Reverse | TCTGCAACCATTTIIAAATAATCTGGATATTT | 56 |
| 2683 | Forward | TACTGTTATTCAGGATGGTGATATGGT | 30 |
| 2683 | Reverse | TCTGCAACCATTTIIAIATAATCTGGATATTT | 57 |
| 2684 | Forward | TACTGTTATICAGGATGGTGATATGGT | 8 |
| 2684 | Reverse | TCTGCAACCATTTGIAAATAATCTGGATATTT | 16 |
| 2685 | Forward | TACTGTTATTCAGGATGGIGATATGGT | 32 |
| 2685 | Reverse | TCTGCAACCATTTIIAAATAATCTGGATATTT | 59 |
| 2686 | Forward | TACTGTTATICAGGATGGIGATATGGT | 33 |
| 2686 | Reverse | TCTGCAACCATTTIIAIATAATCTGGATATTT | 60 |
| 2687 | Forward | TTCAGATGTCTGTGTGGCIGCCTA | 34 |
| 2687 | Reverse | TACATATTCATCCGTGCTTACAACCTTAGA | 61 |
| 2688 | Forward | TTCAGATGTCTITGTGGCIGCCTA | 35 |
| 2688 | Reverse | TACATATTCATCCGTGCTTACAACCTTAGA | 62 |
| 2689 | Forward | TGGAAATCCTTTTTCTCAAGGACGTGGT | 36 |
| 2689 | Reverse | TAGTATTTTGTCCTGCCACICATTTAAACG | 63 |
| 2690 | Forward | TGGAAATCCTTTTTCTCAAGGACGTGGT | 37 |
| 2690 | Reverse | TAGTATTTTGTCCTGCCAIICATTTAAACG | 64 |
| 2691 | Forward | TGGAAATCCTTTTTCTCAAGGACGTGGT | 38 |
| 2691 | Reverse | TAGTATTTTGTCCTGCCIIICATTTAAACG | 65 |
| 2692 | Forward | TAGATGATAGTGAIATIGCATATIAATATGCA | 39 |
| 2692 | Reverse | TTTCTGCTCGTTTATAATGTCTACACAT | 66 |
| 2693 | Forward | TATGGTGCAGTGGGCATTTGATAATG | 40 |
| 2693 | Reverse | TTGCTTTTTAAAAATGCAGIIGCATT | 67 |
| 2694 | Forward | TATGGTGCAGTCGGCATTTGATAATG | 41 |
| 2694 | Reverse | TTGCTTTTTAAAAATGCIIIIGCATT | 68 |
| 2695 | Forward | TATGGTGCAGTGGGCATITGATAATG | 42 |
| 2695 | Reverse | TTGCTTTTTAAAAATGCAGIIGCATT | 69 |
| 2696 | Forward | TATGGTGCAGTGGGCATTTGATAATG | 43 |
| 2696 | Reverse | TATTTGCCTGCIIATTGCTITTTAAAAA | 70 |

TABLE 2B

Primer Pair Names and Reference Amplicon Lengths

| Primer Pair Number | Primer Pair Name | Reference Amplicon Length |
|---|---|---|
| 2670 | PAV_IMP_MOD_NC001526_6222_6355 | 134 |
| 2671 | PAV_IMP_MOD_NC001526_6222_6355_2 | 134 |
| 2672 | PAV_IMP_MOD_NC001526_6222_6355_3 | 134 |
| 2673 | PAV_IMP_MOD_NC001526_6222_6355_4P | 134 |
| 2674 | PAV_IMP_MOD_NC001526_6222_6355_5 | 134 |
| 2675 | PAV_IMP_MOD_NC001526_6222_6355_6 | 134 |
| 2676 | PAV_IMP_MOD_NC001526_6222_6355_7 | 134 |
| 2677 | PAV_IMP_MOD_NC001526_6222_6355_8 | 134 |
| 2678 | PAV_IMP_MOD_NC001526_6222_6355_9 | 134 |
| 2679 | PAV_IMP_MOD_NC001526_6222_6355_10 | 134 |
| 2680 | PAV_IMP_MOD_NC001526_6222_6355_11 | 134 |
| 2681 | PAV_IMP_MOD_NC001526_6212_6355 | 144 |
| 2682 | PAV_IMP_MOD_NC001526_6212_6355_2 | 144 |
| 2683 | PAV_IMP_MOD_NC001526_6212_6355_3 | 144 |
| 2684 | PAV_IMP_NC001526_6212_6355_4 | 144 |
| 2684 | PAV_IMP_MOD_NC001526_6212_6355_4 | 144 |
| 2685 | PAV_IMP_MOD_NC001526_6212_6355_5 | 144 |
| 2686 | PAV_IMP_MOD_NC001526_6212_6355_6 | 144 |
| 2687 | PAV_A9_MOD_NC001526_5632_5720 | 89 |
| 2688 | PAV_A9_MOD_NC001526_5632_5720_2 | 89 |
| 2689 | PAV_A9_MOD_NC001526_2688_2802 | 115 |
| 2690 | PAV_A9_MOD_NC001526_2688_2802_2 | 115 |
| 2691 | PAV_A9_MOD_NC001526_2688_2802_3 | 115 |
| 2692 | PAV_A9_MOD_NC001526_1972_2112 | 141 |
| 2693 | PAV_A7_A10_NC000904_1912_2022 | 111 |
| 2694 | PAV_A7_A10_NC000904_1912_2022_2 | 111 |
| 2695 | PAV_A7_A10_NC000904_1912_2022_3 | 111 |
| 2696 | PAV_A7_A10_NC000904_1912_2036 | 125 |

TABLE 2C

Individual Primer Names and Hybridization Coordinates

| Primer Pair Number | Primer Direction | Individual Primer Names |
|---|---|---|
| 2670 | Forward | PAV_IMP_MOD_NC001526_6222_6253_F |
| 2670 | Reverse | PAV_IMP_MOD_NC001526_6321_6355_R |
| 2671 | Forward | PAV_IMP_MOD_NC001526_6222_6253_F |
| 2671 | Reverse | PAV_IMP_MOD_NC001526_6321_6355_2_R |
| 2672 | Forward | PAV_IMP_MOD_NC001526_6222_6253_F |
| 2672 | Reverse | PAV_IMP_MOD_NC001526_6321_6355_3_R |
| 2673 | Forward | PAV_IMP_MOD_NC001526_6222_6253_F |
| 2673 | Reverse | PAV_IMP_MOD_NC001526_6324_6355P_R |
| 2674 | Forward | PAV_IMP_MOD_NC001526_6222_6253_F |
| 2674 | Reverse | PAV_IMP_MOD_NC001526_6324_6355_R |
| 2675 | Forward | PAV_IMP_MOD_NC001526_6222_6253_F |
| 2675 | Reverse | PAV_IMP_MOD_NC001526_6324_6355_2_R |
| 2676 | Forward | PAV_IMP_MOD_NC001526_6222_6253_F |
| 2676 | Reverse | PAV_IMP_MOD_NC001526_6324_6355_3_R |
| 2677 | Forward | PAV_IMP_MOD_NC001526_6222_6253_F |
| 2677 | Reverse | PAV_IMP_MOD_NC001526_6324_6355_4_R |
| 2678 | Forward | PAV_IMP_MOD_NC001526_6222_6253_2_F |
| 2678 | Reverse | PAV_IMP_MOD_NC001526_6324_6355_2_R |
| 2679 | Forward | PAV_IMP_MOD_NC001526_6222_6253_3_F |
| 2679 | Reverse | PAV_IMP_MOD_NC001526_6324_6355_3_R |
| 2680 | Forward | PAV_IMP_MOD_NC001526_6222_6253_4_F |
| 2680 | Reverse | PAV_IMP_MOD_NC001526_6324_6355_4_R |
| 2681 | Forward | PAV_IMP_MOD_NC001526_6212_6238_F |
| 2681 | Reverse | PAV_IMP_MOD_NC001526_6324_6355_2_R |
| 2682 | Forward | PAV_IMP_MOD_NC001526_6212_6238_F |
| 2682 | Reverse | PAV_IMP_MOD_NC001526_6324_6355_3_R |
| 2683 | Forward | PAV_IMP_MOD_NC001526_6212_6238_F |
| 2683 | Reverse | PAV_IMP_MOD_NC001526_6324_6355_4_R |
| 2684 | Forward | PAV_IMP_MOD_NC001526_6212_6238_2_F |
| 2684 | Reverse | PAV_IMP_MOD_NC001526_6324_6355_2_R |
| 2685 | Forward | PAV_IMP_MOD_NC001526_6212_6238_3_F |
| 2685 | Reverse | PAV_IMP_MOD_NC001526_6324_6355_3_R |
| 2686 | Forward | PAV_IMP_MOD_NC001526_6212_6238_4_F |
| 2686 | Reverse | PAV_IMP_MOD_NC001526_6324_6355_4_R |
| 2687 | Forward | PAV_A9_MOD_NC001526_5632_5655_F |
| 2687 | Reverse | PAV_A9_MOD_NC001526_5691_5720_R |
| 2688 | Forward | PAV_A9_MOD_NC001526_5632_5655_2_F |
| 2688 | Reverse | PAV_A9_MOD_NC001526_5691_5720_R |
| 2689 | Forward | PAV_A9_MOD_NC001526_2688_2715_F |
| 2689 | Reverse | PAV_A9_MOD_NC001526_2773_2802_R |
| 2690 | Forward | PAV_A9_MOD_NC001526_2688_2715_F |
| 2690 | Reverse | PAV_A9_MOD_NC001526_2773_2802_2_R |
| 2691 | Forward | PAV_A9_MOD_NC001526_2688_2715_F |
| 2691 | Reverse | PAV_A9_MOD_NC001526_2773_2802_3_R |
| 2692 | Forward | PAV_A9_MOD_NC001526_1972_2003_F |
| 2692 | Reverse | PAV_A9_MOD_NC001526_2085_2112_R |
| 2693 | Forward | PAV_A7_A10_NC000904_1912_1937_F |
| 2693 | Reverse | PAV_A7_A10_NC000904_1997_2022_R |
| 2694 | Forward | PAV_A7_A10_NC000904_1912_1937_F |
| 2694 | Reverse | PAV_A7_A10_NC000904_1997_2022_2_R |
| 2695 | Forward | PAV_A7_A10_NC000904_1912_1937_2_F |
| 2695 | Reverse | PAV_A7_A10_NC000904_1997_2022_R |
| 2696 | Forward | PAV_A7_A10_NC000904_1912_1937_F |
| 2696 | Reverse | PAV_A7_A10_NC000904_2009_2036_R |

TABLE 1D

Gene Targets and GenBank gi Numbers

| Primer Pair Number | Target Genome Segment | HPV Strains Resolved | GenBank Reference gi Number |
|---|---|---|---|
| 2534 | major capsid protein | All | 9627100 |
| 2537 | major capsid protein | All | 9627100 |
| 2540 | replication protein | All | 9627100 |
| 2544 | E7 protein | All | 9626069 |
| 2545 | E1 protein | All | 9626069 |
| 2546 | E1 protein | All | 9633484 |
| 2547 | E1 protein | All | 9633484 |
| 2670 | major capsid protein | All | 9627100 |
| 2671 | major capsid protein | All | 9627100 |
| 2672 | major capsid protein | All | 9627100 |
| 2673 | major capsid protein | All | 9627100 |
| 2674 | major capsid protein | All | 9627100 |
| 2675 | major capsid protein | All | 9627100 |
| 2676 | major capsid protein | All | 9627100 |
| 2677 | major capsid protein | All | 9627100 |
| 2678 | major capsid protein | All | 9627100 |
| 2679 | major capsid protein | All | 9627100 |
| 2680 | major capsid protein | 16/31 | 9627100 |
| 2681 | major capsid protein | 16/31 | 9627100 |
| 2682 | major capsid protein | 16/31 | 9627100 |
| 2683 | major capsid protein | 16/31 | 9627100 |
| 2684 | major capsid protein | 16/31 | 9627100 |
| 2684 | major capsid protein | 16/31 | 9627100 |
| 2685 | major capsid protein | 18/45 + 6/11 | 9627100 |
| 2686 | major capsid protein | 18/45 + 6/12 | 9627100 |
| 2687 | major capsid protein | 18/45 + 6/11 | 9627100 |
| 2688 | replication protein | 18/45 + 6/12 | 9627100 |
| 2689 | replication protein | All | 9627100 |

It is noted that the primer pairs in Tables 1 and 2 could be combined into a single panel for detection one or more HPV (e.g., multiple types of HPV). The primers and primer pairs of Tables 1 and 2 could be used, for example, to detect human and animal infections. These primers and primer pairs may also be grouped (e.g., in panels or kits) for multiplex detection of other bioagents such as flavivirus, alphavirus, adenovirus, and other bioagents. In particular embodiments, the primers are used in assays for testing product safety.

EXAMPLE 2

De Novo Determination of Base Composition of Amplicons Using Molecular Mass Modified Deoxynucleotide Triphosphates Because the molecular masses of the four natural nucleobases fall within a narrow molecular mass range (A=313.058, G=329.052, C=289.046, T=304.046, values in Daltons—See, Table 3), a source of ambiguity in assignment of base composition may occur as follows: two nucleic acid strands having different base composition may have a difference of about 1 Da when the base composition difference between the two strands is G↔A (−15.994) combined with C↔T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052 is a molecular mass difference of only 0.994 Da. A 1 Da difference in molecular mass may be within the experimental error of a molecular mass measurement and thus, the relatively narrow molecular mass range of the four natural nucleobases imposes an uncertainty factor in this type of situation. One method for removing this theoretical 1 Da uncertainty factor uses amplification of a nucleic acid with one mass-tagged nucleobase and three natural nucleobases.

Addition of significant mass to one of the 4 nucleobases (dNTPs) in an amplification reaction, or in the primers themselves, will result in a significant difference in mass of the resulting amplicon (greater than 1 Da) arising from ambiguities such as the G↔A combined with C↔T event (Table 3). Thus, the same G↔A (−15.994) event combined with 5-Iodo-C↔T (−110.900) event would result in a molecular mass difference of 126.894 Da. The molecular mass of the base composition $A_{27}G_{30}$5-Iodo-$C_{21}T_{21}$ (33422.958) compared with $A_{26}G_{31}$5-Iodo-$C_{22}T_{20}$, (33549.852) provides a theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 3

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Mass spectra of bioagent-identifying amplicons may be analyzed using a maximum-likelihood processor, as is widely used in radar signal processing. This processor first makes maximum likelihood estimates of the input to the mass spectrometer for each primer by running matched filters for each base composition aggregate on the input data. This includes the response to a calibrant for each primer.

The algorithm emphasizes performance predictions culminating in probability-of-detection versus probability-of-false-detection plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bioagents (e.g., types of HPV) and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent-identifying amplicons for each primer are calibrated and a final maximum likelihood amplitude estimate per organism is made based upon the multiple single primer estimates. Models of system noise are factored into this two-stage maximum likelihood calculation. The processor reports the number of molecules of each base composition contained in the spectra. The quantity of amplicon corresponding to the appropriate primer set is reported as well as the quantities of primers remaining upon completion of the amplification reaction.

Base count blurring may be carried out as follows. Electronic PCR can be conducted on nucleotide sequences of the desired bioagents to obtain the different expected base counts that could be obtained for each primer pair. See for example, Schuler, *Genome Res.* 7:541-50, 1997; or the e-PCR program available from National Center for Biotechnology Information (NCBI, NIH, Bethesda, Md.). In one embodiment one or more spreadsheets from a workbook comprising a plurality of spreadsheets may be used (e.g., Microsoft Excel). First, in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet, "Sheet1" that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by selecting the most abundant strain's base type composition and adding it to the reference set, and then the next most abundant strain's base type composition is added until the threshold is met or exceeded.

For each base count not included in the reference base count set for the bioagent of interest, the script then proceeds to determine the manner in which the current base count differs from each of the base counts in the reference set. This difference may be represented as a combination of substitutions, $Si=Xi$, and insertions, $Ii=Yi$, or deletions, $Di=Zi$. If there is more than one reference base count, then the reported difference is chosen using rules that aim to minimize the number of changes and, in instances with the same number of changes, minimize the number of insertions or deletions. Therefore, the primary rule is to identify the difference with the minimum sum $(Xi+Yi)$ or $(Xi+Zi)$, e.g., one insertion rather than two substitutions. If there are two or more differences with the minimum sum, then the one that will be reported is the one that contains the most substitutions.

Differences between a base count and a reference composition are categorized as one, two, or more substitutions, one, two, or more insertions, one, two, or more deletions, and combinations of substitutions and insertions or deletions. The different classes of nucleobase changes and their probabilities of occurrence have been delineated in U.S. Patent Application Publication No. 2004209260 (U.S. application Ser. No. 10/418,514) which is incorporated herein by reference in entirety.

EXAMPLE 3

Validation of Primer Pairs

The primer pairs were tested against a panel of papillomaviruses obtained from ATCC. The following viruses were obtained as full-length plasmid clones: ATCC 45150D (HPV-6b); ATCC 45151D (HPV-11); ATCC 45152D (HPV-18); and ATCC 45113D (HPV-16). The broad primer pair number 2534 amplified all four viruses tested at two different dilutions of the plasmids. A series of primer modifications, including, for example, inosine substitutions to overcome potential sequence mismatches were introduced into the forward and reverse primer pairs. Most of the modified primers tested showed improved performance across the test isolates. In addition to the primers broadly targeting the major species, a series of primers targeting papillomavirus groups, A7, A9 and A10 that account for over 30 different papillomaviruses were also tested. Table 2 provides the primer pairs used for papillomavirus identification and indicates isolates tested, target virus groups and major species covered.

TABLE 4

Primer Pairs Targeting Human Papillomaviruses

| Primer Pair Number | Isolates Tested | Target Virus Group | Major Species Covered |
|---|---|---|---|
| 2537 2540 | HPV-16 | Group A9 | HPV-16, HPV-31, HPV-33, HPV-35, HPV-52, HPV-58, HPV-67, and RhPV |
| 2544 2545 | HPV-18 | Group A7 | HPV-18, HPV-39, HPV-45, HPV-59, HPV-68, and HPV-70 |
| 2546 | HPV-6, HPV-11 | Group A10 | HPV-6, HPV-11, HPV-13, HPV-44, HPV-55, and PCPV |

For additional testing and validation, two different HeLa cell lines infected with HPV-18 were obtained from ATCC (CCL-2 and CCL-2.2). These were tested at limiting dilutions using a subset of the primers tested above. Results are shown below. The primer pairs used for this test included the major human PaV primer pair 2685, the Group A7 targeted primers 2544 and 2545 and the Group A10 primer 2546.

In addition to testing the performance of the primers on the cell lines, plasmid DNA containing HPV-6b was spiked into the CCL-2 cell line to determine the dynamic range of detection of the two viruses, cell line derived HPV-18 and the plasmid-derived HPV-6b, simultaneously, In all the tests done, the broad primers as well as the Group A7 primers showed detection of HPV-18 in both cell lines at input levels between 1-10 cells per well. At an estimated copy number of approximately 20 HPV-18 genomes per cell, this corresponds to detection sensitivities between 20-200 genomes from cell lines containing papillomavirus sequences. In experiments done with a co-spike of HPV-6b plasmid into these cell lines, the detection ranges were comparable. HPV-6b was spiked in at two different, fixed concentrations of 200 copies and 2000 copies per well and amplified with the broad primer pair number 2534. Simultaneous detection of HPV-6b and HPV-18 was observed when the plasmid DNA was spiked in at 2000 copies into a range of CCL-2 cell concentration from 1000 to 0 per well. HPV-18 was detected in all wells with the exception of the lowest input level (10 cells/well), in the presence of 2000 copies of HPV-6b. HPV-6b (2000 copies) was detected in the presence of HeLa cell loads up to 600 cells/well, with an effective HPV-18 concentration of approximately 12000 genomes/well. In another experiment, a plasmid spike of approximately 200 copies per well was used. In this case, HPV-18 was detected at all test concentrations, including the lowest cell concentration of 10 cells per well. The dynamic range for detection of the two viruses simultaneously is between 5-10 fold at the lower and higher ends, giving an overall dynamic range of approximately 25 fold for the detection of competing templates in the presence of each other. These experiments indicate that two or more viruses can be simultaneously detected using the same assay.

EXAMPLE 4

Testing of Primer Pairs Against Strains of Human Papillomaviruses

A series of human papillomavirus samples were tested using the panel of primer pairs listed in Table 1 (primer pair numbers 2534, 2537, 2545, 2546, 2540, 2544, 2547 and 2684. The results are shown in Tables 5A and 5B and include experimentally determined base compositions. Strains of human papillomavirus identified are shown in the "Results" column. In most cases, the experimentally-determined base compositions matched the base compositions of strains of human papillomaviruses stored in a base composition database.

TABLE 5A

Base Composition Results for Primer Pair Numbers 2534, 2537, 2545 and 2546

| Sample ID | Result | Primer Pair 2534 | Primer Pair 2537 | Primer Pair 2545 | Primer Pair 2546 |
|---|---|---|---|---|---|
| HPV13299 | HPV type 74 | 38 30 22 44 | NoDetect | NoDetect | 47 48 21 37 |
| HPV13308 | HPV type 44 | 41 30 19 44 | Redo | NoDetect | 47 49 22 35 |
| HPV15465 | HPV type 40 | 36 33 18 47 | NoDetect | NoDetect | NoDetect |
| HPV16837 | HPV type 61 | 39 33 19 43 | NoDetect | NoDetect | 47 50 21 35 |
| HPV17259 | HPV type 6 | 39 31 18 46 | NoDetect | NoDetect | 49 44 25 35 |
| HPV0137 | No matches | 35 33 18 48 | NoDetect | NoDetect | NoDetect |
| HPV0138 | HPV type 40 | 36 33 18 47 | 18 26 19 26 | NoDetect | Redo |
| HPV0139 | HPV type 6 | 41 30 20 43 + 39 31 18 46 | 20 21 19 29 | unknown bc | 49 44 25 35 |
| HPV0140 | HPV type 6 | 39 31 18 46 | NoDetect | NoDetect | 49 44 25 35 |
| HPV0141 | HPV type 51 | 34 32 25 43 | NoDetect | NoDetect | NoDetect |
| HPV0142 | Negative | Redo | NoDetect | NoDetect | Redo |
| Blank | Negative | NoDetect | IP | NoDetect | NoDetect |
| HPV17436 | HPV cand 62 (Qv18091) | 39 34 20 41 | NoDetect | Redo | NoDetect |
| HPV17682 | Negative | NoDetect | NoDetect | Redo | NoDetect |
| HPV17741 | HPV type 6 | 39 31 18 46 | NoDetect | NoDetect | 49 44 25 35 |
| HPV18249 | HPV type 11 | 38 31 20 45 | NoDetect | NoDetect | 49 46 23 35 (SNP) |
| HPV18287 | HPV type cand 85 | 38 32 16 48 | 20 23 20 26 | 36 36 16 23 | 49 44 25 35 |
| HPV19189 | Negative | NoDetect | NoDetect | NoDetect | Redo |
| HPV19267 | Negative | NoDetect | NoDetect | NoDetect | NoDetect |
| HPV19385 | Negative | NoDetect | NoDetect | NoDetect | NoDetect |
| HPV19463 | HPV type 33 | 40 33 15 46 | 19 25 19 26 | Redo | NoDetect |
| HPV19479 | HPV type 52 | Redo | 17 25 20 27 | Redo | NoDetect |
| HPV19486 | HPV type 70 | 40 34 21 39 | IP | 37 34 19 21 | Redo |
| HPV19802 | HPV type 45 | 39 34 18 43 | NoDetect | 40 32 12 27 | NoDetect |
| HPV19863 | HPV type 35/35H | NoDetect | 20 24 20 25 | Redo | NoDetect |
| HPV19918 | No matches | NoDetect | NoDetect | Redo | NoDetect |
| HPV19955 | HPV type 39 | 38 35 17 44 | NoDetect | 38 34 16 23 | NoDetect |
| HPV20010 | No matches | 35 36 19 44 | NoDetect | NoDetect | NoDetect |
| HPV20027 | HPV type 52 | 39 34 15 46 | 17 25 20 27 | NoDetect | NoDetect |
| HPV20144 | HPV type 16 | NoDetect | 18 24 20 27 | NoDetect | NoDetect |
| HPV20152 | HPV type 53 | 41 30 18 45 | Redo | NoDetect | NoDetect |
| HPV20215 | HPV type 71 | 38 33 21 42 | NoDetect | NoDetect | NoDetect |
| HPV20274 | Negative | NoDetect | NoDetect | Redo | NoDetect |
| HPV20289 | No matches | Redo | NoDetect | NoDetect | NoDetect |
| HPV20300 | Negative | NoDetect | NoDetect | NoDetect | NoDetect |
| HPV20341 | HPV type 31 | 39 29 16 50 | 19 25 20 25 (SNP) | NoDetect | NoDetect |
| HPV20361 | Negative | NoDetect | NoDetect | NoDetect | NoDetect |
| HPV20370 | HPV type 18 | 38 33 16 47 | NoDetect | 40 30 14 27 | NoDetect |
| HPV20384 | No matches | 37 35 18 44 | 18 26 19 26 | NoDetect | NoDetect |
| HPV20387 | Negative | NoDetect | NoDetect | NoDetect | NoDetect |
| HPV20441 | Negative | NoDetect | NoDetect | NoDetect | NoDetect |
| HPV20507 | Negative | NoDetect | NoDetect | Redo | NoDetect |
| HPV20521 | HPV type 59 | 40 33 15 46 | NoDetect | NoDetect | NoDetect |
| HPV0137 | HPV type 40/74 | 36 33 18 47 | NoDetect | NoDetect | 51 43 22 37 |
| HPV0138 | No matches | 35 33 18 48 | NoDetect | NoDetect | NoDetect |
| HPV0139 | HPV type 6 | 39 31 18 46 | NoDetect | NoDetect | 49 44 25 35 |
| HPV0140 | HPV type 6 | 39 31 18 46 | 20 21 19 29 | NoDetect | 49 44 25 35 |
| HPV0141 | Negative | NoDetect | NoDetect | NoDetect | NoDetect |
| HPV0142 | Negative | NoDetect | NoDetect | NoDetect | NoDetect |
| HPV0143 | HPV type 55 | NoDetect | NoDetect | NoDetect | 47 48 21 37 |
| HPV0144 | Negative | NoDetect | NoDetect | Redo | NoDetect |
| HPV0145 | Negative | NoDetect | NoDetect | NoDetect | NoDetect |
| HPV0146 | HPV type 59 | NoDetect | NoDetect | NoDetect | NoDetect |
| HPV0147 | No matches | 43 30 17 44 | 20 25 18 26 | NoDetect | NoDetect |
| HPV0148 | No matches | 36 34 23 41 + 39 34 24 37 | 20 25 18 26 | NoDetect | NoDetect |
| HPV0149 | HPV type 67 | NoDetect | 17 26 19 27 | NoDetect | NoDetect |
| HPV0150 | No matches | NoDetect | 18 26 19 26 | NoDetect | NoDetect |
| HPV0151 | HPV type 74 | 38 30 20 46 | NoDetect | NoDetect | 51 43 22 37 |
| HPV0152 | HPV type 74 | 38 30 20 46 | NoDetect | NoDetect | 51 43 22 37 |
| HPV0153 | HPV type 6 | NoDetect | NoDetect | NoDetect | 49 44 25 35 |
| HPV0154 | HPV type 72 | 39 30 24 41 | NoDetect | Redo | NoDetect |
| HPV0155 | Negative | Redo | NoDetect | NoDetect | NoDetect |
| HPV0156 | No matches | NoDetect | 18 26 19 26 | NoDetect | NoDetect |
| HPV0157 | Negative | NoDetect | NoDetect | NoDetect | NoDetect |
| HPV0158 | Negative | NoDetect | Redo | Redo | NoDetect |
| HPV0159 | Negative | NoDetect | NoDetect | NoDetect | NoDetect |
| HPV0160 | Negative | NoDetect | NoDetect | NoDetect | NoDetect |

TABLE 5A-continued

Base Composition Results for Primer Pair Numbers 2534, 2537, 2545 and 2546

| Sample ID | Result | Primer Pair 2534 | Primer Pair 2537 | Primer Pair 2545 | Primer Pair 2546 |
|---|---|---|---|---|---|
| HPV0161 | HPV type 6 | 39 31 18 46 | NoDetect | NoDetect | NoDetect |
| HPV0162 | Negative | NoDetect | NoDetect | NoDetect | NoDetect |
| HPV0163 | Negative | Redo | NoDetect | Redo | NoDetect |
| HPV0164 | No matches | 35 32 25 42 | NoDetect | NoDetect | NoDetect |
| HPV0165 | No matches | 37 34 22 41 | NoDetect | NoDetect | NoDetect |
| HPV0166 | Negative | NoDetect | NoDetect | NoDetect | NoDetect |
| HPV0167 | No matches | Redo | NoDetect | Redo | NoDetect |
| HPV0168 | Negative | NoDetect | NoDetect | Redo | NoDetect |
| HPV0169 | HPV type 74 | 38 30 22 44 | NoDetect | NoDetect | NoDetect |
| HPV0170 | HPV type 74 | 38 30 20 46 | NoDetect | Redo | NoDetect |
| HPV0171 | HPV type 44 | NoDetect | 19 25 19 26 (~25 copies) | NoDetect | 47 49 22 35 |
| HPV0172 | HPV type 44 | 41 30 19 44 | NoDetect | NoDetect | 47 49 22 35 |
| HPV179 | HPV type 54 | NoDetect | 22 23 20 24 | NoDetect | NoDetect |
| HPV180 | HPV type 54 | 41 30 22 41 | 24 21 20 24 | Redo | Redo |
| HPV181 | No matches | NoDetect | 18 26 19 26 | NoDetect | NoDetect |
| HPV182 | HPV type 44 | 41 30 19 44 | NoDetect | Redo | 47 49 22 35 |
| HPV183 | HPV type 59/33 | 40 33 15 46 | NoDetect | NoDetect | NoDetect |
| HPV184 | HPV type 30 | 42 28 20 44 | NoDetect | NoDetect | NoDetect |
| HPV185 | HPV type 16 | 43 30 17 44 + 39 34 15 46 | 18 24 20 27 | NoDetect | Redo |
| HPV186 | No matches | 36 34 23 41 | 20 25 18 26 | NoDetect | Redo |
| HPV187 | No matches | NoDetect | 18 26 19 26 | NoDetect | NoDetect |
| HPV188 | HPV type 11, 13, 74, 44, 55, | 37 31 20 46 | 18 26 19 26 | NoDetect | NoDetect |
| HPV189 | No matches | NoDetect | NoDetect | NoDetect | NoDetect |
| HPV190 | Negative | NoDetect | NoDetect | NoDetect | NoDetect |
| HPV191 | HPV type 74 | 38 30 20 46 | NoDetect | Redo | 51 43 22 37 |
| HPV192 | Negative | NoDetect | NoDetect | NoDetect | NoDetect |
| HPV193 | Negative | NoDetect | NoDetect | NoDetect | NoDetect |
| HPV194 | Negative | NoDetect | NoDetect | NoDetect | NoDetect |
| HPV195 | Negative | NoDetect | NoDetect | Redo | NoDetect |
| HPV196 | HPV type 6 | 39 31 18 46 | NoDetect | Redo | 49 44 25 35 |
| HPV197 | HPV type 72 | 39 30 24 41 | NoDetect | Redo | NoDetect |
| HPV198 | HPV type 70 | NoDetect | 19 24 19 27 | Redo | 47 50 21 35 |
| HPV199 | HPV type 44 | 41 30 19 44 | 19 24 19 27 | Redo | 47 49 22 35 |
| HPV200 | Negative | NoDetect | NoDetect | Redo | NoDetect |
| HPV201 | No matches | NoDetect | NoDetect | Redo | Redo |
| HPV202 | HPV type 6 | Redo | NoDetect | Redo | 49 44 25 35 |
| HPV203 | Negative | Redo | NoDetect | Redo | NoDetect |
| HPV204 | Negative | NoDetect | NoDetect | Redo | NoDetect |
| HPV205 | HPV type 39 | 35 32 25 42; 38 35 17 44 | NoDetect | NoDetect | NoDetect |
| HPV206 | Negative | NoDetect | NoDetect | Redo | Redo |
| HPV250425 | HPV type 6vc | 39 30 18 47 | NoDetect | NoDetect | NoDetect |
| HPV261931 | HPV type 55 | NoDetect | NoDetect | NoDetect | 47 48 21 37 |
| HPV340160 | HPV type 84 | 40 30 21 43 | 19 25 21 24 | NoDetect | Redo |
| HPV397645 | HPV type cand 87 | NoDetect | 19 25 20 25 | NoDetect | NoDetect |
| HPV403876 | HPV type cand 85 | 38 32 16 48 | NoDetect | 36 36 16 23 | NoDetect |
| HPV525736 | HPV type 42 | NoDetect | 20 21 19 29 | NoDetect | NoDetect |
| HPV678087 | HPV type 70 | 39 34 21 40 | NoDetect | 37 34 19 21 | Redo |
| HPV683500 | HPV type 40 | 36 33 18 47 | NoDetect | NoDetect | NoDetect |
| HPV711336 | HPV type 44 | 41 30 19 44 | NoDetect | NoDetect | 47 50 21 35 |
| HPV766300 | HPV type 56 | 37 35 20 42 | 23 22 17 27 | NoDetect | Redo |
| HPV781687 | HPV type 72 | 39 30 24 41 | NoDetect | NoDetect | NoDetect |
| HPV857673 | HPV type 44 | 43 29 17 45 | NoDetect | NoDetect | 47 49 22 35 |
| HPV901338 | Negative | NoDetect | NoDetect | NoDetect | NoDetect |
| HPV901338 | Negative | Redo | NoDetect | NoDetect | NoDetect |
| HPV922829 | Negative | NoDetect | NoDetect | NoDetect | NoDetect |
| HPV922829 | Negative | NoDetect | NoDetect | Redo | NoDetect |
| HPV932724 | HPV type 54 | 41 30 22 41 | 24 21 20 24 | NoDetect | 47 49 22 35 |
| HPV999950 | HPV type 67 | NoDetect | 17 26 19 27 | NoDetect | NoDetect |

TABLE 5B

Base Composition Results for Primer Pair Numbers 2540, 2544, 2547 and 2684

| Sample ID | Result | Primer Pair 2540 | Primer Pair 2544 | Primer Pair 2547 | Primer Pair 2684 |
|---|---|---|---|---|---|
| HPV13299 | HPV type 74 | Redo | NoDetect | 24 21 18 17 | 41 31 25 47 |
| HPV13308 | HPV type 44 | NoDetect | NoDetect | 23 22 18 17 | 42 32 22 48 |
| HPV15465 | HPV type 40 | NoDetect | NoDetect | Redo | 37 35 21 51 |
| HPV16837 | HPV type 61 | NoDetect | 40 38 32 38 | Redo | NoDetect |
| HPV17259 | HPV type 6 | NoDetect | NoDetect | 23 21 20 16 | 41 32 22 49 |
| HPV0137 | No matches | NoDetect | NoDetect | NoDetect | 36 35 21 52 |
| HPV0138 | HPV type 40 | NoDetect | 40 38 32 38 | Redo | 37 35 21 51 |
| HPV0139 | HPV type 6 | NoDetect | NoDetect | 23 21 20 16 | 44 32 22 46 + 41 32 22 49 |
| HPV0140 | HPV type 6 | NoDetect | NoDetect | 23 21 20 16 | 41 32 22 49 |
| HPV0141 | HPV type 51 | NoDetect | NoDetect | NoDetect | 36 34 27 47 |
| HPV0142 | Negative | Redo | NoDetect | NoDetect | NoDetect |
| Blank | Negative | NoDetect | NoDetect | Redo | NoDetect |
| HPV17436 | HPV cand 62 (Qv18091) | NoDetect | NoDetect | NoDetect | 43 36 23 42 |
| HPV17682 | Negative | NoDetect | NoDetect | NoDetect | NoDetect |
| HPV17741 | HPV type 6 | Redo | NoDetect | 23 21 20 16 | 41 32 22 49 + 44 32 22 46 |
| HPV18249 | HPV type 11 | NoDetect | 39 37 34 38 | 22 22 17 19 | 40 32 23 49 |
| HPV18287 | HPV type cand 85 | 54 28 16 43 | NoDetect | 23 21 20 16 | NoDetect |
| HPV19189 | Negative | NoDetect | NoDetect | NoDetect | NoDetect |
| HPV19267 | Negative | Redo | NoDetect | NoDetect | NoDetect |
| HPV19385 | Negative | Redo | NoDetect | Redo | NoDetect |
| HPV19463 | HPV type 33 | 60 26 18 37 | NoDetect | Redo | 43 35 18 48 |
| HPV19479 | HPV type 52 | NoDetect | NoDetect | Redo | NoDetect |
| HPV19486 | HPV type 70 | NoDetect | 40 35 31 42 | Redo | NoDetect |
| HPV19802 | HPV type 45 | NoDetect | 36 40 29 43 | Redo | 42 36 20 46 |
| HPV19863 | HPV type 35/35H | 59 26 16 40 | NoDetect | Redo | NoDetect |
| HPV19918 | No matches | NoDetect | 41 37 32 38 | Redo | Redo |
| HPV19955 | HPV type 39 | Redo | 39 37 34 38 | Redo | NoDetect |
| HPV20010 | No matches | NoDetect | NoDetect | Redo | 39 38 22 45 |
| HPV20027 | HPV type 52 | 59 28 22 32 | NoDetect | Redo | NoDetect |
| HPV20144 | HPV type 16 | 59 27 19 36 | NoDetect | Redo | NoDetect |
| HPV20152 | HPV type 53 | NoDetect | NoDetect | Redo | NoDetect |
| HPV20215 | HPV type 71 | NoDetect | NoDetect | NoDetect | 41 34 24 45 |
| HPV20274 | Negative | NoDetect | NoDetect | Redo | NoDetect |
| HPV20289 | No matches | NoDetect | NoDetect | Redo | 36 34 26 48 |
| HPV20300 | Negative | NoDetect | NoDetect | NoDetect | NoDetect |
| HPV20341 | HPV type 31 | 58 29 15 39 | NoDetect | Redo | 41 30 19 54 |
| HPV20361 | Negative | NoDetect | NoDetect | NoDetect | NoDetect |
| HPV20370 | HPV type 18 | NoDetect | 36 38 33 41 | NoDetect | 42 34 18 50 |
| HPV20384 | No matches | 56 30 20 35 | NoDetect | Redo | 39 39 21 45 |
| HPV20387 | Negative | NoDetect | NoDetect | NoDetect | NoDetect |
| HPV20441 | Negative | NoDetect | NoDetect | NoDetect | NoDetect |
| HPV20507 | Negative | NoDetect | NoDetect | NoDetect | NoDetect |
| HPV20521 | HPV type 59 | 57 27 20 37 | 38 36 31 43 | Redo | 45 34 18 47 |
| HPV0137 | HPV type 40/74 | NoDetect | NoDetect | 23 22 18 17 | 37 35 21 51; 41 31 23 49 |
| HPV0138 | No matches | Redo | NoDetect | NoDetect | 47 33 23 41 |
| HPV0139 | HPV type 6 | NoDetect | NoDetect | Redo | NoDetect |
| HPV0140 | HPV type 6 | NoDetect | NoDetect | Redo | 44 32 22 46 |
| HPV0141 | Negative | NoDetect | NoDetect | NoDetect | NoDetect |
| HPV0142 | Negative | NoDetect | NoDetect | Redo | NoDetect |
| HPV0143 | HPV type 55 | NoDetect | NoDetect | 23 22 18 17 | 42 31 25 46 |
| HPV0144 | Negative | NoDetect | NoDetect | Redo | NoDetect |
| HPV0145 | Negative | NoDetect | NoDetect | Redo | NoDetect |
| HPV0146 | HPV type 59 | 57 27 20 37 | 37 37 31 43 | Redo | 45 34 18 47 |
| HPV0147 | No matches | NoDetect | NoDetect | NoDetect | 43 33 19 49 |
| HPV0148 | No matches | NoDetect | NoDetect | NoDetect | 40 36 26 42/ 35 38 26 45 |
| HPV0149 | HPV type 67 | 56 30 19 36 | NoDetect | Redo | NoDetect |
| HPV0150 | No matches | NoDetect | NoDetect | Redo | NoDetect |
| HPV0151 | HPV type 74 | NoDetect | NoDetect | 23 22 18 17 | 41 31 23 49 |
| HPV0152 | HPV type 74 | NoDetect | NoDetect | 23 22 18 17 | 41 31 23 49 |
| HPV0153 | HPV type 6 | NoDetect | NoDetect | 23 21 20 16 | NoDetect |
| HPV0154 | HPV type 72 | NoDetect | NoDetect | NoDetect | NoDetect |
| HPV0155 | Negative | NoDetect | NoDetect | Redo | NoDetect |
| HPV0156 | No matches | NoDetect | NoDetect | Redo | NoDetect |
| HPV0157 | Negative | Redo | NoDetect | Redo | NoDetect |
| HPV0158 | Negative | Redo | NoDetect | Redo | NoDetect |
| HPV0159 | Negative | NoDetect | NoDetect | Redo | NoDetect |
| HPV0160 | Negative | Redo | NoDetect | NoDetect | NoDetect |
| HPV0161 | HPV type 6 | NoDetect | NoDetect | Redo | NoDetect |

TABLE 5B-continued

Base Composition Results for Primer Pair Numbers 2540, 2544, 2547 and 2684

| Sample ID | Result | Primer Pair 2540 | Primer Pair 2544 | Primer Pair 2547 | Primer Pair 2684 |
|---|---|---|---|---|---|
| HPV0162 | Negative | Redo | NoDetect | NoDetect | NoDetect |
| HPV0163 | Negative | NoDetect | NoDetect | Redo | NoDetect |
| HPV0164 | No matches | Redo | NoDetect | Redo | 39 34 28 43 |
| HPV0165 | No matches | Redo | NoDetect | Redo | NoDetect |
| HPV0166 | Negative | Redo | NoDetect | NoDetect | NoDetect |
| HPV0167 | No matches | NoDetect | 38 40 31 39 | Redo | NoDetect |
| HPV0168 | Negative | Redo | NoDetect | NoDetect | NoDetect |
| HPV0169 | HPV type 74 | Redo | NoDetect | 24 21 18 17 | 41 31 25 47 |
| HPV0170 | HPV type 74 | NoDetect | NoDetect | 23 22 18 17 | 40 31 24 49 |
| HPV0171 | HPV type 44 | Redo | NoDetect | 23 22 18 17 | 42 32 22 48 + 44 32 22 46 |
| HPV0172 | HPV type 44 | NoDetect | NoDetect | 23 22 18 17 | 42 32 22 48 |
| HPV179 | HPV type 54 | NoDetect | NoDetect | NoDetect | NoDetect |
| HPV180 | HPV type 54 | NoDetect | NoDetect | Redo | NoDetect |
| HPV181 | No matches | NoDetect | NoDetect | Redo | NoDetect |
| HPV182 | HPV type 44 | NoDetect | NoDetect | 23 22 18 17 | 42 32 22 48 |
| HPV183 | HPV type 59/33 | 57 27 20 37 | 37 37 32 42 | Redo | 45 34 18 47 |
| HPV184 | HPV type 30 | NoDetect | NoDetect | NoDetect | 43 30 21 50 |
| HPV185 | HPV type 16 | 59 27 19 36 | NoDetect | Redo | 43 33 19 49 |
| HPV186 | No matches | NoDetect | NoDetect | Redo | 40 36 26 42 |
| HPV187 | No matches | NoDetect | NoDetect | NoDetect | NoDetect |
| HPV188 | HPV type 11, 13, 74, 44, 55, etc. | NoDetect | NoDetect | 23 22 18 17 | 40 32 23 49 |
| HPV189 | No matches | NoDetect | 38 40 31 39 | NoDetect | NoDetect |
| HPV190 | Negative | NoDetect | NoDetect | Redo | NoDetect |
| HPV191 | HPV type 74 | NoDetect | NoDetect | 23 22 18 17 | 41 31 23 49 |
| HPV192 | Negative | NoDetect | NoDetect | NoDetect | NoDetect |
| HPV193 | Negative | NoDetect | NoDetect | Redo | NoDetect |
| HPV194 | Negative | NoDetect | NoDetect | Redo | NoDetect |
| HPV195 | Negative | NoDetect | NoDetect | Redo | Redo |
| HPV196 | HPV type 6 | Redo | NoDetect | NoDetect | 41 32 22 49 |
| HPV197 | HPV type 72 | NoDetect | NoDetect | NoDetect | 41 34 24 45 |
| HPV198 | HPV type 70 | NoDetect | NoDetect | NoDetect | NoDetect |
| HPV199 | HPV type 44 | NoDetect | NoDetect | Redo | 42 32 22 48 |
| HPV200 | Negative | NoDetect | NoDetect | Redo | NoDetect |
| HPV201 | No matches | NoDetect | NoDetect | Redo | 39 39 21 45 |
| HPV202 | HPV type 6 | Redo | NoDetect | 23 21 20 16 | 41 32 22 49 |
| HPV203 | Negative | NoDetect | NoDetect | NoDetect | NoDetect |
| HPV204 | Negative | NoDetect | NoDetect | Redo | NoDetect |
| HPV205 | HPV type 39 | NoDetect | 39 37 34 38 | Redo | 39 34 28 43 |
| HPV206 | Negative | NoDetect | NoDetect | Redo | NoDetect |
| HPV250425 | HPV type 6vc | NoDetect | NoDetect | NoDetect | NoDetect |
| HPV261931 | HPV type 55 | Redo | NoDetect | 23 22 18 17 | NoDetect |
| HPV340160 | HPV type 84 | Redo | NoDetect | Redo | 36 37 26 45 |
| HPV397645 | HPV type cand 87 | Redo | NoDetect | Redo | NoDetect |
| HPV403876 | HPV type cand 85 | 54 28 16 43 | NoDetect | Redo | NoDetect |
| HPV525736 | HPV type 42 | Redo | NoDetect | Redo | NoDetect |
| HPV678087 | HPV type 70 | Redo | NoDetect | Redo | NoDetect |
| HPV683500 | HPV type 40 | Redo | NoDetect | NoDetect | 37 35 21 51 |
| HPV711336 | HPV type 44 | NoDetect | NoDetect | 23 22 18 17 | 42 32 22 48 |
| HPV766300 | HPV type 56 | Redo | NoDetect | NoDetect | NoDetect |
| HPV781687 | HPV type 72 | Redo | NoDetect | NoDetect | NoDetect |
| HPV857673 | HPV type 44 | NoDetect | NoDetect | 23 22 18 17 | 42 32 22 48 |
| HPV901338 | Negative | NoDetect | NoDetect | NoDetect | NoDetect |
| HPV901338 | Negative | Redo | NoDetect | Redo | NoDetect |
| HPV922829 | Negative | NoDetect | NoDetect | NoDetect | NoDetect |
| HPV922829 | Negative | Redo | NoDetect | NoDetect | Redo |
| HPV932724 | HPV type 54 | Redo | NoDetect | 23 22 18 17 | 45 31 23 45 |
| HPV999950 | HPV type 67 | 56 30 19 36 | NoDetect | NoDetect | NoDetect |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, interne web sites, and the like) cited in the present application is incorporated herein by reference in its entirety.

We claim:

1. A composition comprising purified oligonucleotides, wherein the oligonucleotides consist of a primer pair that consists of a forward and a reverse primer, wherein the forward and reverse primers consist of sequences selected from the group of primer pair sequences consisting of SEQ ID NOS: 1:9, 2:10, 3:11, 4:12, 5:13, 6:14, 7:15, and 8:16.

2. A kit comprising the composition of claim 1.

3. The composition of claim 1, wherein said forward and/or reverse primer comprises at least one molecular mass modifying tag.

4. The composition of claim 1, wherein said forward and/or reverse primer comprises at least one modified nucleobase.

5. The composition of claim 4, wherein said modified nucleobase is 5-propynyluracil or 5-propynylcytosine.

6. The composition of claim 4, wherein said modified nucleobase is a mass modified nucleobase.

7. The composition of claim 6, wherein said mass modified nucleobase is 5-Iodo-C.

8. The composition of claim 4, wherein said modified nucleobase is a universal nucleobase.

9. The composition of claim 8, wherein said universal nucleobase is inosine.

10. A method of determining the presence of a HPV in at least one sample, the method comprising:
   (a) amplifying one or more segments of at least one nucleic acid from said sample using the primer pair of claim 1 to produce at least one amplification product; and
   (b) detecting said amplification product, thereby determining said presence of said HPV in said sample.

11. The method of claim 10, wherein (a) comprises amplifying said one or more segments of said at least one nucleic acid from at least two samples obtained from different geographical locations to produce at least two amplification products, and (b) comprises detecting said amplification products, thereby tracking an epidemic spread of said HPV.

12. The method of claim 10, wherein (b) comprises determining an amount of said HPV in said sample.

13. The method of claim 10, wherein (b) comprises detecting a molecular mass of said amplification product.

14. The method of claim 10, wherein (b) comprises determining a base composition of said amplification product, wherein said base composition identifies the number of A residues, C residues, T residues, G residues, U residues, analogs thereof and/or mass tag residues thereof in said amplification product, whereby said base composition indicates the presence of HPV in said sample or identifies said HPV in said sample.

15. The method of claim 14, comprising comparing said base composition of said amplification product to calculated or measured base compositions of amplification products of one or more known HPV present in a database with the proviso that sequencing of said amplification product is not used to indicate the presence of or to identify said HPV, wherein a match between said determined base composition and said calculated or measured base composition in said database indicates the presence of or identifies said HPV.

16. A method of identifying one or more HPV bioagents in a sample, the method comprising:
  (a) amplifying two or more segments of a nucleic acid from said one or more HPV bioagents in said sample with two or more oligonucleotide primer pairs of claim 1 to obtain two or more amplification products;
  (b) determining two or more molecular masses and/or base compositions of said two or more amplification products; and
  (c) comparing said two or more molecular masses and/or said base compositions of said two or more amplification products with known molecular masses and/or known base compositions of amplification products of known HPV bioagents produced with said two or more primer pairs to identify said one or more HPV bioagents in said sample.

17. The method of claim 16, comprising identifying said one or more HPV bioagents in said sample using three, four, five, six, seven, eight or more primer pairs.

18. The method of claim 16, wherein said one or more HPV bioagents in said sample cannot be identified using a single primer pair of said two or more primer pairs.

19. The method of claim 16, comprising obtaining said two or more molecular masses of said two or more amplification products via mass spectrometry.

20. The method of claim 16, comprising calculating said two or more base compositions from said two or more molecular masses of said two or more amplification products.

21. The method of claim 16, wherein said HPV bioagents are selected from the group consisting of a Papillomaviridae family, a genus thereof, a species thereof, a sub-species thereof, and combinations thereof.

22. The method of claim 16, wherein said determining said two or more molecular masses and/or base compositions is conducted without sequencing said two or more amplification products.

23. The method of claim 16, wherein said one or more HPV bioagents in said sample cannot be identified using a single primer pair of said two or more primer pairs.

24. The method of claim 16, wherein said one or more HPV bioagents in a sample are identified by comparing three or more molecular masses and/or base compositions of three or more amplification products with a database of known molecular masses and/or known base compositions of amplification products of known HPV bioagents produced with said three or more primer pairs.

25. The method of claim 16, wherein said two or more segments of said nucleic acid are amplified from a single gene.

26. The method of claim 16, wherein said two or more segments of said nucleic acid are amplified from different genes.

27. The method of claim 16, wherein members of said primer pairs hybridize to conserved regions of said nucleic acid that flank a variable region.

28. The method of claim 27, wherein said variable region varies between at least two of said HPV bioagents.

29. The method of claim 27, wherein said variable region uniquely varies between at least five of said HPV bioagents.

30. The method of claim 16, wherein said two or more amplification products obtained in (a) comprise major classification and subgroup identifying amplification products.

31. The method of claim 30, comprising comparing said molecular masses and/or said base compositions of said two or more amplification products to calculated or measured molecular masses or base compositions of amplification products of known HPV bioagents in a database comprising genus specific amplification products, species specific amplification products, strain specific amplification products or nucleotide polymorphism specific amplification products produced with said two or more oligonucleotide primer pairs, wherein one or more matches between said two or more amplification products and one or more entries in said database identifies said one or more HPV bioagents, classifies a major classification of said one or more HPV bioagents, and/or differentiates between subgroups of known and unknown HPV bioagents in said sample.

32. The method of claim 31, wherein said major classification of said one or more HPV bioagents comprises a genus or species classification of said one or more HPV bioagents.

33. The method of claim 31, wherein said subgroups of known and unknown HPV bioagents comprise family, strain and nucleotide variations of said one or more HPV bioagents.

* * * * *